(12) United States Patent
Vadigepalli et al.

(10) Patent No.: US 10,982,214 B2
(45) Date of Patent: Apr. 20, 2021

(54) INHIBITING MICRORNA TO PREVENT DEVELOPMENT OF ESSENTIAL HYPERTENSION

(71) Applicant: THOMAS JEFFERSON UNIVERSITY, Philadelphia, PA (US)

(72) Inventors: Rajanikanth Vadigepalli, Aston, PA (US); Danielle Decicco, Philadelphia, PA (US); James Schwaber, Arden, DE (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 16/319,652

(22) PCT Filed: Jul. 20, 2017

(86) PCT No.: PCT/US2017/043130
§ 371 (c)(1),
(2) Date: Jan. 22, 2019

(87) PCT Pub. No.: WO2018/017865
PCT Pub. Date: Jan. 25, 2018

(65) Prior Publication Data
US 2019/0264212 A1 Aug. 29, 2019

Related U.S. Application Data

(60) Provisional application No. 62/364,616, filed on Jul. 20, 2016.

(51) Int. Cl.
*A61K 48/00* (2006.01)
*C07H 21/04* (2006.01)
*C12N 15/113* (2010.01)

(52) U.S. Cl.
CPC ........ *C12N 15/1137* (2013.01); *C12N 15/113* (2013.01); *C12N 2310/11* (2013.01); *C12N 2310/113* (2013.01); *C12N 2310/141* (2013.01); *C12N 2310/3231* (2013.01); *C12N 2320/31* (2013.01)

(58) Field of Classification Search
CPC .......................... A61K 31/713; C12N 15/113
See application file for complete search history.

(56) References Cited

FOREIGN PATENT DOCUMENTS

| EP | 2 385 120 A1 | * | 9/2011 | ........... A61K 31/713 |
|---|---|---|---|---|
| WO | WO 2011/057003 A2 | * | 5/2011 | ........... A61K 31/713 |
| WO | 2015171641 A1 | | 11/2015 | |
| WO | WO 2015/171641 A1 | * | 11/2015 | ........... A61K 31/713 |
| WO | 2016069717 A1 | | 5/2016 | |

OTHER PUBLICATIONS

Affleck, V.S., et al., "The projection and synaptic organisation of NTS afferent connection with presympathetic neurons, GABA and nNOS neurons in the paraventricular nucleus of the hypothalamus", Neuroscience, vol. 219, pp. 48-61, 2012.
Agarwal, S.K., et al., "Reciprocal connections between nucleus tractus solitarii and rostral ventrolateral medulla", Brain Research, vol. 523, No. 2, pp. 305-308.
Allen, A.M., et al., "Angiotensin II receptor binding and the baroreflex pathway", Clinical and Experimental Hypertension, Part A, Theory and Practice, vol. 10, Suppl 1, pp. 63-78, 1988.
Anisman, H., et al., "Cytokines, stress and depressive illness: brain-immune interactions", Annals of Medicine, vol. 35, No. 1, pp. 2-11, 2003.
Arnold, A.C., et al., "Angiotensin-(1-12) requires angiotensin converting enzyme and AT1 receptors for cardiovascular actions within the solitary tract nucleus", American Journal of Physiology. Heart and Circulatory Physiology, vol. 299, No. 3, pp. H763-71, 2010.
Aronow, W.S., "What Should the Optimal Systolic Blood Pressure Goal Be in Treating Older Persons with Hypertension?", Journal of the American Medical Directors Association, vol. 17, No. 1, pp. 571-573, 2016.
Ashhab, M.U., et al., "Expressions of tumor necrosis factor alpha and microRNA-155 in immature rat model of status epilepticus and children with mesial temporal lobe epilepsy", Journal of Molecular Neuroscience, vol. 51, No. 3, pp. 950-958, 2013.
Atanur, S.S., et al., "The genome sequence of the spontaneously hypertensive rat: Analysis and functional significance", Genome Research, vol. 20, No. 6, pp. 791-803, 2010.
Averill, D.B., et al., "Losartan, nonpeptide angiotensin II-type 1 (AT1) receptor antagonis, attenuates pressor and sympathoexcitatory responses evoked by angiotensin II and L-glutamate in rostral ventrolateral medulla". Brain Research, vol. 685, No. pp. 245-52, 1994.
Barabasi, A.-L., et al., Network Medicine: A Network-based Approach to Human Disease, Nat Rev Genet., vol. 12, No. 1, pp. 56-58, 2011.
Barrett, C.J., et al., "Problems, possibilities, and pitfalls in studying the arterial baroreflexes'influence over long-term control of blood pressure", American Journal of Physiology Regulatory Integrative and Comparative Physiology, vol. 288, No. 4, pp. R837-R845, 2005.
Bartfai, T., et al., Drug targets: single-cell transcriptomics hastens unbiased discovery;, Trends Pharmacol Sci, vol. 33, No. 1, pp. 9-16, 2012.
Bernstein, B.E., et al., "An integrated encyclopedia of DNA elements in the human genome", Nature, vol. 489, No. 7414, 57-74, 2012a and 2012b.
Bhajun, R., et al., "A statistically inferred microRNA network identifies breast cancer target miR-940 as an actin cytoskeleton regulator", Scientific Reports, vol. 5, No. 8336, 14 pages, 2015.
Biancardi, V.C., et al., "Circulating angiotensin II gains access to the hypothalamus and brain stem during hypertension via breakdown of the blood-brain barrier", Hypertension, vol. 63, No. 3, pp. 572-579, 2014.

(Continued)

*Primary Examiner* — Amy H Bowman
(74) *Attorney, Agent, or Firm* — Cozen O'Connor

(57) ABSTRACT

Therapeutic compositions and methods of treatment of the central nervous system, specifically towards hypertension comprising administration of a therapeutic comprising an anti-miR-135a, an anti-miR-miR-376a, or a combination, in the central nervous system effectively attenuates hypertension for up to four weeks provided a single administration.

3 Claims, 21 Drawing Sheets

(56) References Cited

OTHER PUBLICATIONS

Figure 1:
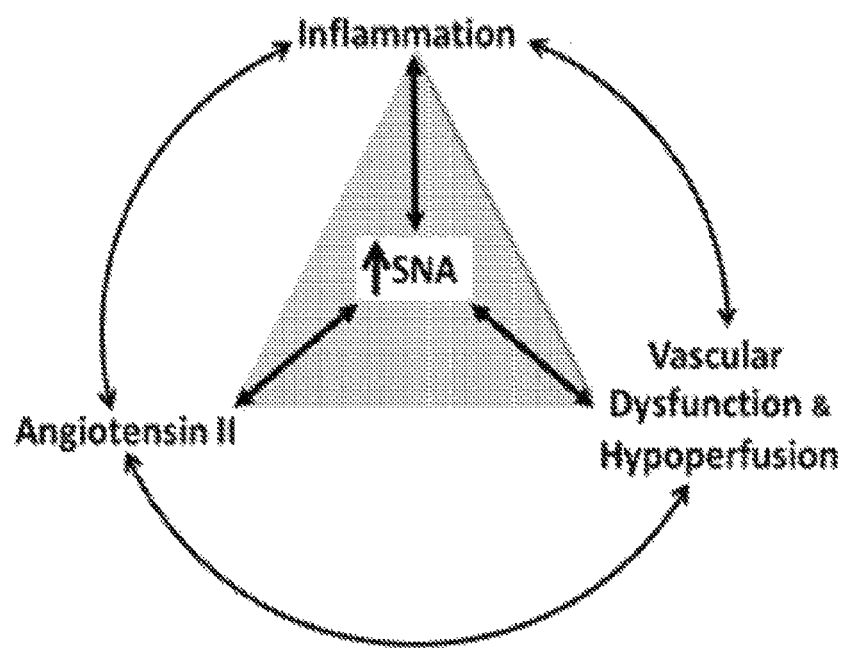

Bird, L., "Neuroimmunology: MicroRNAs keep microglia quiet", Nature Reviews Neuroscience, vol. 12, No. 2, p. 61, 2011.
Breving, K., et al., "complexities of microRNA regulation mirandering around the rules", The International Journal of Biochemistry & Cell Biology, vol. 42, No. 8, pp. 316-329, 2010.
Brody, M.J., et al., "Central nervouse system and the pathogenesis of hypertension. Sites and mechanisms", Hypertension, vol. 18, 5 Suppl, III7-12, 1991.
Brooks, V.L., et al., "Pressure to change? Re-evaluating the role of baroreceptors in the long-term control of arterial pressure", American Journal of Physiology Regulatory Integrative and Comparative Physiology, vol. 288, No. 4, pp. R815-R818, 2005.
Bugenhagen, S.M., et al., "Identifying physiological origins of baroreflex dysfunction is salt-sensitive hypertension in the Dahl SS rat", Physiol Genomics, vol. 42, pp. 23-41, 2010.
Butovsky, O., et al., "Targeting miR-155 restores abnormal microglia and attenuates disease in SOD1 mice", Annals of Neurology, vol. 77, No. 1, pp. 75-99, 2015.
Caldeira, C., et al., "Microglia change from a reactive to an age-like phenotype with the time in culture", Frontiers in Cellular Neuroscience, 8, Article 152, 16 pages, 2014.
Campagnole-Santos, M.J., et al., "Baroreceptor Reflex Modulation by Angiotensin II at the Nucleus Tractus Solitarii", Hypertension, vol. 11, Suppl I, No. 2, 1988.
Campbell, D.J., et al., "Angiotensin peptides in spontaneously hypertensive and nomotensive Donryu rats", Hypertension, vol. 25, No. 5, pp. 928-934, 1995.
Carmignoto, G., et al., "The contribution of astrocyte signalling to neurovascular coupling", Brain Research Reviews, vol. 63, Nos. 1-2, pp. 138-148, 2010.
Carroll, G.C., "Blood pressure monitoring", Critical Care Clinics, vol. 4, No. 3, pp. 411-434, 1988.
Carthy, E.R., "Autonomic dysfunction in essential hypertension: A systematic review" Annals of Medicine and Surgery, vol. 3, No. 1, pp. 2-7, 2014.
Casto, R., et al., "Cardiovascular actions of microinjections of angiotensin II in the brain stem of rats", The American Journal of Physiology, vol. 246, No. 5, Pt 2, pp. R811-R816, 1984.
Chan, Y.S., et al., "Relationship of rostral ventrolateral medullary neurons and angiotensin in the central control of blood pressure", Biological Signals, vol. 4, No. 3, pp. 133-141, 1995.
Chao, C.C., et al., "Interleukin-1 and Tumor Necrosis Factor-α Synergistically Mediate Neurotoxicity: Involvement of Nitric Oxide and of N-Methyl-D-aspartate Receptors", Brain, Behavior, and Immunity, vol. 9, No. 4, pp. 355-365, 1995.
Charchar, F.J., et al., "Whole Genome Survey of Copy Number Variation in the Spontaneously Hypertensive Rat", Hypertension, vol. 55, pp. 1231-1238, 2010.
Chen, W., et al., "Regulations of Drosophila circadian rhythms by miRNA let-7 is mediated by a regulatory cycle", Nature Communications, vol. 5, Article 5549, 2014.
Chen, W.-X., et al., "Implication of miRNAs for inflammatory bowel disease treatment: Systematic review", World Journal of Gastrointestinal Pathophysiology, vol. 5, No. 2, pp. 63-70, 2014.
Chen, J., et al., "MiR-17-6p as circulating biomarkers for the severity of coronary atherosclerosis in coronary artery disease", International Journal of Cardiology, vol. 197, pp. 123-124, 2015.
Cho, D.Y., "Chapter 5: Network Biology Approach to Complex Diseases", PLoS Computational Biology, vol. 8, No. 12, e1002820, 11 pages, 2012.
Chobanian, A.V, et al., "Seventh report of the Joint National Committee on Prevention, Detection, Evaluation, and Treatment of High Blood Pressure", Hypertension, vol. 42, No. 6, pp. 1206-1252, 2003.
Chu, Y.-Y., et al., "Astrocytic CCAAT/Enhancer Binding Protein δ Regulates Neuronal Viability and Spatial Learning Ability via miR-135a", Molecular Neurobiology, vol. 53, pp. 4173-4188, 2016.
Clark, P.M., et al., "Argonaute CLIP-Seq reveals miRNA targetome diversity across tissue types", Scientific Reports, vol. 4, No. 5947, 11 pages, 204.
Coca, A., et al., "Relationship between systolic blood pressure and mortality in patients with severe cognitive impairment", Journal of Hypertension, vol. 34, No. 4, pp. 632-633, 2016.
Cui, C., et al., "Transcriptional regulation of gene expression by microRNAs as endogenous decoys of transcription factors", Cellular Physiology and Biochemistry, vol. 33, No. 6, pp. 1698-1714, 2014.
Cui, J.G., et al., "Differential regulation of interleukin-1 receptor-associated kinase-1 (IRAK-1) and IRAK-2 by microRNA-146a and NF-kappaB in stressed human astroglial cells and in Alzheimer disease", The Journal of Biological Chemistry, vol. 285, No. 50, pp. 38951-38960, 2010.
Dampney, R., et al., "Role of Angiotensin II Receptors in the Regulation of Vasomotor Neurons in the Ventrolateral Medulla", Clinical and Experimental Pharmacology and Physiology, vol. 29, Nos. 5-6, pp. 467-472, 2002.
Dampney, R.A., et al., "Functional organization of brain pathways subserving the baroreceptor reflex: studies in conscious animal using immediate early gene expression", Cell Molecular Neurobiology, vol. 23, Nos. 4-5, pp. 597-616, 2003.
Decicco, D., Schwaber, J.S., Vadigepalli, R., Shifting the treatment paradigm in hypertension: micoRNAs as new CNS potential drug targets in essential hypertension.
Decicco, D., et al., "microRNA Network Changes in the Brainstem Underlie the Development of Hypertension", Physiological Genomics, vol. 47, No. 9, pp. 388-399, 2015.
De Geyter, D., et al., "Spontaneously hypertensive rats display reduced microglial activation in response to ischemic stroke and lipopolysaccharide", Journal of Neuroinflammation, vol. No. 114, 12 pages, 2012.
De Jong, W., et al., "Centrally induced hypotension and bradycardia after adminstration of alpha-methylnoradrenaline into the area of the nucleus tractus solitarii of the rat", British Journal of Pharmacology, vol. 58, No. 4, pp. 593-598, 1976.
Dhurjati, P., et al., "Systems Biology the Synergistic Interplay between Biology and Mathematics", The Canadian Journal of Chemical Engineering, vol. 86, pp. 127-141, 2008.
Doggrell, S.A., et al., "Rat models of hypertension, cardiac hypertrophy and failure", Cardiovascular Research, vol. 39, pp. 89-105, 1998.
Dolan, E., et al., "Comparing the therapeutic merits of angiotensin receptor blockers", Journal of Hypertension, vol. 34, No. 6, pp. 1052-1054, 2016.
Dumas, M., et al., "Gender differences in hypertension: myths and reality", Current Hypertension Reports, vol. 15, No. 4, pp. 321-330, 2013.
Duale, H., et al., "Restraining influence A2 neurons in chronic control of arterial pressure in spontaneously hypertensive rats", Cardiovascular Research, vol. 76, No. 1, pp. 184-193, 2007.
Duerrschmid, C., et al., "TNF Receptor 1 Signaling is Critically Involved in Mediating Angiotesin-II-induced Cardiac Fibrosis", J Mol Cell Cardiol, vol. 57, pp. 59-67, 2013.
Dvinge, H., et al., "The shaping and functional consequences of the microRNA landscape in breast cancer", Nature, vol. 497, No. 7449, pp. 378-382, 2013.
Dweep, H., et al., "miRWalk—Database: Prediction of possible miRNA binding sites by "walking" the genes of three genomes", Journal of Biomedical Informatics, vol. 44, No. 5, pp. 839-847, 2011.
Dweep, H., et al., "miRWalk 2.0: a comprehensive atlas of microRNA-target interactions",Nature Methods, vol. 12, No. 8, p. 697, 2015.
Erbes, T., et al., "Feasibility of urinary microRNA detection in breast cancer patients and its potential as an innovative non-invasive biomarker", BMC Cancer, vol. 15, No. 193, 9 pages.
Esler, M., "The 2009 Carl Ludwig Lecture: Pathophysiology of the human sympathetic nervous system in cardiovascular diseases: the transition from mechanisms to medical management", Journal of Applied Physiology (Bethesda, Md.: 1985), vol. 108, No. 2, p. 227-237, 2010.

(56) References Cited

OTHER PUBLICATIONS

Espina, V., et al., "Laser-capture microdissection", Nature Protocols, vol. 1, pp. 586-603, 2006.
Farh, K., et al., "The Widespread Impact of Mamalian MicroRNAs on mRNA Repression and Evolution", vol. 310, No. 5755, pp. 1817-1821, 2005.
Farooq, U., et al., "2014 Guideline for the Management of High Blood Pressure (Eighth Joint National Committee): Take-Home Messages", The Medical Clinics of North America, vol. 99, No. 4, pp. 733-738, 2015.
Fisher, J.P., et al., "The sympathetic nervous system and blood pressure in human: implications for hypertension", Journal of Human Hypertension, vol. 26, No. 8, pp. 463-475, 2012.
Fragoso, J.M., et al., "Interleukin 1 receptor antagonist polymorphisms are associated with the risk of developing acute coronary syndrome in Mexicans", Immunology Letters, vol. 133, No. 2, pp. 106-111, 2010.
Freilich, R.W., et al., "Integrated expression profiles of mRNA and miRNA in polarized primary murine microglia", PloS One, vol. 8, No. 11, e79416, 15 pages, 2013.
Gaiteri, C., et al., "Beyond modules and hubs: the potential of gene coexpression networks for investigating moleuclar mechanisms of complex brain disorders", Genes, Brain and Behavior, vol. 13, pp. 13-24, 2014.
Go, A.S., et al., "Executive summary: heart disease and stroke statistics—2014 update: a report from the American Heart Association", Circulation, vol. 129, No. 3, pp. 399-410, 2014.
Gonsalves, C.S., et al., "Hypoxia-Mediated Expression of 5-Lipoxygenase-Activating Protein Involves HIF-I β and NF-κB and MicroRNAs 135a and 199a-5p", The Journal of Immunology, vol. 184, pp. 3878-3888, 2010.
Gouraud, S.S., et al., "Increased anti-apoptotic conditions in the nucleus tractus solitarii of spontaneously hypertensive rat", Autonomic Neuroscience: Basic & Clinical, vol. 162, Nos. 1-2, pp. 15-23, 2011.
Guyenet, P.G., "The sympathetic control of blood pressure", Nature Reviews Neuroscience, vol. 7, No. 5, pp. 335-346, 2006.
Hartmann, H., et al., "miR-124 disinhibits neurite outgrowth in an inflammatory environment", Cell and Tissue Research, vol. 362, No. 1, pp. 9-20, 2015.
Head, G.A., et al., "Angiotensin and baroreflex control of the circulation", Brazilian Jouranl of Medical and Biological Research, vol. 35, No. 9, pp. 1047-1059, 2002.
Marvar, P.J., et al., "Systemic leukotriene b4 receptor antagonism lowers arterial blood pressure and improves autonomic function in the spontaneously hypertensive rat", The Journal of Physiology, vol. 594.20, pp. 5978-5989, 2016.
Hoffman, W.E., et al., "Evidence for direct neuronal stimulation by intraventricular angiotensin II", Brain Reseach, vol. 126, No. 2, pp. 376-381, 1977.
Huang, T., et al., "Wnt1-cre-mediated conditional loss of Dicer results in malformation of the midbrain and cerebellum and failure of neural crest and dopaminergic differentiation in mice", Journal of Molecular Cell Biology, vol. 2, No. 3, pp. 152-163, 2010.
Huber, D.A., et al., "Altered regulation of the rostral ventrolateral medulla in hypertensive obese Zucker rats", Am J Physiol Heart Circ Physiol, vol. 301, pp. H230-H240, 2011.
Irigoyen, M.C., et al., "Barorelex control of sympathetic activity in experimental hypertension", Brazilian Journal of Medial and Biological Research, vol. 31, No. 9, pp. 1213-1220, 1998.
Iyer, A., et al., "MicroRNA-146a: a key regulator of astrocyte-mediated inflammatory response", PloS One, vol. 7, No. 9, e44789, 14 pages, 2012.
Jadhav, S.P., et al., "microRNA-200b modulates microglia-mediated neuroinflammation via the cJun/MAPK pathway", Journal of Neurochemistry, vol. 130, No. 3, pp. 388-401, 2014.
Janssen, H.L.A., et al., "Treatment of HCV Infection by Targeting MicroRNA", New England Journal of Medicine, vol. 368, No. 18, pp. 1685-1694, 2013.
Jimenez-Mateos, E.M., et al., "Silencing microRNA-134 produces neuroprotective and prolonged seizure-suppressive effects", Nat Med, vol. 18, No. 7, pp. 1087-1094, 2012.
Jovicic, A., et al., "Comprehensive expression analyses of neural cell-type-specific miRNAs identify new determinants of the specification and maintenace of neuronal phenotypes", The Journal of Neurosciene; The Official Journal of the Society for Neuroscience, vol. 33, No. 12, pp. 5127-5137, 2013.
Kearney, P.M., et al., "Global burden of hypertension: analysis of worldwide data", Lancet, vol. 365, No. 9455, pp. 217-223, 2005.
Kemp, J.R., et al., "Angiotensin II-regulated microRNA 483-3p directly targets multiple components of the renin-angiotensin systems", Journal of Molecular and Cellular Cardiology, vol. 75, pp. 25-39, 2014.
Kezdi, P., "Neurogenic control of the blood pressure in hypertension", Cardiologia, vol. 51, No. 4, pp. 193-203, 1967.
Knight, J., "Human chromosome 17 in essential hypertension", Annals of Human Genetics, vol. 67, Pt2, pp. 193-206, 2003.
Kontaraki, J.E., et al., "MicroRNA-9 and microRNA-126 expression levels in patients with essential hypertension: potential markers of target-organ damage", Journal of the American Society of Hypertension, vol. 8, No. 6, pp. 368-375, 2014.
Krakoff, L.R., et al., "2014 Hypertension Recommendations From the Eighth Joint National Committe Panel Members Raise Concerns for Elderly Black and Female Populations", Journal of the American College of Cardiology, vol. 64, No. 4, pp. 394-402, 2014.
Lee, H.-J., et al., "miR-7b, a microRNA up-regulated in the hypothalamus aftern chronic hyperosmolar stimulation, inhibits Fos translation", Proceedings of the National Academy of Sciences of the United States of America, vol. 103, No. 42, pp. 42, pp. 15669-15674, 2006a and 2006b.
Lehmann, S.M., et al., "An unconventional role for miRNA: let-7 activates Toll-like receptor 7 and causes neurodegeneration", Nature Neuroscience, vol. 15, No. 6, pp. 827-835, 2012.
Leung, A.A., et al., "Hypertension Canada's 2016 Canadian Hypertension Education Program Guidelines for Blood Pressure Measurement, Diagnosis, Assessment of Risk, Prevention, and Treatment of Hypertension". Canadian Journal of Cardiology, vol. 32, No. 5, pp. 569-558, 2016.
Levy, J., et al., "Nonadherence to Recommended Guidelines for Blood Pressure Measurement", The Journal of Clinical Hypertension, vol. 18, No. 11, pp. 1157-1161, 2016.
Li, Y.-W., et al., "Angiotensin II excites vasomotor neurons but not respiratory neurons in the rostral and caudal ventrolateral medulla", Brain Research, vol. 577, No. 1, pp. 161-164, 1992.
Li, Y.-W., et al., "Expression of c-fos protein in the medulla oblongata of conscious rabbits in response to baroreceptor activation", Neuroscience Letters, vol. 144, Nos. 1-2, pp. 70-74, 1992.
Lin, L.-H., et al., "Astrocytes in the rat nucleus tractus solitarii are critical for cardiovascular reflex control", The Jounal of Neuroscience, vol. 33, No. 47, pp. 18608-18617, 2013.
Linsen, S.E.V., et al., "Small RNA expression and strain specificity in the rat", BMC Geomics, vol. 11, No. 249, 11 pages, 2010.
Liu, C.-G., et al., "Micro-RNA-135a and -200b, potontial Biomarkers for Alzheimer's disease, regulate β secretase and amyloid precursor protein", Brain Research, vol. 1583, pp. 55-64, 2014.
Lohmeiter, T.E., et al., "Chronic activation of the baroreflex and the promise for hypertension therapy", Handbook of Clinical Neurology, vol. 117, pp. 395-406, 2013.
Long, G., et al., "Circulating miR-30a, miR-126 and let-7b as biomarker for ischemic stroke in humans", BMC Neurology, vol. 13, No. 178, 10 pages, 2013.
Malmevik, J., et al., "Identification of the miRNA targetome in hippocampal neurons using RIP-seq", Scientific Reports, vol. 5, No. 12609, 13 pages, 2015.
Marques, F.Z., et al., "Neurogenic hypertension: revelations from genome-wide gene expression profiling" Current Hypertension Reports, vol. 14, No. 6, pp. 485-491, 2012.
Marques, F.Z., et al., "The emerging role of non-coding RNA in essential hypertension and blood pressure regulation" Journal of Human Hypertension, vol. 29, No. 8, pp. 459-467, 2015.

(56) References Cited

OTHER PUBLICATIONS

Vanhala, M., et al., "Proinflammation and hypertension: a population-based study", Mediators of Inflammation, vol. 2008, No. 619704, 7 pages, 2008.
Mehta, G., et al., "Cracking the ENCODE: from transcription to therapeutics", Hepatology, vol. 57, No. 6, pp. 2535-2535, 2013.
Messerli, F.H., et al., "Should We SPRINT Toward New Blood Pressure Goals or Let the Dust Settle?", The American Journal of Medicine, vol. 129, No. 8, pp. 769-770, 2016.
Miller, G.M., et al., "Robust dynamic balance of AP-1 transcription factors in a neuronal gene regulatory network", BMC Systems Biology, vol. 4, No. 171, 17 pages, 2010.
Miranda, K.C., et al., "A pattern-based method for the identification of MicroRNA binding sites and their corresponding heteroduplexes", Cell, vol. 126, No. 6, pp. 1203-1217, 2006.
Mishima, T., et al., "RT-PCR-based analysis of microRNA (miR-1 and -124) expression in mouse CNS", Brain Research, vol. 1131, No. 1, pp. 37-43, 2006.
Morgan, C. P., et al., "Sex differences in microRNA regulation of gene expression: no smoke, just miRs", Biology of Sex Differences, vol. 3, No. 22, 9 pages, 2012.
Morris, B. J., et al., "Brainstem microRNAs implicated in hypertension", Physiological Genomics, vol. 47, pp. 386-387, 2015.
Mozaffarian, D., et al., "Heart disease and stroke statistics-2015 update: a report from the American Heart Association", Circulation, vol. 131, No. 4, pp. 434-441, 2015.
Murphy, S.J., et al., "Sex-differences in microRNA expression during development in rat cortex", Neurochemistry International, vol. 77, pp. 24-32, 2014.
Ørom, U. A., et al., "MicroRNA-10a binds the 5'UTR of ribosomal protein mRNAs and enhances their translation", Molecular Cell, vol. 30, No. 4, pp. 460-471, 2008.
Pagani, M., et al., "Autonomic dysregulation in essential hypertension: insight from heart rate and arterial pressure variability", Autonomic Neuroscience: Basic & Clinical, vol. 90, Nos. 1-2, pp. 76-82, 2001.
Papademetriou, V., et al., "Difficult-to-Treat or Resistant Hypertension: Etiology, Pathophysiology, and Innovative Therapies", International Journal of Hypertension, vol. 2011, Article 438198, 4 pages, 2011.
Park, J., et al., "Inputs drive cell phenotype variability", Genome Research, vol. 24, pp. 930-941, 2014.
Pasquinelii, A.E., "MicroRNAs and their targets: recoonition regulation and an emerging reciprocal relationship", Nature Reviews Genetics, vol. 13, No. 4, pp. 271-282, 2012.
Paton, J.F., et al., "Response properties of baroreceptive NTS neurons", Annals of the New York Academy of Sciences, vol. 940, No. 1, pp. 157-168, 2001.
Paton, J.F.R., et al., "Signalling across the blood brain barrier by angiotensin II: novel implications for neurogenic hypertension", Journal of Molecular Medicine, vol. 86, No. 6, pp. 705-710, 2008.
Paton, J.F.R., et al., "Is neurogenic hypertension related to vascular inflammation of the brainstem?", Neuroscience and Biobehavioral Reviews, vol. 33, No. 2, pp. 89-94, 2009.
Paul, M., et al., "Physiology of local renin-angiotensin systems", Physiological Review, vol. 86, No. 3, pp. 747-803, 2006.
Peng, B., et al., "MicroRNA-200b targets CREB1 and suppresses cell growth in human malignant glioma", Molecular and Cellular Biochemistry, vol. 379, Nos. 1-2, pp. 51-58, 2013.
Pires, P.W., et al., "The effects of hypertension on the cerebral circulation", American Journal of Physiology Heart and Circulatory Physiology, vol. 304, No. 12, pp. H1598-H1614, 2013.
Place, R.F., et al., "MicroRNA-373 induces expression of genes with complementary promoter sequences", Proceedings of the National Academy of Sciences of the United States of America, vol. 105, No. 5, pp. 1608-1613, 2008.
Ponomarev, E.D., et al., "MicroRNA-124 promotes microglia quiescence and suppresses EAE by deactivating macrophages via the CE/EBP-α-PU.1 pathway", Nature Medicine, vol. 17, No. 1, pp. 64-70, 2011.
Ponomarev, E.D., et al., "MicroRNAs are universal regulators of differentiation, activation, and polarization of microglia and macrophages in normal and diseased CNS", Glia, vol. 61, No. 1, pp. 91-103, 2013.
Pravenec, M., et al., "Recent progress in the genetics of spontaneously hypertensive rats", Physiological Research, vol. 63, Suppl 1, pp. S1-S8, 2014.
Pusic, A.D., et al., "Youth and environmental enrichment generate serum exosomes containing miR-219 that promote CNS myelination", Glia, vol. 62, No. 2, pp. 284-299, 2014.
Rekker, K., et al., "Circulating miR-200-family micro-RNAS have altered plasma levels in patients with endometriosis and vary and blood collection time", Fertility and Sterility, vol. 104, No. 4, pp. 938-946e2.2015.
Rogerss, R.F., et al., "NTS neuronal responses to arterial pressure and pressure changes in the rat", vol. 265, No. 6, pp. R1355-R1368, 1993.
Rom, S., et al., "miR-98 and let-7g* protect the blood-brain barrier under neuroinflammatory conditions", Journal of Cerebral Blood Flow and Metabolism, vol. 35, pp. 1957-1965, 2015.
Ruilope, L.M., "SPRINT. Counteracting the risk of prehypertension?", Journal of the American Society of Hypertension, vol. 10, No. 7, pp 546-547, 2016.
Sacks, A.H., "Indirect blood pressure measurements: a matter of interpretation", Angiology, vol. 30, No. 10, pp. 683-695, 1979.
Sanfilippo, P.G., et al., "Translating the ENCyclopedia of DNA Elements Project findings to the clinic: ENCODE's implications for eye disease", Clinical & Experimental Ophthalmology, vol. 41, No. 1, pp. 78-83, 2013.
Sapru, H.N., at al., "Modification of aortic baroceptor resetting in the spontaneously hypertensive rat", American Journal of Physiology, vol. 230, No. 3, pp. 664-674, 1976.
Schaefer, A., et al., "Cerebellar neurodegeneration in the absence of microRNAs", The Journal of Experimenta Medicine, vol. 204, No. 7, pp. 1553-1558, 2007.
Schmiedel, J.M., at al., "Gene expression, MicroRNA control of protein expression noise", Science, vol. 348, No. 6230, pp. 128-132, 2015.
Sempere, L.F., et al., "Expression profiling of mammalian microRNAs uncovers a substet of brain-expressed microRNAs with possible roles in murine and human neuronoal differenatation", Genome Biology, vol. 5, No. 3, Article R13, pp. R13-R13.11, 2004.
Senanayake. P.D., "Increaed expression of angiotensin peptides in the brain of transgenic hypertensive rats", Peptides, vol. 15, No. 5, pp. 919-926, 1994.
Sesso, H.D., et al., "Systolic and diastolic blood pressure, pulse pressure, and mean arterial pressure as predictors of cardiovascular disease risk in Men", Hypertension, vol. 36, No. 5, pp. 801-807, 2000.
Shang, Q., et al., "Effects of high salt diet on NF-KB and CREB DNA binding activity in heart, kidney and hypothalamus of SHR", The FASEB Journal, vol. 23, No. 1 Supplement, 2009.
Shen, X.Z., et al., "Microglia Participate in Neurogenic Reulation of Hypertension", Hypertension, vol. 66, No. 2, pp. 309-316, 2015.
Shi, P., et at., "Brain microglial cytokines in neurogenic hypertension", Hypertension, vol. 56, No. 2, pp. 297-303, 2010.
Shi, P., et al., "Brain cytokines as neuromodulators in cardiovascular control", Clinical and Experimental Pharmacology & Physiology, vol. 37, No. 2, pp. e52-e577, 2010.
Sóber, S., et al., "MicroRNAs miR-124 and miR-135a are potential regulators of the mineralocorticoid receptor gene (NR3C2) expression", vol. 391, No. 1, pp. 727-732, 2010.
Sokol, N.S., et al., "Drosophila let-7 microRNA IS required for remodeling of the neuromuscalature during metamorphosis" Genes & Development, vol. 22, No. 12, pp. 1591-1596, 2008.
Streit, W.J., et al., "Microglia and neuroinflammation: a pathological perspective", Journal of Neuroinflammation, vol. 1, No. 14, 4 pages, 2004.
Sun, L., et al., "Inflammation of different tissues in spontaneously hypertensive rats", Acta Physiologica Sinica, vol. 58, No. 4, pp. 318-323, 2006.
Svahn, A.J., et al., "miR-124 Contributes to the functional maturity of microglia", Developmenta Neurobiology, 12 pages, 2015.

(56) References Cited

OTHER PUBLICATIONS

Talman, W.T., et al., "Chronic lability of arterial pressure produced by destruction of A2 catecholaminergic neurons in rat brainstem", Circulation Research, vol. 46, No. 6, pp. 842-853, 1980.
Tao, J., et al., "Deletion of astroglial Dicer causes non-cell-autonomous neuronal dysfunction and degernation", The Journal of Neuroscience, vol. 31, No. 22, pp. 8306-8319, 2011.
Tarassishin, L., et al., "Interferon regulatory factor 3 inhibits astrocyte inflammatory gene expression through suppression of the proinflammatory miR-155 and miR-155*", Glia, vol. 59, No. 12, pp. 1911-1922, 2011.
The ENCODE (ENCyclopedia of DNA Elements) Project. (2004). Science (New York, N.Y.), 306(5696), 636-40.
Thrasher, T.N., "Baroreceptors and the long-term control of blood pressure", Experimental Physiology, vol. 89, No. 4, pp. 331-341, 2004.
Thrasher, T.N., "Baroreceptors, baroreceptor unloading, and the long-term control of blood pressure", American Journal of Physiology Regulatory Integrative and Comparative Physiology, vol. 288, No. 4, pp. R819-R827, 2005.
Ueno, M., et al., "Blood-brain barrier disruption in the hypothalamus of young adult spontaneously hypertensive rats", Histochemistry and Cell Biology, vol. 122, No. 2, pp. 131-137, 2004.
Ueno, M., et al., "Blood-brain barrier is impaired in the hippocampus of young adult spontaneously hypertensive rats", Acta Neuropathologica, vol. 107, No. 6, pp. 532-538, 2004.
VadigePalli, R., et al., "Adaptive transcriptional dynamics of A2 neurons and central cardiovascular control pathways", Experimental Physiology, vol. 97, No. 4, pp. 462-468, 2012a and 2012b.
Van Zwieten, P.A., "Centrally Induced Hypotension by 2-(2,6-Dichlorophenyl)-5,6-Dihydroimidazo (2, 1-b)-Thiazole Fumarate (Compound 44-549)", Pharmacology, vol. 13, No. 4, pp. 352-355, 1975.
Van Zwieten, P.A., "The renaissance of centrally acting antihypertensive drugs", Journal of Hypertension, vol. 17, No. 3, pp. S15-S21, 1999.
Veerasingham, S.J., et al., "Brain renin-angiotensin system dysfunction in hypertension: recentadvances and perspectives", British Journal of Pharmacology, vol. 139, pp. 191-202, 2003.
Von Lueder, T.G., et al., "RAAS inhibitors and cardiovascular protection in large scale trials", Cardiovascular Drugs and Therapy, vol. 27, No. 2, pp. 171-179, 2013.
Von Lueder, T. G., et al., "Renin-angiotensin blockade combined with natriuvetic peptide system augmentation: novel therapeutic concepts to combat heart failure", Circulation Heart Failure, vol. 6, No. 3, pp. 594-605, 2013.
Waki, et al., "Specific inflammatory condition in nucleus tractus solatarii of the SHR: novel insight for neurogenic hypertension?", Autonomic Neuroscience: Basic & Clinical, vol. 142, Nos. 1-2, pp. 25-31, 2008.
Waki, H., et al., "Evidence of specific inflammatory condition in nucleus tractus solitarii of spontaneously hypertensive rats", Experimental Physiology, vol. 95, No. 5, pp. 595-600, 2010a and 2010b.
Waki, H., et al., "Contributions of vascualr inflammation in the brainstem for neurogenic hypertension", Respiratory Physiology & Neurobiology, vol. 178, No. 3, pp. 422-428, 2011.
Waki, H., et al., Excessive leukotriene B4 in nucleus tractus solitarii is prohypertensive in spontaneously hypertensive rats, Hypertension, vol. 6, No. 1, pp. 194-201, 2013a and 2013b.
Wang, F., et al., "Plasma microRNA-133a is a new marker for both acute myocardial infarction and underlying coronary artery stenosis", Journal of Translational Medicine, vol. 11, No. 222, 9 pages, 2013.
Wehrwein, E.A., et al., "Regulation of blood pressure by the arterial baroreflex and autonomic nervous system", Handbook of Clinical Neurology, vol. 117, pp. 89-102, 2013.
Wei, C., et al., "Circulating miRNAs as potential marker for pulmonary hypertension", PloS One, vol. 8, No. 5, e64396, 9 pages, 2013.

Winkleweski, P.J., "Brain inflammation and hypertension; the chicken or the egg?", Journal of Neuroinflammation, vol. 12, No. 85, 7 pages, 2015.
Wolf-Maier, K., et al., "Hypertension treatment and control in five Euroepean countries, Canada, and the United States", Hypertension, vol. 43, No. 1, pp. 10-17, 2004.
Woodbury, M.E., et al., "miR-155 Is Essential for Inflammation-Induced Hippocampal Neurogenic Dysfunction", Journal of Neuroscience, vol. 35, No. 26, pp. 9764-9781, 2015.
Wu, K.L.H., et al., "Neuroinflammation and oxidative stress in rostral ventrolateral medulla contribute to neurogenic hypertension induced by systemic inflammation", Journal of Neuroinflammation, vol. 9, No. 212, 15 pages, 2012.
Xia, Z., et al., "Molecular dynamics simulations of Ago silencing complexes reveal a large repertoire of admissible "seed-less" targets", Scientific Reports, vol. 2, No. 569, 10 pages, 2012.
Zanutto, B.S., et al., "Neural set point for the control of arterial pressure: role of the nucleus tractus solitarius", BioMedical Engineering OnLine, vol. 9, No. 4, 13 pages, 2010.
Zhao, C., et al., "MicroRNA let-7b regulates neural stem cell proliferation and differentiation by targeting nuclear receptor TLX signaling", Proceedings of the National Academy of Sciences of the United States of America, vol. 107, No. 5, pp. 1876-1881, 2010.
Zhao, J., et al., Small RNAs control sodium channel expression, nociceptor excitability, and pain threshold. The Journal of Neuroscience, vol. 30, No. 32, pp. 10860-10871, 2010.
Zubcevic, J., Waki, H., Raizada, M. K., & Paton, J.F.R. (2011), Autonomic-immune-vascular interaction: and emerging concept for neurogenic hypertension, Hypertension, 57(6), 1026-1033.
Agarwal, D., et al., "Chronic exercise modulates RAS components and improves balance between pro-and anti-inflammatory cytokines in the brain of SHR", Basic Res Cardiol., vol. 106, No. 6, pp. 1069-1085, 2011.
Albert, R., et al., "Error and attack tolerance of complex networks", Nature, vol. 406, pp. 378-382, 2000.
Albert, R., et al., "Statistical mechanics of complex networks", Reviews of Modern Physics, Vo. 74, pp. 47-97, 2002.
Anderson, W., et al., "Molecular variability elicits a tunable switch with discrete neuromodulatory response phenotypes", J Comput Neurosci, vol. 40, pp. 65-82, 2016.
Baras, A.S., et al., "miRge—A Multiplexed Method of Processing Small RNA-Seq Data to Determine MicroRNA Entropy", PLOS One, DOI:10.1371/journal.pone.0143066, 16 pages, 2015.
Bartel, D.P., "MicroRNAs: Target Recognition and Regulatory Functions", Cell, vol. 136, pp. 215-233, 2009.
Baumann, M., et al., "Transient AT1 receptor-inhibition in prehypertensive spontaneously hypertensive rats results in maintained cardiac protection until advanced age", Journal of Hypertension, vol. 25, No. 1, pp. 207-215, 2007.
Billaud, M., et al., "Pannexin1 regulates α1-adrenoreceptor-mediated vasoconstriction", Circ Res., vol. 109, No. 1, pp. 80-85, 2011.
Bock, M., et al., "Hub-Centered Gene Network Reconstruction Using Automatic Relevance Determination", PLOS One, vol. 7, No. 5, Article e35077, 17 pages, 2012.
Burnier, M., M.D., "Blockade of the Renin-Angiotensin System and the Risk of Acute Kidney Injury", The Journal of Clinical Hypertension, vol. 18, No. 6, pp. 512-513, 2016.
Cai, S., et al., "Functional characteristics of a double negative feedback loop mediated by microRNAs", Cogn Neurodyn, vol. 7, pp. 417-429, 2013.
Casci, T., "The insulating role of an RNAi architect", Nature Reviews Genetics, vol. 7, pp. 664-665, 2006.
Chan, R.K.W., et al., "Organization and Transmitter Specificity of Medullary Neurons Activated by Sustained Hypertension: Implications for Understanding Baroreceptor Reflex Circuitry", The Journal of Neuroscience, vol. 18, No. 1, pp. 371-387, 1998.
Cline, M.S., et al., "Integration of biological networks and gene expression data using Cytoscape", Nat Protoc, vol. 2, No. 10, pp. 2366-2381, 2007.
Colombari, E., et al., "Role of the Medulla Oblongata in Hypertension", Hypertension, vol. 38 [part 2], pp. 549-554, 2001.

(56) References Cited

OTHER PUBLICATIONS

Czerwinska, U., et al., "DeDaL: Cytoscape 3 app for producing and morphing data-driven and structure-driven network layouts", BMC Systems Biology, vol. 9, No. 46, 11 pages, 2015.
Daviet, L., et al., "Cloning and Characterization of ATRAP, a Novel Protein That Interacts with the Angiotensin II Type 1 Receptor", The Journal of Biological Chemistry, vol. 274, No. 24, Issue of Jun. 11, pp. 17058-17062, 1999.
DeJima, T., et al., "Prepubertal angiotensin blockade exerts long-term therapeutic effect through sustained ATRAP activation in salt-sensitive hypertensive rats", Journal of Hypertension, vol. 29, No. 10, pp. 1919-1929, 2011.
Deng, Y-Q, et al., "Intranasal Administration of Lentiviral miR-135α Regulates Mast Cell and Allergen-Induced Inflammation by Targeting GATA-3", PLOS One, DOI:10.1371/journal.pone.0139322, 15 pages, 2015.
Dueck, H., et al., "Variation is function: Are single cell differences functionally important?", Bioessays, vol. 38, pp. 172-180, 2016.
Dvoriantchikova, G., et al., "Expression of pannexin family of proteins in the retina", FEBS Letters, vol. 580, pp. 2178-2182, 2006.
Ebert, M.S., et al., "Roles for MicroRNAs in Conferring Robustness to Biological Processes", Cell, vol. 149, pp. 515-524, 2012.
Eberwine, J., et al., "Single cell transcriptomics of hypothalamic warm sensitive neurons that control core body temperature and fever response signaling asymmetry and an extension of chemical neuroanatomy", Pharmacology & Therapeutics, vol. 129, pp. 241-259, 2011.
Enright, A.J. et al., "MicroRNA targets in Drosophila", Genome Biology, vol. 5, Issue 1, Article No. R1, 14 pages, 2003.
Ferrell, J.E., Jr., "Tripping the switch fantastic: how a protein kinase cascade can convert graded inputs into switch-like outputs", Trends in Biochemical Sciences 21, vol. 21, No. 12, pp. 460-466, 1996.
Ferrell, J.E. Jr., "Self-perpetuating states in signal transduction: positive feedback, double-negative feedback, and bistability", Current Opinion in Chemical Biology, vol. 6, pp. 140-148, 2002.
Flister, M.J., et al., "Identifying Multiple causative genes at a single GWAS locus", Genome Research, vol. 23, pp. 1996-2002, 2013.
Formosa, A., et al., "Micro-RNAs, miR-154, miR-299-5p, miR-376a, miR-376c, miR-377, miR-381, miR-487b, miR-485-3p, miR-495, and miR-654-3p, mapped to the 14q32.31 locus, regulate proliferation, apoptosis, migration and invasion in metastatic prostate cancer cells", Oncogene, vol. 33, pp. 5173-5182, 2014.
Gallego-Delgado, J., et al., "Proteomic Analysis of Early Left Ventricular Hypertrophy Secondary to Hypertenson: Modulation by Antihypertensive Therapies", Journal of the American Society of Nephrology, vol. 17, pp. S159-S164, 2006.
Gao, J., et al., "Target control of complex networks", Nature Communcations, vol. 5, Article No. 5415, 8 pages, 2014.
Geraldes, V., et al., "Essential role of RVL medullary neuronal activity in the long term maintenance of hypertension in conscious SHR", Autonomic Neuroscience: Basic and Clinical, vol. 186, pp. 22-31, 2014.
Goehler, L.E., et al., "Vagal Paraganglia Bind Biotinylated Interleukin-1 Receptor Antagonist: A Possible Mechanism for Immune-to-Brain Communication", Brain Research Bulletin, vol. 43, No. 3, pp. 357-364, 1997.
Granata, a.R., et al., "Brain stem area with C1 epinephrine neurons mediates baroreflex vasodepressor responses", Am. J. Physiol. (Heart Circ. Physiol. 17), vol. 248, p. H547-H567, 1985.
Gu, S., et al., "RGS proteins: identifying new GAPs in the understanding of blood pressure regulation and cardiovascular function", Clinical Science, vol. 116, pp. 391-399, 2009.
Guo, L., et al., "A Comprehensive Analysis of miRNA/isomiR Expression with Gender Difference", PLOS One, vol. 11, No. 5, Article No. e0154955, 12 pages, 2016.
Hartung, T., "Thoughts on limitations of animal models", Parkinsonism & Related Disorders, vol. 14, pp. S81-S83, 2008.
Hemmisi, K., et al., "miR-135α Inhibits Cancer Stem Cell-Driven Medulloblastoma Development by Directly Repressing Arhgef6 Expression", Stem Cells, vol. 33, pp. 1377-1389, 2015.

Hirooka, Y., et al., "Role of angiotensin II receptor subtypes in mediating the sympathoexcitatory effects of exogenous and endogenous angiotensin peptides in the rostral ventrolateral medulla of the rabbit", Brain Research, vol. 772, pp. 107-114, 1997.
Iriuchijima, J., Proceedings: 115. Sympathetic tone in the spontaneously hypertensive rat, Nihon Seirigaku Zasshi, vol. 35, No. 8, p. 430, Aug.-Sep. 1973.
Jin, W., et al., "Small RNA Sequencing Reveals MicroRNAs That Modulate Angiotensin II Effects in Vascular Muscular Cells", The Journal of Biological Chemistry, vol. 287, No. 19, pp. 15672-15680, 2012.
Johnston, R.J., et al., "MicroRNAs acting in a double-negative feedback loop to control a neuronal cell fate decision", PNAS, vol. 102, No. 35, pp. 12449-12454, 2005.
Khan, R.L., et al., "Dynamic transcriptomic response to acute hypertension in the nucleus tractus solitarius", Am J Physiol Regul Integr Comp Physiol, vol. 295, pp. R15-R27, 2008.
Kim, J.K. et al., "Inferring the kinetics of stochastic gene expression from single-cell rNA-sequencing data", Genome . Biology, vol. 14, No. R7, 12 pages, 2013.
Krek, A., et al., "Combinatorial microRNA target predictions", Nature Genetics, vol. 37, No. 5, pp. 495-500, 2005.
Kroiss, A., et al., "Androgen-regulated micro-RNA-135a decreases prostrate cancer cell migration and invasion through downregulating ROCK1 and ROCk2", Oncogene, vol. 34, pp. 2846-2855, 2015.
Kuwahara, H., et al., "Bistability in feedback circuits as a byproduct of evolution of evolvability", Molecular Systems Biology, vol. 8, Article No. 564, 11 pages, 2012.
Lai, C.P.K., et al., "Pannexin2 as a novel growth regulator in C6 glioma cells", Oncogene, vol. 28, pp. 4402-4408, 2009.
Langfelder, P., et al., "When Is Hub Gene Selection Better than Standard Meta-Analysis?", PLOS One, vol. 8, No. 4, Article No. e61505, 16 pages, 2013.
Lapatas, V., et al, "Data integration in biological research: an overview", Journal of Biological Research-Thessaloniki, vol. 22, No. 9, 16 pages, 2015.
Lehner, B., et al., "Systematic mapping of genetic interactions in Caenorhabditis elegans identifies common modifiers of diverse signaling pathways", Nature Genetics, vol. 38, No. 8, pp. 896-903, 2006.
Li, W.Y., et al., "Circulating microRNAs as potential non-invasive biomarkers for the early detection of hypertension-related stroke", Journal of Human Hypertension, vol. 28, pp. 288-291, 2014.
Li, N., et al., "Activation of the cardiac proteasome promotes angiotension Ii-induced hypertrophy by down-regulation of ATRAP", Journal of Molecular and Cellular Cardiology, vol. 79, pp. 303-314, 2015.
Londin, E., et al., "Analysis of 13 cell types reveals evidence for the expression of numerous primate- and tissue-specific microRNAs", PNAS, pp. E1106-E1115, www.pnas.org/cgi/doi/10.1073/pnas.1420955112, 2015.
Lu, D., et al., "Angiotensin II-Induced Nuclear Targeting of the Angiotensin Type 1 (AT1) Receptor in Brain Neurons", Endocrinology, vol. 139, No. 1, pp. 365-375, 1998.
Ma, Q., et al., "Inhibition of microRNA-210 provides neuroprotection in hypoxic-ischemic brain injury in neonatal rats", Neurbiol Dis., vol. 89, pp. 202-212, 2016.
Makadia, H.K., et al., "Intracellular Information Processing through Encoding and Decoding of Dynamic Signaling Features", PLOS Computational Biology, vol. 11, No. 10, Article No. e1004563, 32 pages, 2015.
Margolin, A.A., et al., "ARACNE: An Algorithm for the Reconstruction of Gene Regulatory Networks in a Mammalian Cellular Context", BMC Bioinformatics, vol. 7(Suppl1), No. S7, 15 pages, 2006.
Marques, F.Z., et al., "Measurement of absolute copy number variation reveals association with essential hypertension", BMD Medical Genomics, vol. 7, No. 44, 8 pages,2014.
Masson, G.S., et al., "Aerobic training normalizes autonomic dysfunction. HMGB1 content, microglia activation and inflammation in hypothalamic paraventricular nucleus of SHR", Am J Physiol Heart Circ Physiol, vol. 309, pp. H1115-H1122, 2015.

(56) References Cited

OTHER PUBLICATIONS

Matsumoto, K., et al., "Genetic variability in SHR (SHRSR), SHRSP and WKY strains", Clin Exp Hypertens A, vol. 13, No. 5, pp. 925-938, 1991.
Michelini, L.C., Ph. D. "The NTS and Integration of Cardiovascular Control During Exercise in Normotensive and Hypertensive Individuals", Current Hypertension Reports, vol. 9, pp. 214-221, 2007.
Moreno, C., et al., "Genomic map of cardiovascular phenotypes of hypertension in female Dahl S rats", Physiol Genomics, vol. 15, pp. 243-257, 2003.
Morris, M.K., et al., "Construction of Cell- Type-Specific Logic Models of Signaling Networks using CellNopt", Computational Toxicology: vol. IL, Methods in Molecular Biology, vol. 930, Chapter 8, pp. 179-214, 2013.
Mukherji, U.A., et al., "MicroRNAs can generate thresholds in target gene expression", Nature Genetics, vol. 43, No. 9, pp. 854-860, 2011.
Muratani, H., et al., "Effect of Angiotensin II in ventrolateral medulla of spontaneously hypertensive rats", Regulatory, Integrative and Comparative Physiology, vol. 260, No. 5, pp. R977-R984, 1991.
Okaty, B.W., et al., "A Quantitative Comparison of Cell-Type-Specific Microarray Gene Expression Profiling Methods in the Mouse Brain", PLOS One, vol. 6, No. 1, Article No. e16493, 10 pages, 2011.
Opgen-Rhein, R., et al., "From correlation to causation networks: a simple approximate learning algorithm and its application to high-dimensional plant gene expression data", BMC Systems Biology, vol. 1, No. 37, 10 pages, 2007.
Oppermann, M., et al., "ATRAP Deficiency Increases Arterial Blood Pressure and Plasma Volume", J Am Soc Nephrol, vol. 21, pp. 468-477, 2010.
Oshita, A., et al., "Attenuation of Inflammatory Vascular Remodeling by Angiotensin II type 1 Receptor-Associated Protein", Hypertension, vol. 48, pp. 671-676, 2006.
Park, J., et al., "Identifying functional gene regulatory network phenotypes underlying single cell transcriptional variability", Progress in Biophysics and Molecular Biology, vol. 117, pp. 87-98, 2015.
Penuela, S., et al., "The biochemistry and function of pannexin channels", Biochimica et Biophysica Acta, vol. 1828 No. 1, pp. 15-22, 2013.
Pescador, N., et al., "Serum Circulating microRNA Profiling for Identification of Potential Type 2 Diabetes and Obesity Biomarkers", PLOS One, vol. 8, No. 10, Article No. e77251, 8 pages, 2013.
Pimenta, E., "Hypertension in women", Hypertension Research, vol. 35, pp. 148-152,2012.
Prokopec, S.D., et al., "Systematic evaluation of medium-throughput mRNA abundance platforms", RNA, vol. 19, pp. 51-62, 2013.
Ren, J-W, et al., "MiR-135 post-transcription regulates FOXO1 expression and promotes cell proliferation in human malignant melanoma cells", Int J Clin Exp Pathol, vol. 8, No. 6, pp. 6356-6366, 2015.
Rogers, R.F., et al., "Simultaneous Encoding of Carotid Sinus Pressure and dP/dt by NTS Target Neurons of Myelinated Baroreceptors", Journal of Neurophysiology, vol. 76, No. 4, pp. 2644-2660, 1996.
Saez-Rodriguez, J., et al., "Discrete logic modelling as a means to link protein signalling networks with functional analysis of mammalian signal transduction", Molecular Systems Biology, vol. 5, Article No. 331, 19 pages, 2009.
Saito, R., et al., "A travel guide to Cytoscape plugins", Nat Methods, vol. 9, No. 11, pp. 1069-1076, 2012.
Satoh, J-I, et al., "Molecular network analysis of human microRNA targetome: from cancers to Alzheimer's disease", Bio Data Mining, vol. 5, Article No. 17, 22 pages, 2012.
Smoot, M.E., et al., "Cytoscape 2.8: new features for data integration and network visualization", vol. 27, No. 3, pp. 431-432, 2011.
Spaethling, J.M., et al., "Serotonergic neuron regulation informed by in vivo single-cell transcriptomics", The FASEB Journal, vol. 28, pp. 771-780, 2014.
Spurgeon, S.L., et al., "High Throughput Gene Expression Measurement with Real Time PCR in a Microfluidic Dynamic Array", PLos One, vol. 3, No. 2, Article No. e1662, 7 pages, 2008.
Stoll, M., et al., "A Genomic-Systems Biology Map for Cardiovascular Function", Science, vol. 294, pp. 1723-1726, 2001.
Swayne. L.A., et al., "Connexins and pannexins in neuronal development and adult neurogenesis", BMC Cell Biology, vol. 17(Suppl 1), No. 10, pp. 39-49, 2016.
Takagishi, M., et al., "IL-6 microinjected in the nucleus tractus solitarii attenuates cardiac baroreceptor reflex function in rats", Am J Physiol Regul Integr Comp Physiol, vol. 298, pp. R183-R190, 2010.
Tang, F., et al., "RNA-Seq analysis to capture the transcriptome landscape of a single cell", Nat Protoc., vol. 5, No. 3, 34 pages, 2010.
Tay, S., "Single-Cell Analysis: The Differences That Kill", Cell, vol. 162, pp. 1208-1210, 2015.
Udenfriend, S., et al., "Spontaneously Hypertensive Rat", Science, vol. 176, No. 4036, pp. 1155-1156, 1972.
Ueno, K., et al., "Sex-related differences in pharmacokinetics and pharmacodynamics of anti-hypertensive drugs", Hypertension Research, vol. 35, pp. 245-250, 2012.
Vickers, A.J., "Whose data set is it anyway? Sharing raw data from randomized trials", Trials, vol. 7, No. 15, 6 pages, 2006.
Wang, H., et al., "Network analysis of microRNAs, transcription factors, target genes and host genes in nasopharyngeal carcinoma", Oncology Letters, vol. 11, pp. 3821-3828, 2016.
Wylie, A.D., et al., "Post-transcriptional regulation of wnt8a is essential to zebrafish axis development", Developmental Biology, vol. 386, pp. 53-63, 2014.
Yeruva, L., et al., "Early MicroRNA Expression Profile as a Prognostic Biomarker for the Development of Pelvic Inflammatory Disease in a Mouse Model of Chlamydial Genital Infection", mBio, vol. 5, No. 3, e01241-14,11 pages, 2014.
Yoshida, M., et al., "Analysis of genes causing hypertension and stroke in spontaneously hypertensive rats: Gene expression profiles in the brain", International Journal of Molecular Medicine, vol. 33, pp. 887-896, 2014.
Zhang, T., et al., "MiR-135a and MRP1 play pivotal roles in the selected lethality of phenethyl isothiocyanate to malignant glioma cells", Am J Cancer Res, vol. 6, No. 5, pp. 957-972, 2016.
Zheng, Y., et al., "miR-376a suppresses proliferation and induces apoptosis in hepatocellular carcinoma", FEBS Letters, vol. 586, pp. 2396-2403, 2012.
Zhao, H.B., "Expression and function of pannexins in the inner ear and hearing", BMC Cell Biology, vol. 17(Suppl 1), No. 16, pp. 121-126, 2016.
Zhou, W., et al., "MiR 135a promotes growth and invasion of colorectal cancer via metastasis suppressor 1 in vitro", Acta Biochem Biophys Sin, vol. 44, No. 10, pp. 838-846, 2012.

\* cited by examiner

US 10,982,214 B2

INHIBITING MICRORNA TO PREVENT DEVELOPMENT OF ESSENTIAL HYPERTENSION

CROSS REFERENCE TO RELATED APPLICATION

This application claims the benefit of U.S. Provisional Application Ser. No. 62/364,616, filed Jul. 20, 2016, the disclosure content of which is hereby incorporated by reference in its entirety.

GOVERNMENT SUPPORT

This invention was made with government support under HL111621 and GM083108 awarded by the National Institutes of Health. The Government has certain rights in the invention.

FIELD OF INVENTION

The present invention is generally related to pharmaceutical compositions and methods for treatment of hypertension and more broadly to development of central autonomic and development of brain dysfunctions. For example, through the use of anti-miR therapies to impact gene regulation in vivo, specifically towards hypertension.

BACKGROUND OF INVENTION

Essential hypertension is a major disease impacting millions across the globe. Hypertension is often resistant to current therapies, which can result in deadly consequences such as stroke and heart attack. One third of the United States population is hypertensive, and despite 75% using anti-hypertensive medication, only 53% have blood pressure controlled. Hypertensive patients typically exhibit autonomic dysfunction, and it is now compelling that neural contribution to hypertension is a major cause of its development and maintenance. A number of molecular pathways have been examined in the context of neural contribution to essential hypertension to study potentially significant impact on the hypertensive state, for example, some of the presently available therapies and drugs in development focus on Angiotensin II (Ang II) signaling and Leukotriene B4 (LTB4) signaling pathways.

However, despite protein signaling pathways being necessary for the development of disease, non-coding RNA, mainly through microRNA, regulation of such pathways has proven to be a key regulatory element in disease, yet effective regulation to control hypertension remains elusive.

Despite many advances in strategies to prevent or treat hypertension, cardiovascular disease remains the number one cause of death in the US according to the CDC and American Heart Association (Go et al.). The 2009 overall death rate from hypertension as a primary cause was 18.5 per 100,000, and hypertension direct and indirect cost exceeded 5 billion dollars in the US in 2009 (Go et al). Numerous strategies have already been employed in the search for a hypertension cure including Genome Wide Association Studies, carotid body ablation, small molecule inhibitors of various pathways and lifestyle modifications, yet ⅓ of all hypertensive people do not gave their blood pressure fully controlled.

SUMMARY OF INVENTION

We propose a different strategy to provide the etiology of neurogenic hypertension in order to develop more strategies to prevent or cure this disease. Functional genomics, which integrates different high-dimensional datasets obtained from transcriptomic, proteomic and genomic data, serves as a tool to understand the system-wide dynamics of this polygenic trait. A benefit of using functional genomics to study hypertension includes the myriad data already publicly available from which to probe for experimental hypotheses. Layering transcriptomic and proteomic data with GWAS studies, single nucleotide polymorphism data and quantitative locus analyses can improve our understanding of the cause of hypertension in more of a global manner. Combining all of these data is useful in characterizing hypertension, but viewing the data through gene or protein expression differences in hypertension compared to controls provides better targets for actually affecting the physiology. When performing transcript-level analysis in hypertension, it is critical that non-coding RNA like microRNAs and lncRNAs be accounted for to obtain a more complete picture of the molecular causes of hypertension. Furthermore, obtaining non-coding RNA molecular drivers for the disease of provide a straightforward path to a druggable target, as microRNAs can be manipulated with antisense oligonucleotide technology.

The process we have discovered and developed comprises two essential steps (1) Acquisition of high-throughput data revealing the broad pattern of small to modest gene expression and regulatory microRNA changes tracking development of a disease process, followed by computational analysis predicting the gene regulatory network and of the hub microRNAs driving it's changed behavior. (2) Design and application of therapeutic anti-microRNA agents for introduction to the system to prevent or remediate the disease state by restoring normal network function. Therefore, in the broadest sense, the methods described herein provide a unique gene regulating network implication one or more microRNA. By identification of implicated microRNA, therapeutic treatments can be utilized with anti-miR for remediation and regulation of system function.

In a preferred embodiment, the process comprises acquisition of high-throughput data; application of a therapeutic anti-microRNA that drives a changed behavior with regard to the blood pressure control system and the regulation of systemic blood pressure by manipulation of the system of the network of genes functionally relevant to neurogenic hypertension. Specifically, the anti-microRNA are anti-miR-376a-5p, an anti-miR-135a-5p In a further embodiment, a method comprises application to rebalancing of the function of the autonomic nervous system and its effect on organs. Hypertension is only one of a host of diseases in which sympathetic overdrive and reduced parasympathetic drive cause organ dysfunction (prominently heart failure, the single largest killer worldwide), and in which there is he opportunity to remediate these conditions by a rebalancing of these two autonomic outflows. In each case the approach would be to track the specific changing gene and microRNA activities in autonomic regulatory structures relevant in development and maintenance of that disease as targets for remediation.

In a preferred embodiment, a method of preventing or remediating development of any neurological disease process in which a specific time course of any duration, and a controlling neural system reflecting or driving the disease process, can be identified through the methods described herein.

A method to analyze the high-throughput data to identify hub microRNAs that participate in a disinhibition network in which negative regulators of signaling and metabolic pathways are targeted by the microRNAs to amplify the signaling and metabolic activity.

The anti-microRNA intervention targets and block the activity of such hub microRNAs to disinhibit the negative regulators of signaling and metabolic pathways, thus increasing the inhibition of these pathways, to rebalance the function of the autonomic nervous system. Our approach and methods are in direct contrast to the established and widely utilized therapeutic approaches that focus on single target and single mechanism and seek inhibitors for the signaling pathways directly and attempting to turn them off completely A particular embodiment of the invention is directed towards a pharmaceutical composition comprising an effective amount of an anti-miR-135a-5p.

A further embodiment is directed towards a pharmaceutical composition comprising an effective amount of an anti-miR-376a-5p.

A further embodiment is directed towards a pharmaceutical composition comprising an anti-miR-135a-5p and an anti-miR-376a-5p.

These compositions are suitable for therapeutic treatment in the methods and uses described herein, including, specifically for the treatment of hypertension.

A further embodiment is directed towards a method for treating hypertension comprising administering to a human patient an effective amount of any one of the pharmaceutical composition, comprising an anti-miR-376a-5p, an anti-miR-135a-5p, or combinations thereof.

A further embodiment is directed towards a method of treating hypertension comprising administering to a patient a pharmaceutical composition comprising an anti-miR, wherein said composition is effective in regulating PTGR1 expression in astrocytes by direct action on PTGR1 mRNA, thereby decreasing hypertension, wherein an anti-miR to miR-135a specifically decreases the levels of miR-135a, leading to an increase in the PTGR1 mRNA levels, and wherein the anti-miR are effective in reducing hypertension or preventing or reducing the likelihood of occurrence of essential hypertension.

A further embodiment is directed towards a method of treating hypertension comprising administering to a patient a pharmaceutical composition comprising an anti-miR, wherein said composition is effective in regulating AGTRAP expression in neurons by direct action on AGTRAP mRNA, wherein the anti-miR-376a thereby specifically decreases the levels of miR-376a, leading to an increase in the AGTRAP mRNA levels, and wherein the anti-miR to miR-376a specifically prevents development of hypertension or reduces the likelihood of occurrence of essential hypertension.

A further embodiment is directed towards a method of restoring normal network function to a patient comprising; analyzing a sample from a patient for gene expression and regulatory microRNA; predicting the gene regulatory network of the hub microRNA responsible for the network function; designing a therapeutic anti-microRNA to target the system; and restoring normal network function by administering to said patient.

In the embodiments herein, the specific anti-microRNA for treatment are selected from the group consisting of: miR-1, miR-100, miR-103, miR-107, miR-129, miR-130a, miR-132, miR-133a, miR-135a, miR-136, miR-139-5p, miR-142-3p, miR-144, miR-150, miR-151, miR-153, miR-15b, miR-16, miR-17-5p, miR-181, miR-181a, miR-181b+d, miR-181c, miR-185, miR-196b, miR-199a-3p, miR-199a-5p, miR-19a, miR-19b, miR-206, miR-20a+20b-5p, miR-21, miR-219-2-3p, miR-219-5p, miR-23b, miR-24, miR-25, miR-27b, miR-29a, miR-29b, miR-29c, miR-300-3p, miR-30a, miR-30b-5p, miR-322, miR-324-3p, miR-324-5p, miR-326, miR-329, miR-335, miR-337, miR-338, miR-340-3p, miR-342-5p, miR-344a-3p, miR-344b-1+2-3p, miR-345-5p, miR-34a, miR-3594-3p, miR-3594-5p, miR-361, miR-369-3p, miR-369-5p, miR-374, miR-376a, miR-376b-3p, miR-376b-5p, miR-376c, miR-378, miR-384-3p, miR-384-5p, miR-409-5p, miR-410, miR-423, miR-434, miR-450a, miR-485, miR-487b, miR-495, miR-499, miR-539, miR-542-5p, miR-551b, miR-582, miR-667, miR-674-3p, miR-674-5p, miR-702-3p, miR-7a, miR-7b, miR-9, miR-92b, miR-98, let-424, let-7e, let-7f, let-7a, let-7c.

In preferred embodiments, the methods and compositions comprise at least two anti-miR are administered concurrently to said patient.

In a further embodiment, a method of modifying systemic blood pressure in a patient comprising; analyzing a sample from said patient for gene expression; determining microRNA implicated in the control of blood pressure in the patient; resorting normal blood pressure to the patient by manipulating the system of the network of genes functionally relevant to neurogenic hypertension by administering to said patient at least one anti-miR therapeutic. In certain embodiments, the method further comprising at least two anti-miR therapeutics. In preferred embodiments, the method wherein at least one anti-miR therapeutic is selected from the group consisting of anti-miR 135a-5p and anti-miR-376a-5p or combinations thereof.

A method of rebalancing the function of the autonomic nervous system comprising administering to a patient suffering from an out of balance autonomic nervous system a therapeutic comprising at least one anti-miR of any of the pharmaceutical compositions described herein. In certain embodiments, the method further comprising a step of analyzing a first sample from a patient for gene expression of a predetermined set of genes; analyzing a second sample from said patient for the same predetermined genes and comparing the gene expression between the first and second sample; identifying gene expression changes in autonomic regulator structures; and administering to said patient the therapeutic comprising at least one anti-miR, wherein said anti-miR is selected to modulate expression of at least one gene related to the autonomic regulator structures. In certain embodiments, said first and second samples are taken at least seven days apart.

In a further preferred embodiment, a method of treating a neurological disease comprising: analyzing a first sample from a patient for gene expression of a predetermined set of genes; analyzing a second sample, from said patient for the same predetermined genes and comparing the gene expression between the first and second sample; identifying gene expression changes in autonomic regulator structures; and administering to said patient the therapeutic comprising at least one anti-miR, wherein said anti-miR is selected to modulate expression of at least one gene related to the autonomic regulator structures.

In a further preferred embodiment, a method to treat the autonomic nervous system in a patient comprising: identifying hub microRNA that participate in a disinhibition network in which negative regulators of signaling and metabolic pathways are targeted by microRNAs to amplify signaling and metabolic activity; administering to said patient an anti-microRNA that targets and blocks the activity of the hub microRNA to disinhibit the negative regulators of signaling and metabolic pathways, and thus increasing the inhibition of these pathways to rebalance the function of the autonomic nervous system.

In the compositions and methods described herein, the therapeutic or method wherein the treatment comprises a first and a second anti-miR, wherein said first and said second anti-miR each target a different gene.

In a further embodiment, a method for regulating astrocytic processes in a patient comprising: adminstering to said patient an effective amount of an anti-miR therapeutic selected from the group consisting of 135a-5p, 3'761-5p, and combinations thereof.

In a further embodiment, a method of treatment of hypertension comprising: administering to a patient a first therapeutic comprising at least one anti-miR therapeutic selected from the group consisting of anti-miR 135a-5p and anti-miR376a-5p for a sufficient amount of time to reduce the mean arterial pressure in a patient to below 110 mm Hg. In a further embodiment, the method comprising a further step of testing said patient for mean arterial pressure at least 24 hours after administration of the at least one anti-miR; administering to said patient a second therapeutic comprising both anti-miR 135a-5p and anti-miR 376a-5p.

A method of treatment provides for a single therapeutic, either anti-miR-135a or anti-miR-376a for a pre-determined amount of time. Evaluation of MAP continues throughout the therapeutic treatment. Should MAP fail to sufficiently fall to safe levels, then a combined therapy can be utilized. In this manner, the treatment may be sufficient with a single therapeutic, and saving the combined therapeutic for a later time, should the first therapy be insufficient. This allows for a tiered approach to treatment.

A method may comprise providing a therapeutic treatment for a predetermined amount of time, comprising one of an anti-miR 135a or anti-miR-376a, at a dose sufficient to drop MAP; determining whether said drop in MAP is sufficient to reduce hypertension to a safe level, between 110 and 65 mm Hg; providing a second therapeutic comprising both anti-miR 135a and anti-miR-376a if the MAP does not fall into the category of 110 to 65 mm Hg. The administration of the first or second therapeutic can continue for a period of 7-30 days, and review whether the MAP stays in a safe zone, or the therapeutics may continue for a longer, possible indefinite period for control of hypertension. Preferably the treatment provides sufficient therapeutic efficacy for about 28 days.

A method of treatment of hypertension comprising administering to a patient a therapeutic comprising one of anti-miR-135a or anti-miR-376a; measuring hypertension at a first time before administration and again at a second time after administration; evaluating mean arterial pressure in said patient with a target of 110 mm Hg in said patient; providing a second dose of the therapeutic every 28 days to maintain said therapeutic levels in the body. In the method, wherein a second dose comprises a combination of both anti-miR-135a and of anti-miR-376a if said second measurement is not lower than 110 mm Hg.

Thus far, there have been limited studies of microRNAs in the brain during the development of neurogenic hypertension, as our work is the first global study of microRNAs in the brainstem during the development of hypertension. Therefore, performing microRNA in vivo manipulation studies through the employment of antisense technologies or viral vectors, we can elucidate the mechanistic role of microRNA in the development of hypertension. microRNAs are positioned as unique therapeutic targets in that they are specific enough so an antisense inhibitor will effectively bind to the microRNA of interest, and they have large networks of predicted molecular targets. Discovering microRNAs with many predicted targets relevant to a particular disease may prove to be more effective in as a therapeutic than simply targeting one or two proteins with a small molecule inhibitor.

BRIEF DESCRIPTIONS OF THE FIGURES

FIG. 1 shows the triangulation of neurogenic hypertension. Inflammation, Angiotensin II, and vascular dysfunction contribute to increased sympathetic nerve activity, leading to hypertension. (Image Credit: Fisher and Paton 2012)

Figure 2:
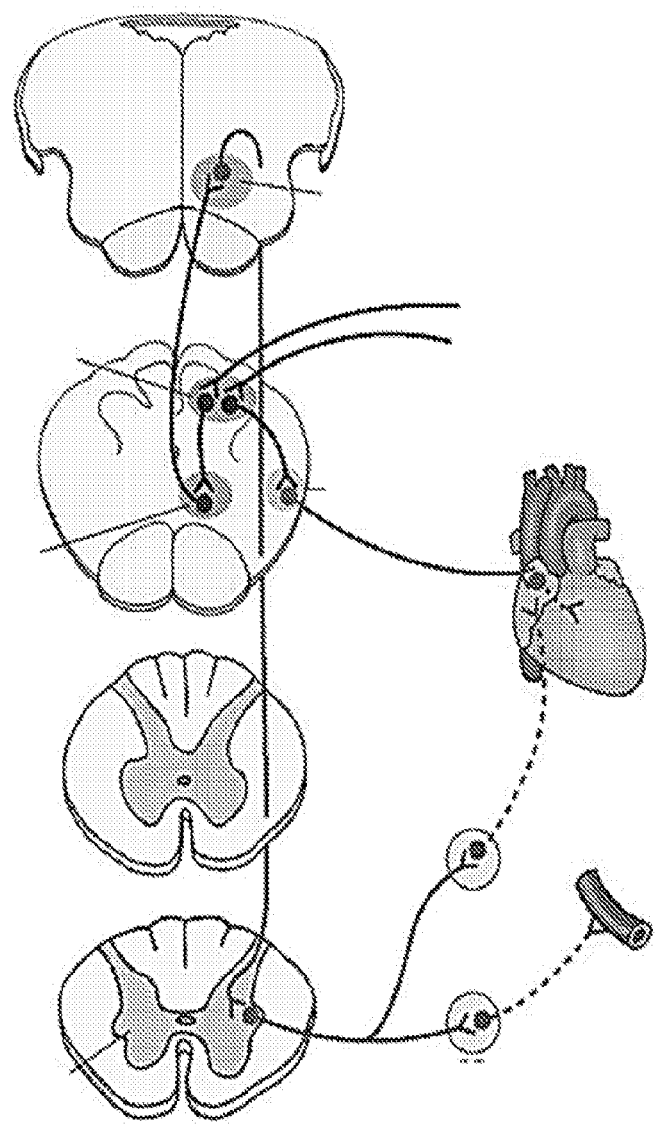

FIG. 2 depicts the anatomy of the Baroreflex. Afferents from the baroreceptors synapse in the NTS and CVLM and RVLM, where blood pressure set point is modulated. Efferent nerves output to heart and blood vessels to adjust blood pressure as part of this negative feedback loop. (Image Credit: Guyenet 2006).

Figure 3:
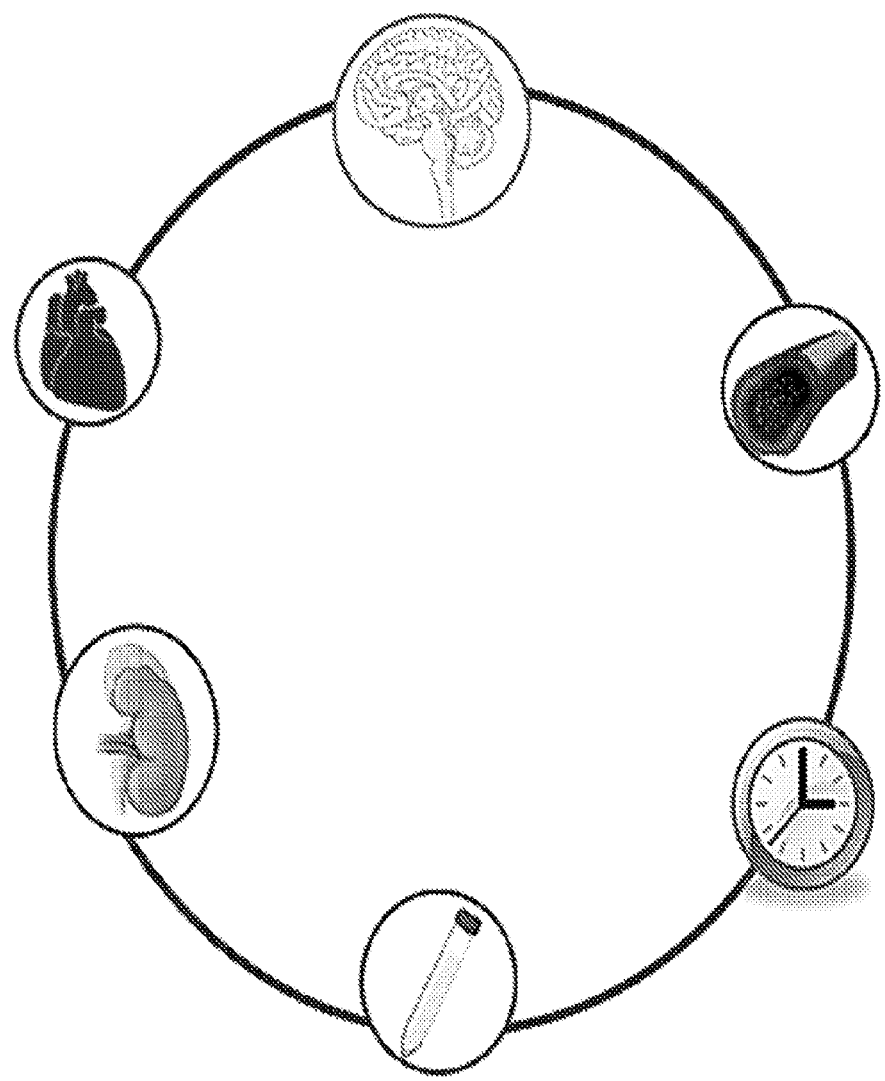

FIG. 3 shows a summary of Literature-Derived Knowledge of microRNAs in HTN. In the CNS, prior to DeCicco et al., 2015, one microRNA was characterized in essential hypertension. (Image Credit: Marques et al., 2014). miR-22 is related to the CNS (brain image at top). Increase in miR-132, miR-145, miR-212, miR-221, miR-222, and Lnc-ANG362 are related to the vascular smooth muscle cells, to the right of the brain image. The clock image depicts Diurnal BP variation, during the active phase, decrease in miR-181a. The Unire and systemic circulation (bottom vial) is related to increase in hcmv-miR-UL112, let-7e, miR-21, miR-92a, miR-130a, miR-195, miR-221, miR-222, miR-4516, decrease in miR_9, miR-27a, miR-126, miR-133a, miR-143, miR-145, miR-150, miR-192, miR-296-5p, miR-4516, with related or possible implications of miR-34a, miR-34b, miR-122, miR-155, miR-449, miR-511, miR-578, miR-608, miR-637, and miR-765. The Kidney is related to increase in miR-132 and miR-212, with increase at the cortex for miR-21, miR-126, miR-196a, and miR-451, with decrease in miR-181a, miR-639, and miR-663, and the Medulla having a decrease of miR-638 and let-7c. Finally, the heart has increase of miR-132 and miR-212, with implication of miR-425.

FIGS. 4A-D shows a comparison of microRNA expression patterns with that of the predicted targets by RNA22 and miRWALK algorithms. Key microRNAs plotted with transcripts predicted to be a target of its respective microRNA. A) miR-135a and its predicted target Il1rn show opposite behavior in SHR NTS as the Pre and Onset stages. B) miR-135a shows anti-correlated behavior with target Agtrap in SHR in NTS and RVLM at the Pre-Onset Stage, and in RVL WKY at the Pre-Onset Stage. C) miR-376a shows opposite expression levels than target PTGR1. D) miR-376a show inverse correlated behavior with target Agtrap in SHR NTS at the Pre-Onset stage.

Figure 5:
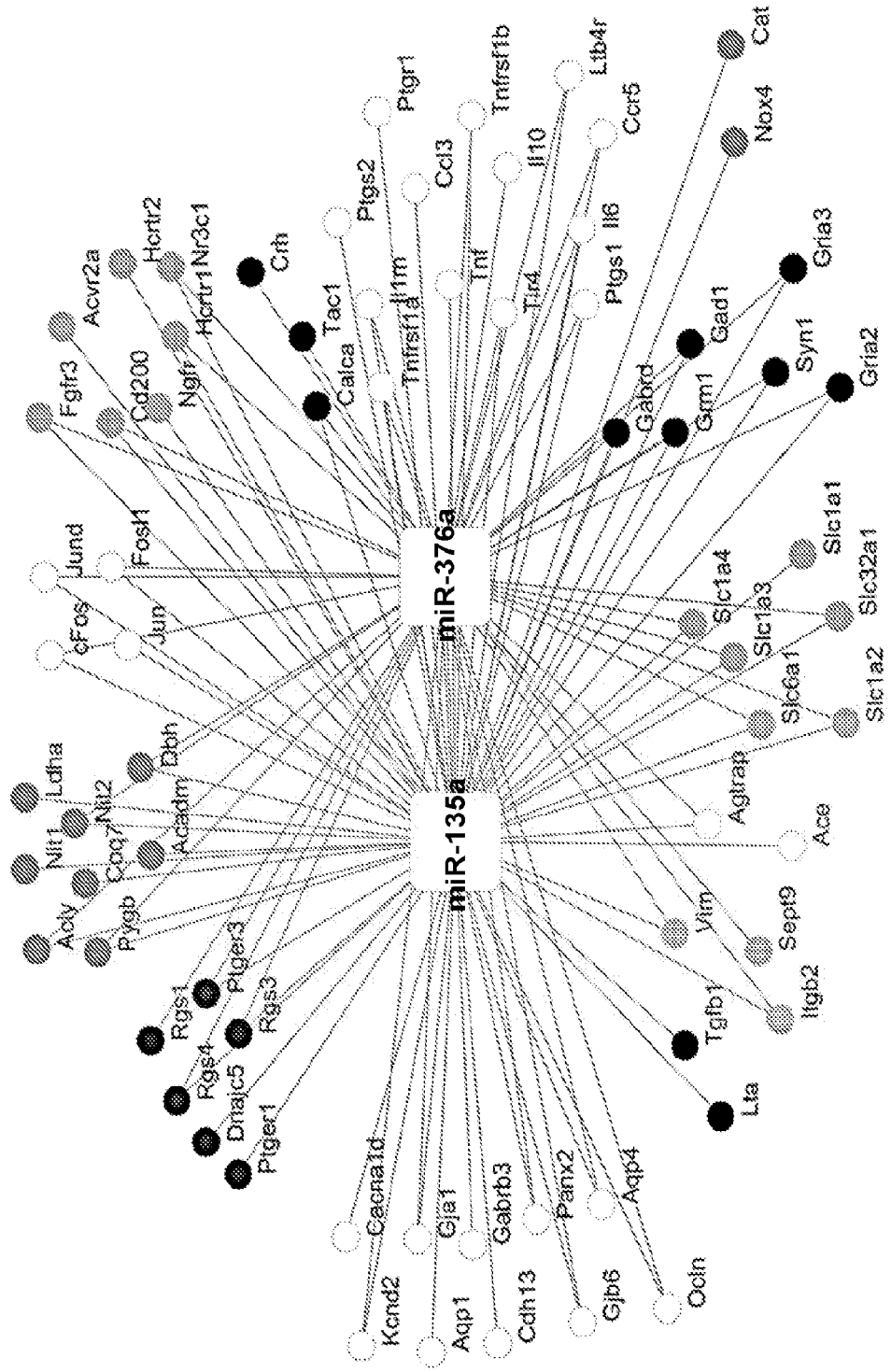

FIG. 5 depicts a network representation of microRNA-putative target interaction Network representation of microRNA—putative target mapped to pathway annotations derived from literature and gene ontology. Key microRNAs at the hypertension onset stage in NTS of miR-135a regulatory network and miR-376a regulatory network (Key microRNAs at the prehypertension stage in RVLM of miR-135a regulatory network and miR-376a regulatory network. Edges are mapped to correlation data differences of SHR-WKY. Blue: positive, Red: negative. Line connections are present if the transcript is a predicted target of a microRNA with line thickness representing relative strength of correlation subtraction [−2, 2].

Figure 6A:
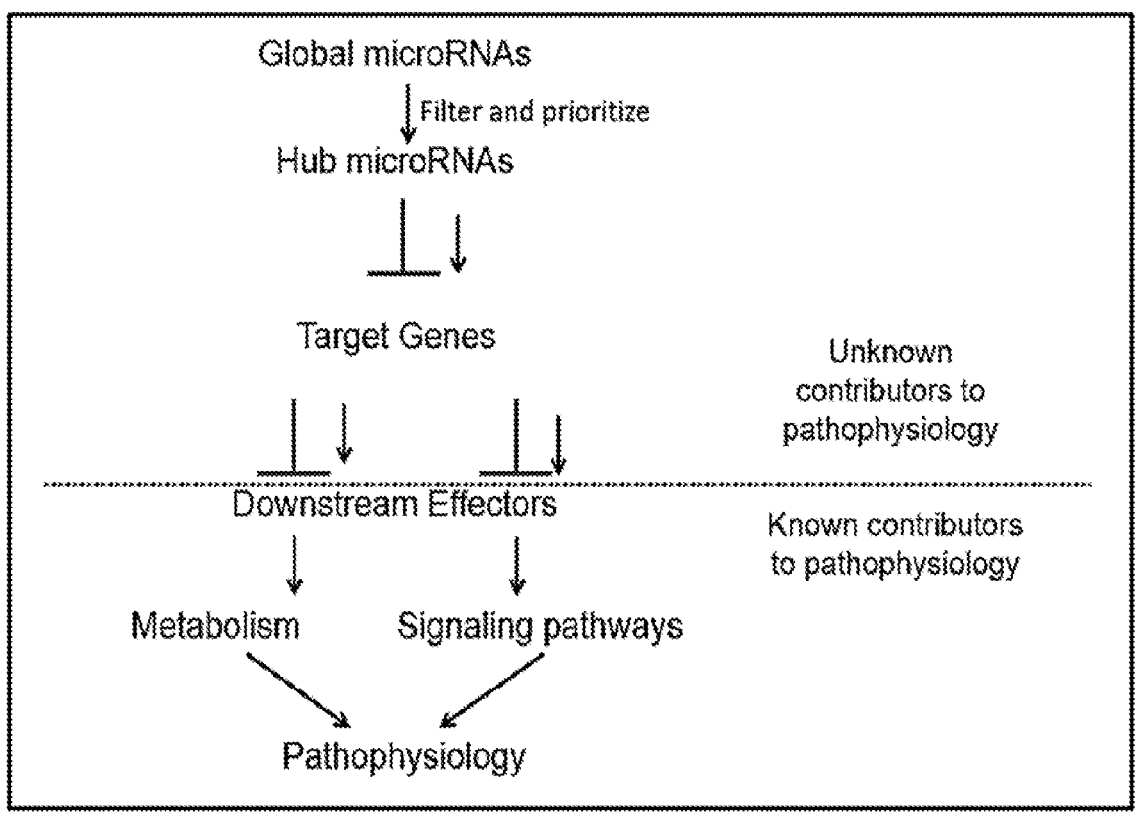
Figure 6B:
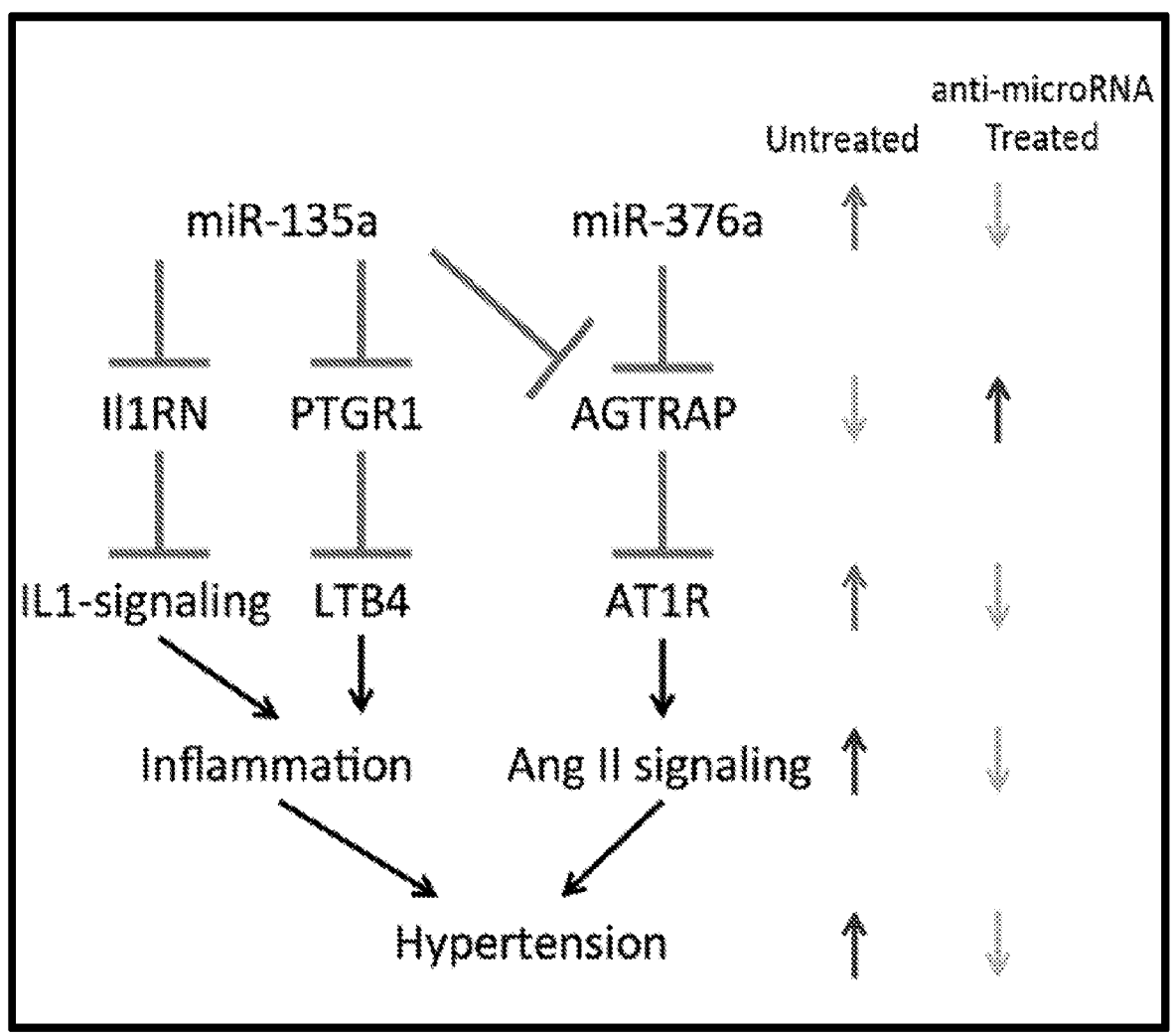

FIGS. 6A and 6B depict the outcome of our network analysis as a generalized network scheme (FIG. 6A) and specific instantiation (FIG. 6B) involving hub microRNAs and their targets predicted by our computational analysis of high-throughput microRNA expression data, target gene prediction, and analysis for double-negative motifs that represent disinhibition of key signaling and metabolic pathways. FIG. 6B portrays the specific subset of larger data-driven microRNA regulatory network depicted previously in FIG. 5A, and captures the interactions relevant to the signaling and metabolic pathways well-established in the hypertension and SHR literature, focusing on Angiotensin II, leukotriene metabolism, and leukotriene-mediated inflammatory signaling. The network relates key microRNAs either persistently up-regulated or showing a larger rise in SHR than in WKY during the developmental phase of hypertension. A common feature of this network is that the two key microRNAs are predicted by a consensus of bioinformatics tools to target negative regulators of pathways that are amplified in SHR during the development of hypertension.

FIGS. 7A-E represents stereotaxic LNA Injection and Biodistribution. Stereotaxic LNA injection into IVth intracerebral ventricle distributes into the bilateral NTS (A and B). Laser capture dissection of the bilateral region removes entire 10 uM section (C) within region boundary (D), and retains LNA (E).

Figure 8A:
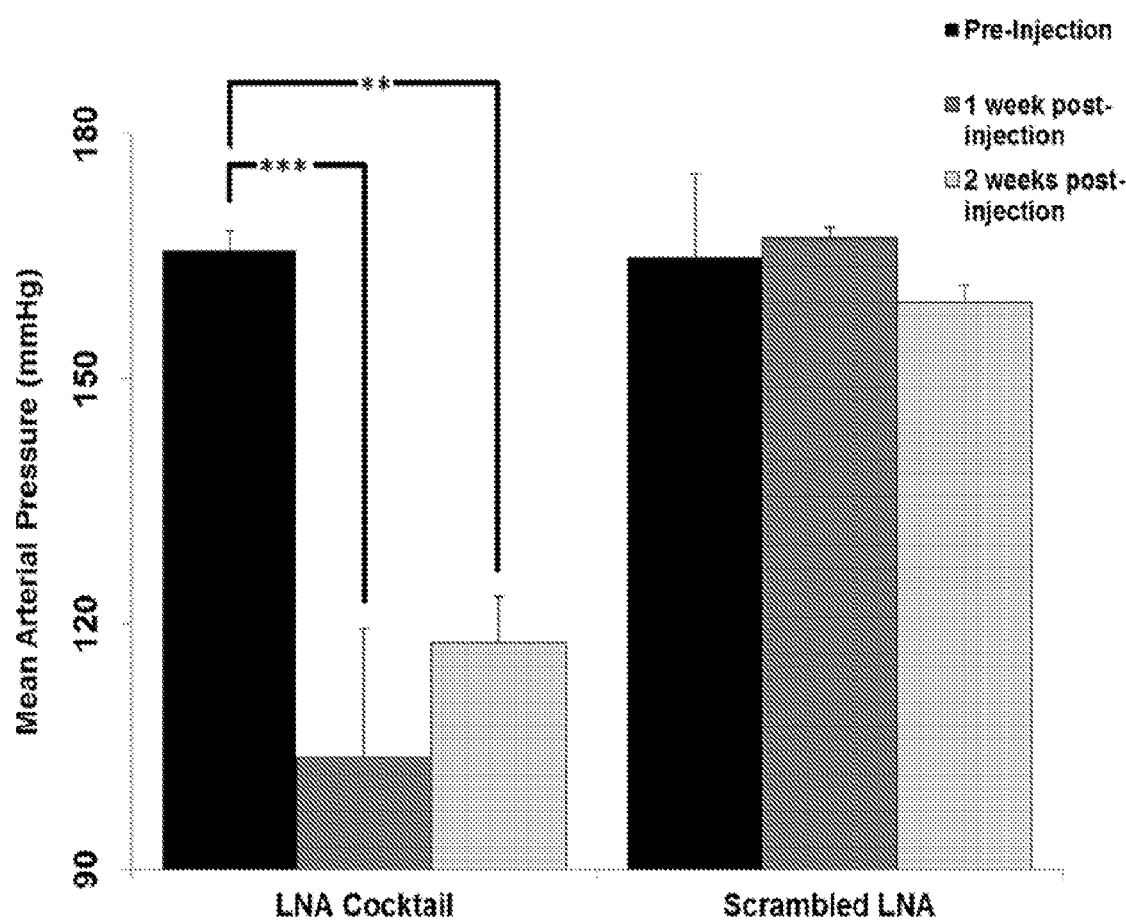
Figure 8B:
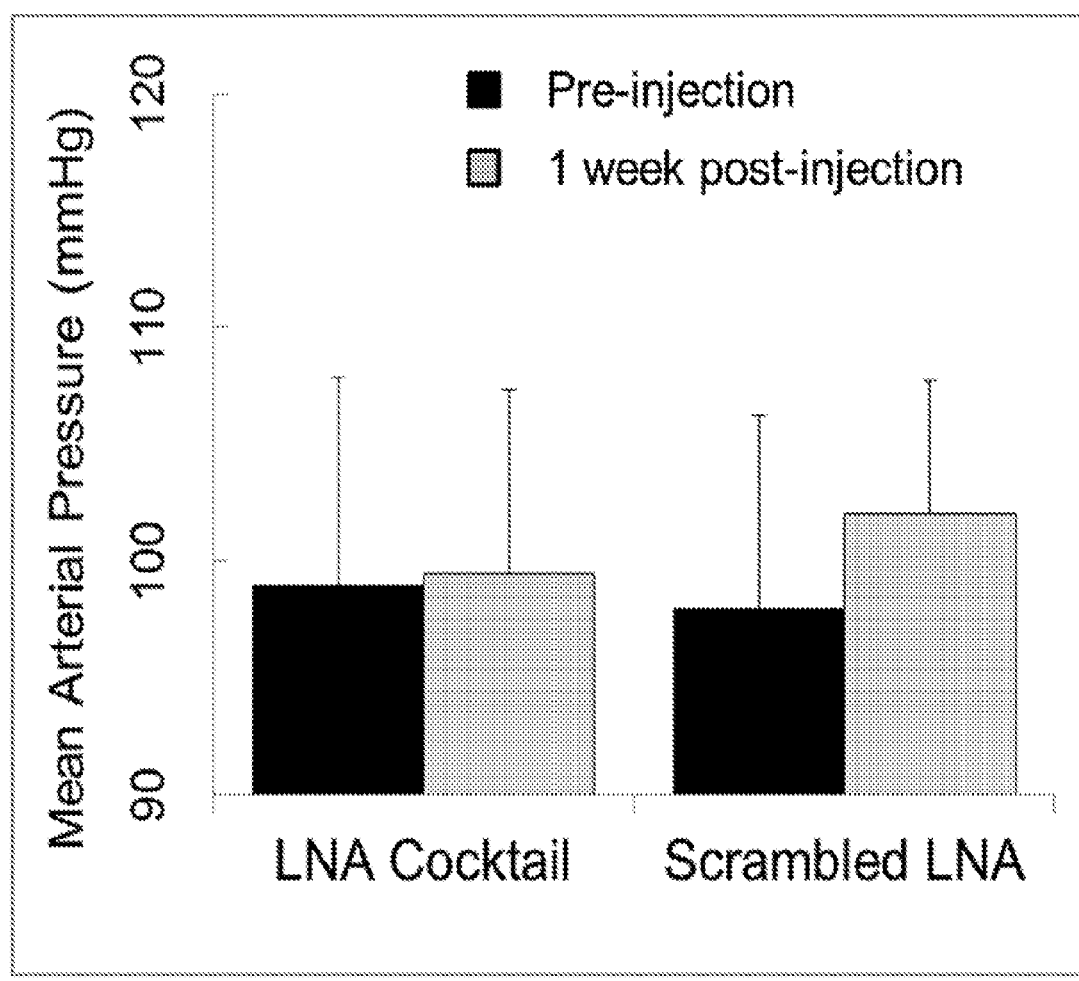

FIGS. 8A and 8B depict inhibition of the microRNAs miR-135a and miR-376a in vivo via injection into the IVth intracerebral ventricle attenuates hypertension. Blood pressure measurements show decrease in mean arterial pressure in the LNA anti-miRNA cocktail group and not in the scrambled LNA nor no surgery group one week and two weeks after injection; n=5 for all groups (*$p<0.001$,  $p<0.01$ nested Analysis of Variance (ANOVA) with Tukey Honest Significant Difference (HSD). FIG. 8B depicts Injection of the LNA anti-miR135a and anti-miR376a cocktail does not have an appreciable effect on WKY rats. Rats used were aged-matched to the SHR data shown previously, n=3 for each experimental group. Nested ANOVA with Tukey HSD showed no statistically significant difference between pre-injection and post-injection for either groups.

FIGS. 9A-G portrays inhibition of microRNA-135a and microRNA-376a in vivo that attenuates hypertension at the chronic stage. Inhibition of microRNAs miR-135a and miR-376a in vivo via injection into IVth intracerebral ventricle attenuates chronic hypertension. Each line indicated an individual animal. (A) Study design of drug administration at 29 weeks of age, and blood pressure reading every week after drug injection of 25 ul of 10 uM LNA cocktail (B) Blood pressure measurements show decrease in mean arterial pressure, systolic (C) and diastolic pressure (D) in SHR but not in age-matched WKY (E, F< and G, respectively) rats that received the same set of treatments. N=1-2 rats per condition. Each line represents one animal.

Figure 10:
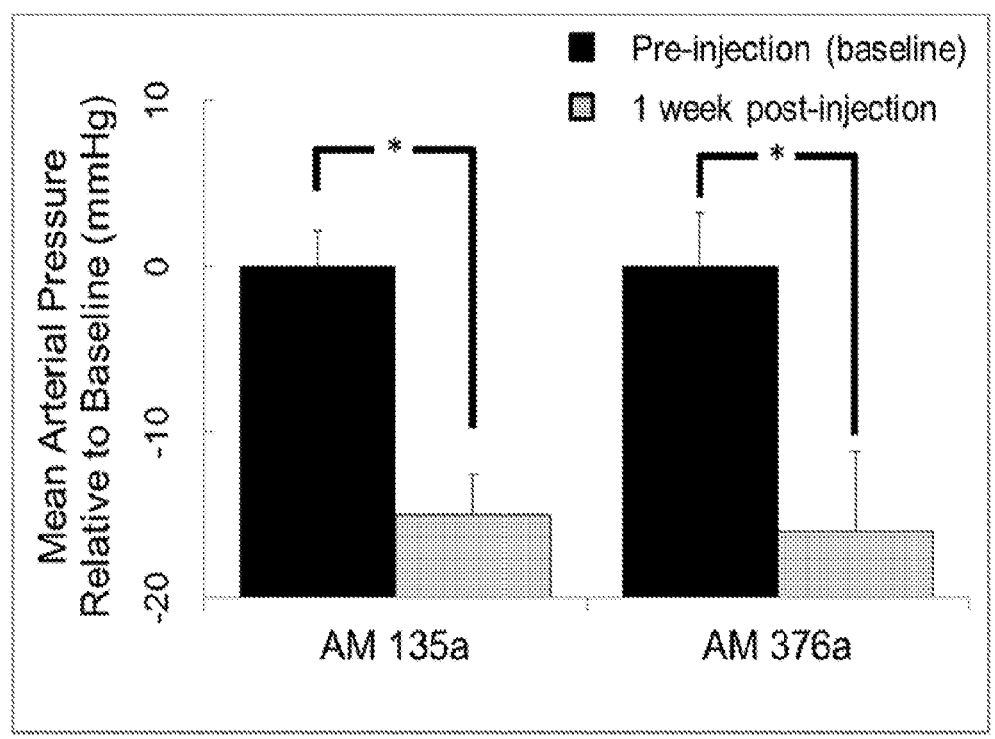

FIG. 10 depicts Individual anti-miRNA injections against either miR-135a or miR-376a into the IVth ventricle each lower mean arterial pressure (MAP). The effect size is not as large as the two-anti-miRNA LNAs, but still significant compared to the pre-injection baseline blood pressure level. Comparing these results with those in FIG. 8A show that the combinatorial intervention into the microRNA regulatory network with two anti-microRNAs is synergistic, i.e., the net reduction in blood pressure in response to simultaneous inhibition of both microRNAs in vivo is larger than the sum of the individual effect of inhibition of each microRNA in vivo.

Figure 11:
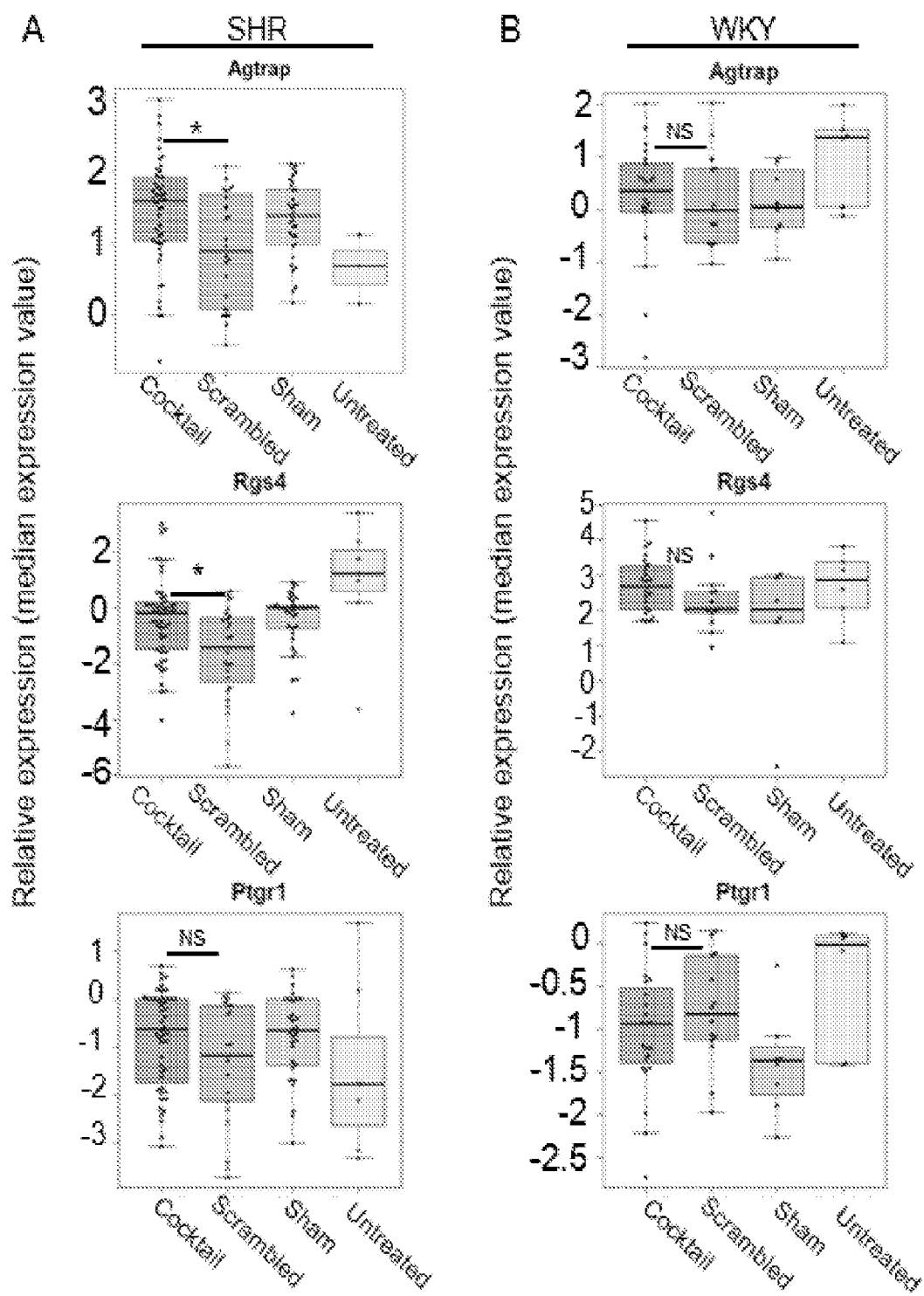
Figure 11C:
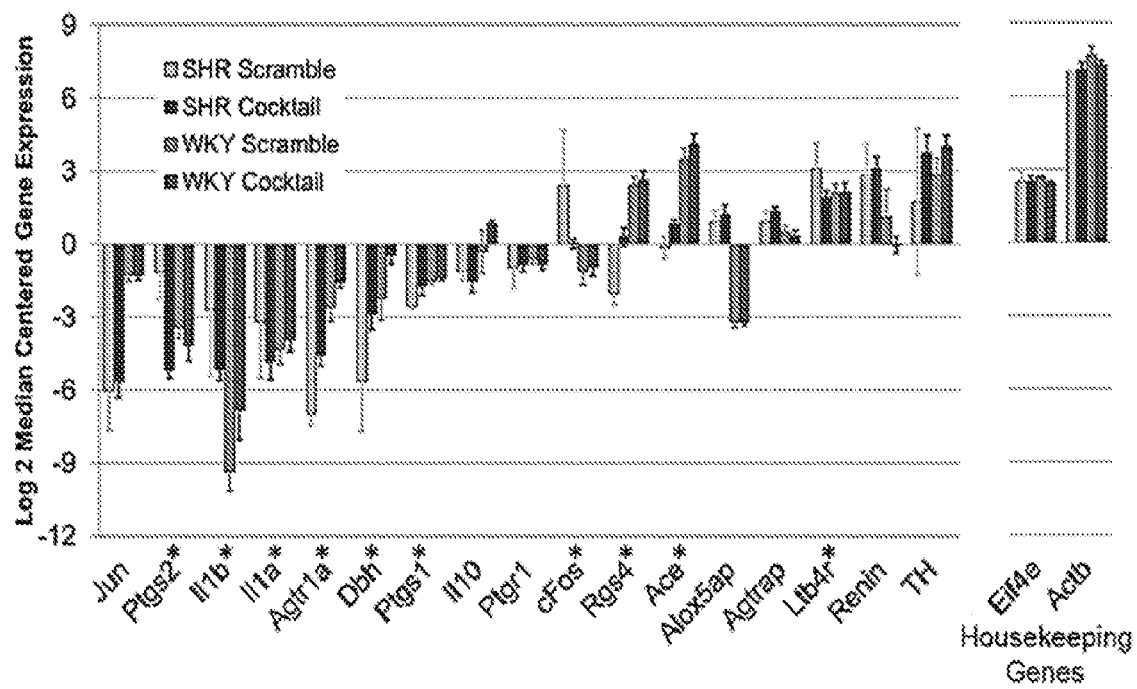

FIGS. 11A-C shows gene expression levels modulated upon microRNA inhibition. Gene expression levels remain higher in LNA cocktail injected animals for up to two weeks post injection in SHR compared to Scrambled Oligo. Controls (A), but not in age-matched WKY controls (B). *$p<0.05$ ANOVA with Tukey HSD Post-Hoc significance. FIG. 11C depicts Gene expression for bilateral NTS samples collected from all animals across each treatment group. Starred (*) genes showed SHR-anti-microRNA cocktail changes from Scrambled Oligo treatment that move towards expression levels that are more congruent with WKY expression.

FIGS. 12A-E portrays microRNA-135a inhibition in astrocytes modulates gene expression levels. microRNA-135A inhibition in astrocyte cell line (CTX-TNA2) increases expression level of predicted targets. Agtrap, Ptgr1, CD200. And Slc1a (A-E), and subsequently decreases non-predicted target Leukotriene B4 receptor transcript expression levels *$p<0.05$, ANOVA with Turkey HSD Post-Hoc Significance.

FIGS. 13A-D shows the dynamic changes in expression of LTB4 related genes over time in NTS. A) Summary of genes measured as they relate to Arachidonic Acid metabolism. Evaluation of six genes affecting LTB4 production (B, C-left panel), degradation (C-right panel) and signaling receptors (D) with reference to housekeeping gene Eif4e and WKY onset time point. * $p<0.05$, Strain Difference Significant, 2-factor ANOVA, Tukey HSD post-hoc $p<0.05$. Of note for strain significant difference is: AloxAP, p-value=0.076 and Lta4h, p-value=0.077. Und, Undetermined Expression, n=3-4 per gene. This provides data for known Quantitative Trait Loci (QTL) of microRNAs showing differential expression dynamics during the development of hypertension. These results show that the microRNAs identified by our analysis are present in genetic loci that are relevant to blood pressure control, hypertension, cardiac health, and kidney function, providing additional literature support for prioritizing the microRNAs in our computational analysis for identifying hub microRNAs and their regulatory networks.

Figure 14A:
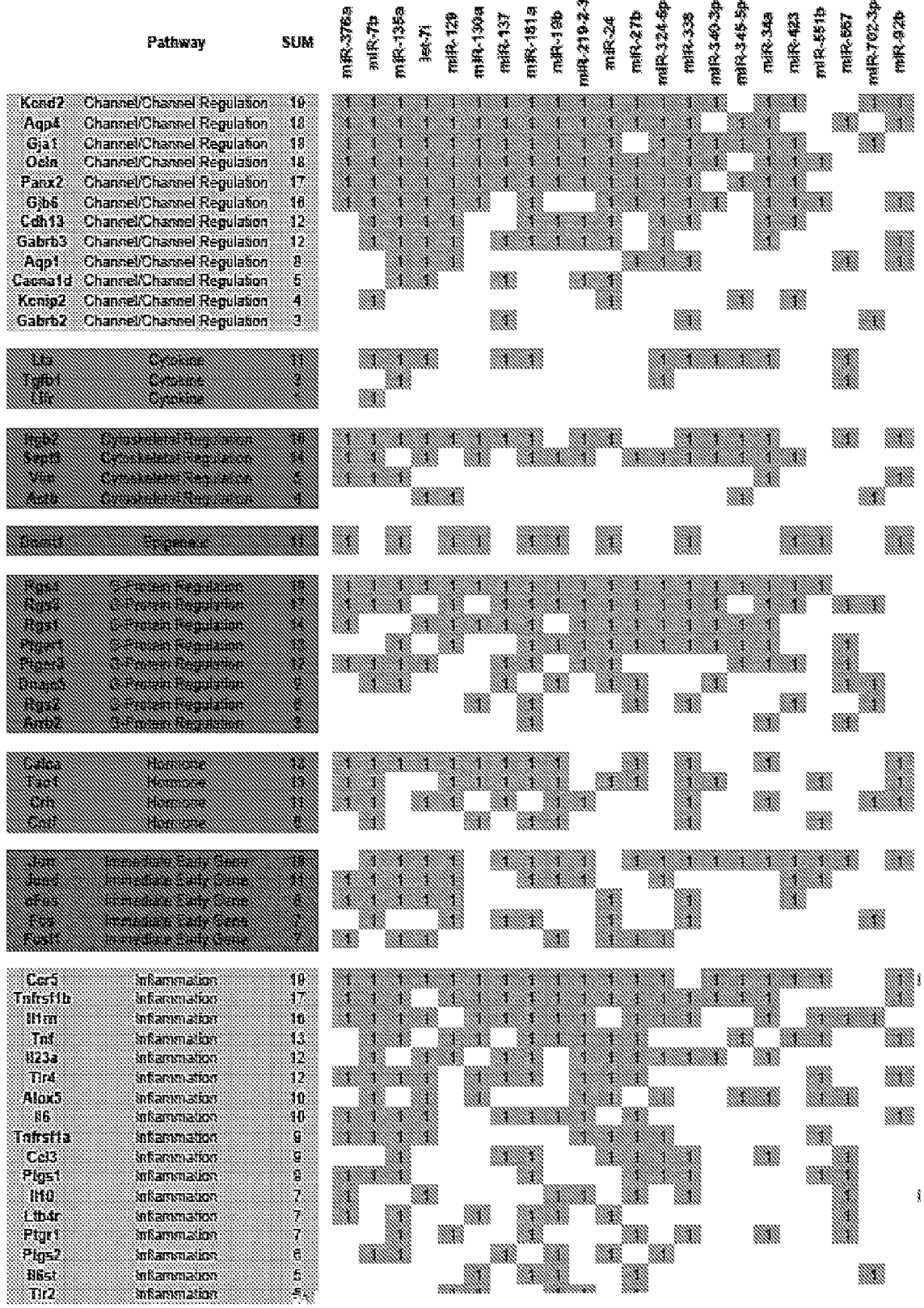
Figure 14B:
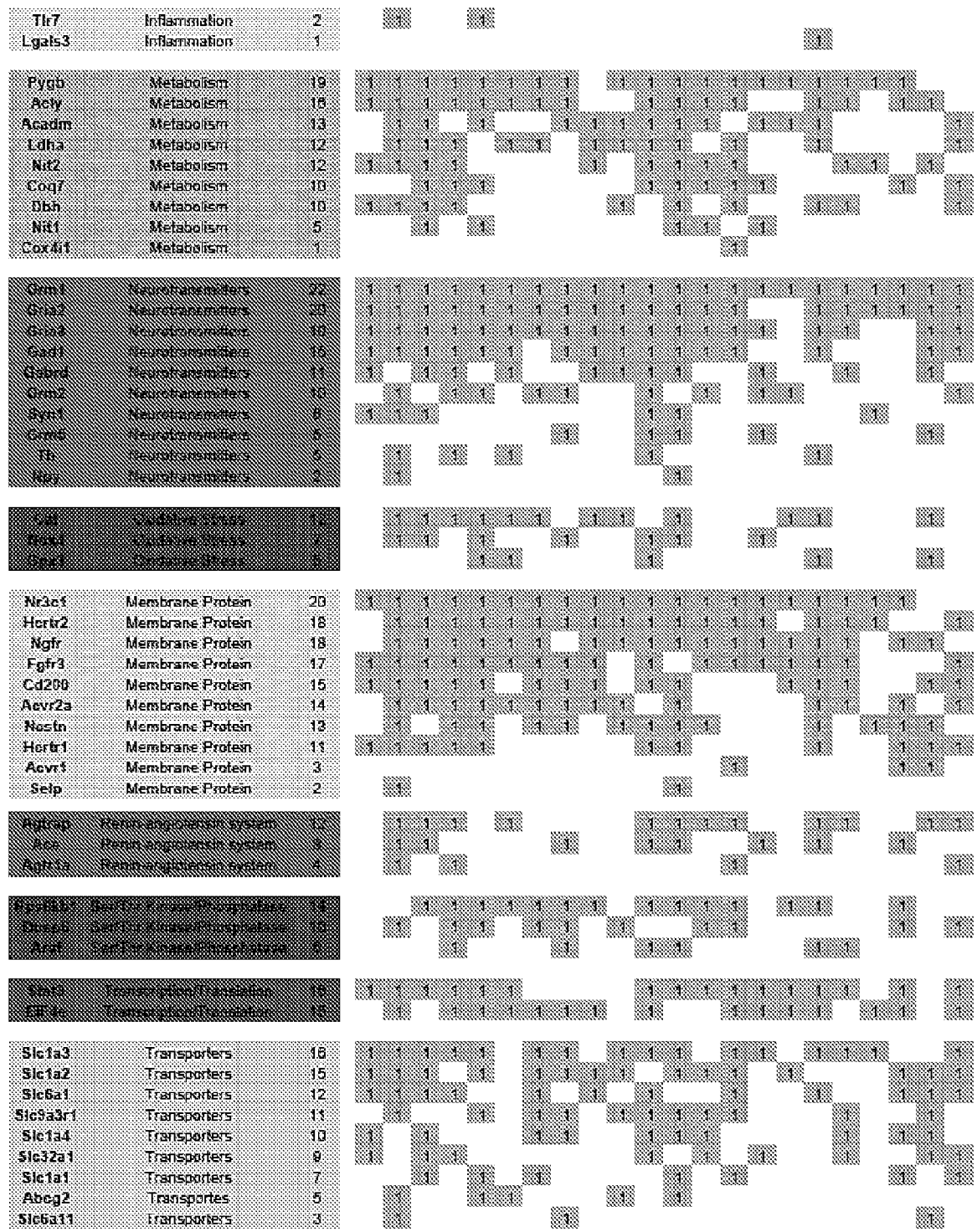

FIGS. 14A-B shows putative miRNA; mRNA target network including all predicted interactions from bioinformatics target prediction grouped by signaling pathway. This is the underlying data for FIG. 5.

DETAILED DESCRIPTION OF THE EMBODIMENTS

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

As used herein, the term "ACE" refers to Angiotensin II Converting Enzyme.

As used herein, the term "AGTRAP" refers to Angiotensin.

As used herein, the term "ANG II" refers to Angiotensin II Receptor Type 1.

As used herein, the term "AT1R" refers to Angiotensin II Receptor Type 1.

As used herein, the term "BP" refers to Blood Pressure.

As used herein, the term "CCR1" refers to Chemokine Receptor 1.

As used herein, the term "CCR5" refers to Chemokine Receipt 5.

As used herein, the term "cDNA" refers to Complementary DNA.

As used herein, the term "CNS" refers to Central Nervous System.

As used herein, the term "CO" refers to Cardiac Output.

As used herein, the term "DNA" refers to Deoxyribonucleic Acid.

As used herein, the term "DP" refers to Diastolic Pressure.

As used herein, the term "ENCODE" refers to the Encyclopedia of DNA Elements.

As used herein, the term "HTN" refers to Hypertension.

As used herein, the term "ICV" refers to Intracerebroventricular.

As used herein, the term "I1-1B" refers to Interleukin 1 Beta.

As used herein, the term "I1 RN" refers to Interleukin 1 Receptor Antagonist.

As used herein, the term "IL6" refers to Interleukin 6.

As used herein, the term "LNA" refers to Locked Nucleic Acids.

As used herein, the term "LTB4" refers to Leukotriene B4.

As used herein, the term "MAP" refers to Mean Arterial Pressure.

As used herein, the term "MCP1" refers to Monocyte Chemoattractant Protein 1 miRNA: microRNA mmHg: millimeters of Mercury—a unity of BP measurement: 1 mmHg=0.13 kPA=0.0023 atm.

As used herein, the term "qPCR" refers to Quantitative polymerase chain reaction.

As used herein, the term "RNA" refers to Ribonucleic Acid.

As used herein, the term "SHR" refers to Spontaneously Hypertensive Rat.

As used herein, the term "SP" refers to Systolic Pressure.

As used herein, the term "TNFa" refers to Tumor Necrosis Factor Alpha.

As used herein, the term "WKY" refers to Wistar Kyoto Rat (SHR Control).

As the Encyclopedia of DNA Elements (ENCODE) project, a public research project initiated by the US National Human Genome Research Institute, was accumulating momentum following the completion of the Human Genome Project in April 2003, several astounding results were discovered (Bernstein et al. 2012; Mehta, Jalan, and Mookerjee 2013; Sanfilippo and Hewitt; "The ENCODE (Encyclopedia Of DNA Elements) Project." 2004). In 30 scientific publications, released in September 2012, ENCODE led to new knowledge claiming over 80% of the human genome is implicated in RNA or epigenetic events in at least one cell type (Bernstein et al. 2012). Additionally, ENCODE uncovered that Single Nucleotide Variations (SNV), and other genomic markers of disease, discovered by Genome Wide Association Studies (GWAS) were actually occurring in regions of the genome that do not code for protein. Furthermore, from ENCODE, we learned that we are able to quantitatively correlate RNA expression levels with epigenetic marks and with transcription factor promotor activity (Bernstein et al. 2012). Non-coding regions of the genome, specifically, non-coding RNA were brought to the forefront of science.

The beginning of this work coincided exactly with and was inspired by the release of the ENCODE consortium data. We embarked on a scientific quest to understand the role of non-coding RNA in disease, as we believe there to be great promise in therapeutics formulated from non-coding RNA. Despite our desire to focus on many RNAs and many diseases, we focused on a category of RNA termed, microRNA (miRNA), and a disease called essential hypertension. Despite 75% of the United States population being hypertensive, only half of them have their blood pressure fully controlled (Go et al. 2014). The current treatment guidelines in the clinic for essential hypertension involve diuretics, Angiotensin II Receptor (AT1R) Antagonists, Angiotensinogen Converting Enzyme inhibitors and B-Adrenergic Receptor Blocking drugs (Dolan and O'Brien 2016; Wolf-Maier et al. 2004). However, all of these drugs target proteins implicated in the development and maintenance of hypertension, and not any other type of cellular product, such as a microRNA, which may be upstream of these receptors and enzymes being targeted with medication. microRNAs can modulate protein expression levels and therefore, intracellular signaling induced by such proteins (Dvinge et al. 2013; Schmiedel et al. 2015).

Decades of research on spontaneously hypertensive rat (SHR) model of hypertension have suggested that essential hypertension occurs as a result of perturbations in the blood pressure control network. Previous work has found perturbations in the kidney, the carotid body, and the nucleus of the solitary tract (NTS) each to be sufficient to control hypertension. Within each organ system too, there are claims that one signaling pathway or another is the primary driver of hypertension. Instead, it may be more useful to consider hypertension as the emergent property of a network that has been pushed out of a normotensive equilibrium into a compensatory, yet ultimately pathological state. The crosstalk between and within organ systems can be largely represented by an interconnected set of gene regulatory networks.

The central questions we aim to address throughout this work are two-fold: 1) Can we characterize the microRNA regulatory networks in the CNS, more specifically the brainstem, throughout the development of hypertension; and 2) Can we modulate the expression levels of microRNAs in the brainstem to prevent or revert hypertension? Through a series of in vivo, computational, bioinformatic, and in vitro approaches we aim to provide a new understanding of the adaptive molecular mechanisms underlying central regulation of blood pressure set point, and we provide proof of principle for a novel, druggable pair of microRNAs which underlie the development of hypertension.

Indeed, in the broadest sense the methods described herein provide a unique gene regulating network implication one or more microRNA. By identification of implicated microRNA, therapeutic treatments can be utilized with anti-miR for remediation and regulation of system function. Thus, the processes and methods described herein comprise two essential steps (1) Acquisition of high-throughput data revealing the broad pattern of small to modest gene expression and regulatory microRNA changes tracking development of a disease process, followed by computational analysis predicting the gene regulatory network and of the hub microRNAs driving it's changed behavior. (2) Design and application of therapeutic anti-microRNA agents for introduction to the system to prevent or remediate the disease state by restoring normal network function.

However, with particular regard to hypertension, we can focus on the microRNA that are most highly implicated. Hypertension is a major chronic disease whose molecular mechanisms remain poorly understood. In order to uncover the landscape of microRNAs that are altered during the development of hypertension, we compared the neuroanatomical patterns of microRNA expression in the brainstem of the spontaneous hypertensive rat (SHR) to the Wistar Kyoto rat (WKY; control). SHR serves as a representative animal model of human essential hypertension. Human hypertension is extremely variable and can provide little insight on early stage and developmental processes. In this regard, current evidence indicates that hypertensive strains of rats and susceptible humans have much in common, both phenotypically and genotypically (Atanur et al., 2010; Knight, Munroe, Pembroke, & Caulfield, 2003), and the SHR is by far the most widely studied animal model of hypertension. The SHR has the advantage of hypertension developing from a young age over several weeks, which permits study of changes in the pre-hypertensive age, thereby separating effects of high blood pressure from transcriptional processes that may cause hypertension and are altered prior to onset of hypertension. We quantified 419 well-annotated microRNAs in the nucleus of the solitary tract (NTS) and rostral ventrolateral medulla (RVLM), from SHR and WKY rats, during three main stages of hypertension development. Changes in microRNA expression were stage- and region-dependent, with a majority of SHR vs. WKY differential expression occurring at the hypertension onset stage in NTS versus at the prehypertension stage in RVLM. Our analysis identified 24 microRNAs showing time-dependent differential expression in SHR compared to WKY in at least one brain region. We predicted potential gene regulatory targets corresponding to catecholaminergic processes, neuroinflammation and neuromodulation using the miRWALK and RNA22 databases, and we tested those bioinformatics predictions using high-throughput qPCR to evaluate correlations of differential expression between the microRNAs and their predicted gene targets. We found a novel regulatory network motif consisting of microRNAs likely down-regulating a negative regulator of pro-hypertensive processes such as angiotensin II (Ang II) signaling and leukotriene-based inflammation. Our results provide new evidence on the dynamics of microRNA expression in the development of hypertension and predictions of microRNA-mediated regulatory networks playing a region-dependent role in potentially altering brainstem cardiovascular control circuit function leading to the development of hypertension.

Our results are the first and the only study on microRNA changes in the brainstem autonomic control circuits that lead to development of hypertension. Using a systems biology approach integrating high-throughput data, network analysis, and in vivo and in vitro experimental testing of anti-microRNA interventions, we have identified microRNAs in the brainstem of the Spontaneously Hypertensive Rat (SHR) relative to Wistar-Kyoto (WKY) controls with significantly different expression levels in two key neuroanatomical regions, the nucleus of the solitary tract (NTS) and the rostral ventrolateral medulla (RVLM). Alterations in microRNA expression levels are time and location-dependent, differing at a key period of hypertension onset in NTS, but differing at the prehypertensive stage in RVLM. Using correlational relationships and network identification analysis, between microRNAs and mRNAs measured, we identified a double-negative regulatory motif consisting of a microRNA down-regulating a negative regulator of a pro-hypertensive signaling pathway such as Angiotensin II signaling and leukotriene-based inflammation. We demonstrated for the first time that the broad concordance of microRNA dynamics and target gene expression compose a regulatory network in the brainstem underlying hypertension. We then localized the regulatory network to different cell types in these regions in the brain. From the cohort of microRNAs we identified, microRNA-135a and microRNA-376a were previously shown to be enriched in astrocytes, a reactive immune cell in the brain, and neurons, respectively. Having identified two microRNAs, with cell-type specific properties, in SHR at a particular key time point in the development of hypertension, we performed in vivo manipulation studies directing microRNA antagonists directly into the IVth intracerebral ventricle (ICV) in the central nervous system (CNS) to normalize the expression of the disease-associated microRNAs in SHR through stereotaxic surgery. For the first time, our results demonstrate microRNA perturbations in the brain can elicit physiological effects, reducing blood pressure. In this context, disease-associated microRNAs represent a new class of targets for development of microRNA-based therapies, which may yield patient benefits unobtainable by conventional therapeutic approaches.

In a preferred embodiment, we show that small perturbations in the gene regulatory networks in the NTS by selectively blocking two microRNAs (miR-135a and miR-376a) are sufficient to prevent development of hypertension in the SHR model. Furthermore, this effect appears driven by only modest changes in putative gene targets of these miRNAs, suggesting that the combination of genes that are targeted in the network is responsible for the effect rather than just one gene or another. While the use of anti-sense oligonucleotides to treat hypertension is itself novel, the demonstration that hypertension is the consequence of network emergence suggests new treatment paradigm altogether is needed. Essential hypertension is a morbid disease with wide impact. One third of the U.S. population is hypertensive, and despite 75% using an anti-hypertensive medication, only 53% have their blood pressure fully controlled (Go et al. 2014). In 2011, hypertension cost the United States $46 Billion in health care services, medications and missed days of work (Mozaffarian et al. 2015). Furthermore, over one billion patients are affect worldwide by this disease, which accounts for 50% of strokes and 28% of kidney failure (Go et al. 2014). Blood pressure is a measurement consisting two sub-measurements: Systolic Pressure (SP) and Diastolic Pressure (DP), typically read as SP/DP mm Hg. Systolic Pressure is the measurement of the amount of force per unit area that blood exerts when the heart is experiencing Systole, or ventricular contraction. This is the part of the cardiac cycle when pressure is typically highest. Diastolic pressure is measured during the heart in Diastole, or in the beginning of the cardiac cycle, when the ventricles are just beginning to fill with blood. Pressure is typically the lowest during this time. Therefore, blood pressure readings, in addition to being a diagnosis itself, can also reveal a significant amount of information about heart health (Carroll 1988; Levy et al. 2016; Sacks 1979).

Mean Arterial Pressure (MAP) is a commonly used measurement for assessing blood pressure in a patient which is defined in equation 1 (Sacks 1979; Wehrwein and Joyner 2013).

$$MAP = (CO * SVR) + CVP \tag{1}$$

Where CO is cardiac output, a measure of the amount of blood being pumped by the heart, and SVR is the Systemic vascular resistance, or the resistance that must be overcome by the heart to push blood through the circulatory system. CVP is central venous pressure, and is typically negligible in the equation. As we see in this equation, blood pressure, the physical measurement, breaks down into two components: (1) how much blood is being pumped out of the heart and (2) how much resistance is present in the vasculature due to a number of factors including atherosclerotic plaques and vasoconstriction (Aronow 2016; Coca and Camafort 2016; Sesso et al. 2000). Normal blood pressure in humans is 120/80 mm Hg or lower, equating to a MAP of or below 93.3 mm Hg.

Hypertension is clinically diagnosed when two or more diastolic BP measures on at least two subsequent clinician visits is greater than or equal to 90 mmHg or when the average of multiple systolic BP readings on two or more subsequent visits is consistently greater than or equal to 140 mm Hg (Chobanian et al. 2003a; Farooq and Ray 2015; Krakoff et al. 2014; Leung et al. 2016). Risk factors for hypertension include: obesity, sedentary lifestyle, aging, high alcohol intake and insulin resistance amongst others. So, while it is unknown the exact molecular etiology of the disease, there are lifestyle risk-factors which contribute to the development of hypertension (Papademetriou et al. 2011).

Clinical Trials in Hypertension Treatment Research. Hypertension, despite being a chronic disease, and a disease with a relatively long medical history, is still being tested in terms of the current treatment paradigms. A recent clinical trial, called the Systolic Blood Pressure Intervention Trial (SPRINT), was determined to reevaluate the target SP used in clinics for treating hypertensive patients ("A Randomized Trial of Intensive versus Standard Blood-Pressure Control" 2015; Messerli and Bangalore 2016; Ruilope 2016). The study concluded that more intensive management of HTN, via a lower target number for SP, significantly reduced rates of cardiovascular disease, and lowers the risk of death in a group of adults aged 50 years and older ("A Randomized Trial of Intensive versus Standard Blood-Pressure Control" 2015). Previously, the target SP for physicians treating patients was 140 mmHg, but this study showed aiming to get a patient's SP down to 120 can provide numerous health risk improvements ("A Randomized Trial of Intensive versus Standard Blood-Pressure Control" 2015). In terms of curing HTN, medicine and research have much more room to grow, both in the discovery of new and more efficacious treatments, and the clinical implementation of current and new treatment regimens.

Neurogenic Hypertension. Essential hypertension, referred to from now on as hypertension (HTN), is a multi-organ disease affecting the heart, kidneys, vasculature and brain. Neurogenic hypertension, is the most common form of hypertension, and is characterized by increased sympathetic drive, increased Ang II activity and even loss of parasympathetic-mediated cardiac variability, and increased specific inflammation (Esler 2010; Fisher and Paton 2012) (FIG. 1). BP and MAP are measurements based on cardiac output and vascular resistance, two variables that are controlled by the autonomic nervous system and affected substantially by sympathetic drive changes. Sympathetic nerve activity is 100-200% higher in patients with hypertension.

FIG. 1 shows Triangulation of neurogenic hypertension. Inflammation, Angiotensin II, and vascular dysfunction contribute to increased sympathetic nerve activity, leading to hypertension. (Image Credit: Fisher and Paton 2012). (Fisher and Paton 2012). Chronic increase in sympathetic nerve activity is associated with increased cardiac output and increased vasomotor tone.

Baroreflex. This work focuses on two key brainstem regions responsible for blood pressure set point regulation, the nucleus of the solitary tract (NTS) and the rostral ventrolateral medulla (RVLM). Neurogenic mechanisms play a significant role in the development and maintenance of hypertension by resetting the blood pressure set point to a higher level (Barrett and Malpas 2005; Brooks and Sved 2005; Duale et al. 2007a; Y.-W. Li and Dampney 1992; Lohmeier and Iliescu 2013; J. F. Paton, Li, and Schwaber 2001; J. F. R. Paton and Waki 2009; Thrasher 2004, 2005). The primary neuroanatomical circuit affecting the brainstem, which is responsible for blood pressure modulation, is the baroreflex. The baroreflex works is a negative feedback loop modulating blood pressure through enervation between the heart and the brain (Bugenhagen, Cowley, and Beard 2010; R. A. Dampney et al. 2003; Irigoyen and Krieger 1998; Pagani and Lucini 2001).

FIG. 2 depicts the anatomy of the Baroreflex. Afferents from the baroreceptors synapse in the NTS and CVLM and RVLM, where blood pressure set point is modulated. Efferent nerves output to heart and blood vessels to adjust blood pressure as part of this negative feedback loop. (Image Credit: Guyenet 2006).

The molecular sensors, or baroreceptors, are located in the carotid sinus and aortic arch. These receptors are stretch activated, so when the blood vessels expand due to higher blood pressure, the receptors become stretched. Stretching of the receptors increases the firing of action potentials from these cells. Likewise, the opposite happens in terms of action potential firing, if the baroreceptors are not stretched. Since the receptors are directly enervated by cranial nerves XI and X, the activity directly affects the brainstem, through afferent projections to NTS, the nucleus of the solitary tract, and the CVLM and RVLM, the caudal ventrolateral medulla and the rostral ventrolateral medulla, respectively (Guyenet 2006a)(FIG. 2).

Brainstem Angiotensin II in HTN. Angiotensin II signaling is one the best characterized contributors to neurogenic hypertension as it has been shown to increase sympathetic activity, aldosterone secretion, and arteriolar vasoconstriction (Chan & Wong; Paul, Poyan Mehr, & Kreutz, 2006). Today, Ang II signaling pathway small molecule inhibitors comprise two classes of blood pressure management medications mediated through Ang II receptor inhibition and Angiotensin Converting Enzyme inhibition (Farooq & Ray, 2015). In addition, Ang II receptors are highly expressed in the medulla across species (Allen, McKinley, Oldfield, Dampney, & Mendelsohn, 1988; Averill, Tsuchihashi, Khosla, & Ferrario, 1994; Chan & Wong). Microinjecting Ang II into RVLM increases blood pressure and inhibiting the Ang II receptors present in RVLM decrease blood pressure (Averill et al., 1994; Paul et al., 2006).

Based on our prior findings in CNS with elevated blood pressure computational models in which hypertensive inputs drive adaptive gene regulatory network behavior which modulates the production of tyrosine hydroxylase have been built Miller et al. 2010a). These models are also significant in that they focus on molecular processes relevant to Ang II, as implicated in our prior studies. Ang II signaling is prevalent throughout the literature as one facet of hypertension mechanism as it can increase sympathetic activity, aldosterone secretion, and arteriolar vasoconstriction (Y. S. Chan and Wong; Paul, Poyan Mehr, and Kreutz 2006). Many drugs widely used today target Ang II signaling (von Lueder and Krum 2013; von Lueder et al. 2013). Moreover, there are clear contributions of Ang II signaling in NTS in hypertension, as Ang II produced locally in the brain can affect blood pressure regulation independently from circulating Ang II (Arnold et al. 2010; Campbell et al. 1995; Hoffman, Schmid, and Phillips 1977; Senanayake et al. 1994). The NTS contains the highest amount of Ang II receptors in the medulla, and this is evolutionarily conserved (Allen et al. 1988; R. Dampney et al. 2002; Head, Saigusa, and Mayorov 2002; Y. W. Li, Polson, and Dampney 1992). A2 neurons in the NTS abundantly express the AT1R. Microinecting Ang II in NTS and area postrema, which is coextensive with cardiorespiratory NTS, increases blood pressure (Casto and Phillips 1984; J. F. R. Paton et al. 2008).

Specific state of inflammation in HTN. Neurogenic hypertension includes an inflammation-based component. Interleukin-1β (Il-1β) and Tumor Necrosis Factor α(TNF-α), pro-inflammatory molecules are higher in the brainstems of 22-week-old SHR compared to age-matched WKY (Sun et al. 2006). Additional human studies have also found that Interleukin-1 Receptor Antagonist (IL1RN), an anti-inflammatory component of the Il-1 pathway, can have some single nucleotide polymorphisms that contribute to acute coronary syndrome, which further implicates this pathway in cardiovascular disease (Fragoso et al. 2010). Notably, a study of 396 patients, whose health was followed over 6.5 years, found that IL-1β and IL-1RN levels increased in the 32% of subjects who developed hypertension over that time period (Mauno, Hannu, and Esko 2008). In the NTS, the inflammatory state appears to be specific (Gouraud et al. 2011; Waki et al. 2008, 2010b, 2011); however several pro-inflammatory genes in addition to TNF-α and Il-1β have been associated with the development of hypertension such as monocyte chemo attractant protein-1(MCP-1), interleukin-6 (IL-6) and LTB4. Furthermore, high levels of LTB4 in the NTS has been shown to be pro-hypertensive, and blocking its receptor resulted in lowered arterial pressure in SHR (Hendy et al. 2016; Waki et al. 2013a).

Additionally, there are several other inflammation related molecules upregulated in the brain during hypertension, including Chemokine Ligand 5 (CCL5) and Chemokine Receptors 1 and 5 (CCR1, CCR5), inflammation during the development of hypertension is specific to key anatomical regions including NTS and RVLM and Paraventricular Nucleus of the Hypothalamus (Waki, Gouraud, Maeda, & Paton, 2008, 2010; Waki, Gouraud, Maeda, Raizada, & Paton, 2011). Resident CNS immune cells termed astrocytes and microglia are able to mediate a majority of the brain inflammatory processes (Anisman & Merali, 2003; Carmignoto & Gomez-Gonzalo, 2010; De Geyter et al., 2012; Streit, Mrak, & Griffin, 2004).

Vascular dysfunction in neurogenic hypertension. Vascular dysfunction also contributes to neurogenic hypertension (Paton & Waki, 2009; Zubcevic, Waki, Raizada, & Paton, 2011). The blood brain barrier (BBB), which is responsible for protecting the CNS from outside agents, has been shown to deteriorate during the development of hypertension (Biancardi, Son, Ahmadi, Filosa, & Stern, 2014; Espina et al., 2006; Pires, Dams Ramos, Matin, & Dorrance, 2013). Recently, Biancardi et al. showed that peripheral Ang II can gain access to the brain through the leaky BBB, and that this facilitates the development of hypertension (2014). Also, since endothelial cells make up a large portion of the BBB, their role is essential in marinating proper vascular function. But, vascular endothelial cells lining the BBB in hypertension have been shown to have several defects like excess oxidative stress, mediated through eNOS and nitric oxide (Paton & Waki, 2009; Waki et al., 2011). Also, BBB disruption has been shown in the hypothalamus and hippocampus of SHR (Ueno, Sakamoto, Liao, et al., 2004; Ueno, Sakamoto, Tomimoto, et al., 2004).

SHR Serves as a Representative Model of Human Essential Hypertension. Human hypertension is extremely variable and can provide little insight on early stage and developmental processes. In this regard, current evidence indicates that hypertensive strains of rats and susceptible humans have much in common, both phenotypically and genotypically (Atanur et al. 2010; Knight et al. 2003), and the SHR is by far the most widely studied animal model of hypertension. The SHR has the advantage of hypertension developing from a young age over several weeks, which permits study of changes in the pre-hypertensive age, thereby separating effects of high blood pressure from transcriptional processes that may cause hypertension and are altered prior to onset of hypertension. Thus temporal profiling will address the cause and effect regarding the association between transcript changes and blood pressure. The animal model supports the time-series study of the development of hypertension, allowing us to pursue our hypothesis of determining the critical time period of microRNA aberration responsible for the development of hypertension.

microRNAs microRNA biosynthesis and function. microRNAs are an abundant class of small (approximately 22 nt) endogenous non-coding RNAs that direct post-transcriptional regulation of gene expression. There is ample evidence that dysregulation of microRNAs is associated with the pathogenesis of human diseases, including cardiovascular diseases as markers (Wang et al., 2013), specifically in hypertensive patients (Kontaraki et al. 2014) and microRNAs show great promise in affecting hypertension (Pravenec et al. 2014). Disease-associated microRNAs represent a new class of targets for the development of microRNA-based therapeutic modalities, which may yield patient benefits unobtainable by other therapeutic approaches. microRNAs have canonically been thought to down-regulate gene targets by binding with base-pair mismatches to the 3'UTR of an mRNA and causing translational repression or degradation of the mRNA (Breving and Esquela-Kerscher 2010; Clark et al. 2014; Xia et al. 2012). However, microRNAs have also been shown to play a role in increasing the expression of their gene targets by inducing translation by associating with 5'UTR elements of mRNA targets or binding to promoter elements of genes to activate or enhance their transcription or stabilizing mRNAs for facilitated translation (Miranda et al. 2006; Ørom, Nielsen, and Lund 2008; Pasquinelli 2012; Xia et al. 2012). Evidently microRNAs have become seemingly important in regulating diverse cellular processes implicated in both normal tissue function and disease states.

microRNAs are essential in the regulation of normal brain function and development. Since the brain plays a significant role in hypertension, a complex, multigenic disease, understanding the contribution of microRNAs to normal brain development and function is useful when elucidating its origins. microRNAs are essential for proper brain development and function. In development, deletion of Dicer, a key microRNA processing enzyme essential for microRNA biogenesis, via a Wnt1-cre knock-down in neural crest cells of mice exhibited numerous developmental malformations including: tectum and cerebellar malformations and dorsal root ganglia, enteric nervous system and sympathetic ganglia malformations (Huang et al. 2010). In addition, the skeletal structures derived from neural crest cells as well as dopaminergic neuron differentiation were disrupted without the presence of microRNAs (Huang et al., 2010). Dicer can be regulated by microRNAs, specifically miR-107, and can simultaneously regulate neurogenesis by preferential processing of microRNA-9 compared to other more highly expressed microRNAs (Lee, Palkovits, and Young 2006a).

In addition to brain development, there are several examples which highlight the importance of microRNAs in normal brain maintenance following proper development. Global microRNA inhibition by deletion of Dicer can negatively affect both neuron function and astroglia function in the brain. Mouse post-mitotic damage-sensing neurons with Dicer deleted showed upregulation of many broadly expressed transcripts in the dorsal root ganglia, however nociceptor-associated transcripts including the sodium channel Nav1.8 and Runx-1 were down-regulated (J. Zhao et al. 2010). The effects of this dysregulation included attenuated inflammatory pain with decreased excitability of Nav1.8 sensory neurons (J. Zhao et al., 2010). Glial cells also require microRNAs for normal function. Astrocytes require microRNAs for critical functions such as glutamate uptake and antioxidant pathway function (Tao et al., 2011). Required for neuronal function, microRNAs are essential in neurons. Specifically, a well-defined model of post-mitotic, differentiated neurons called Purkinje cells chosen for study due to their well-defined anatomy and electrophysiological properties, displayed degeneration without the presence of microRNAs through deletion of Dicer (Schaefer et al., 2007). Evidently, microRNAs in normal CNS function are essential.

FIG. 3 depicts a summary of literature-derived knowledge of microRNAs in hypertension. In the CNS, prior to DeCicco et al., 2015, one microRNA was characterized in essential hypertension. (Image Credit: Marques et al., 2014). The specific microRNA implicated in increases or decreases are as follows: miR-22 is related to the CNS (brain image at top). Increase in miR-132, miR-145, miR-212, miR-221, miR-222, and Lnc-ANG362 are related to the vascular smooth muscle cells, to the right of the brain image. The clock image depicts Diurnal BP variation, during the active phase, decrease in miR-181a. The Unire and systemic circulation (bottom vial) is related to increase in hcmv-miR-UL112, let-7e, miR-21, miR-92a, miR-130a, miR-195, miR-221, miR-222, miR-4516, decrease in miR_9, miR-27a, miR-126, miR-133a, miR-143, miR-145, miR-150, miR-192, miR-296-5p, miR-4516, with related or possible implications of miR-34a, miR-34b, miR-122, miR-155, miR-449, miR-511, miR-578, miR-608, miR-637, and miR-765. The Kidney is related to increase in miR-132 and miR-212, with increase at the cortex for miR-21, miR-126, miR-196a, and miR-451, with decrease in miR-181a, miR-639, and miR-663, and the Medulla having a decrease of miR-638 and let-7c. Finally, the heart has increase of miR-132 and miR-212, with implication of miR-425.

microRNA potential to contribute to the development of neurogenic hypertension in a cell-type specific manner. Despite many advances in hypertension research, the precise genetic components of this complicated, polygenic disease remain unresolved. Since the advent of the ENCODE project, much attention has now been given to what was previously called, "junk DNA" (Bernstein et al., 2012). Neurogenic hypertension, like other polygenic diseases, benefits from accounting for non-coding RNA such as microRNAs in their disease treatment regimen (Mehta, Jalan, & Mookerjee, 2013; Sanfilippo & Hewitt). To date, there have been several studies analyzing microRNA contribution to essential hypertension. Despite finding several microRNAs in organ systems such as the heart, kidney and systemic circulation system, there have been few studies of microRNA expression in the brain underlying hypertension development (DeCicco, Zhu, Brureau, Schwaber, & Vadigepalli, 2015; F Z Marques, Booth, & Charchar, 2015; Francine Z Marques & Morris, 2012; Morris & Dampney, 2015) (FIG. 3).

Previous data shows that there are several key processes with respective molecular signaling pathways that can be used to contextualize microRNA contribution to neurogenic hypertension. Three main aspects drive neurogenic hypertension: inflammation, Angiotensin II signaling and vascular dysfunction. Inflammation in the context of neurogenic hypertension is confined to a specific set of inflammatory mediators, any of these processes can be localize to distinct cell-types in the brain.

microRNA potential to contribute to the development of neurogenic hypertension in neuron. The neuronal cell-type contribution to neurogenic hypertension is better-established than the contribution of other cell types to this disease. A2 noradrenergic neurons have been shown to be linked to hypertension through several routes including the mechanisms by which anti-hypertensive drugs like clonidine and a-methylnoradrenaline work, as well as attenuation of the baroreflex upon A2 destruction (De Jong and Nijkamp 1976; Talman, Snyder, and Reis 1980; van Zwieten 1975, 1999). More recently, A2 neurons, regardless of their link with the baroreflex, have been shown to play a role in the chronic regulation of arterial pressure in Spontaneously Hypertensive Rats and to contain adaptive transcriptional dynamics (Duale et al. 2007a; Vadigepalli et al. 2012a). In addition to A2 neurons, C1 neurons have been shown to play a role in the development of hypertension. Catecholaminergic C1 cells in RVLM have been shown to contribute to hypertension through chemoreceptor regulation and direct lesions to C1 neurons have been shown to decrease arterial pressure.

Several neuronal phenotypes have been shown to have unique roles in the development of hypertension, and these subtypes even read cellular inputs differently based on their dynamic and adaptable transcriptome in the context of hypertension (Park, Brureau, et al. 2014; Vadigepalli et al. 2012b). Specifically, in a recent work by Park et al., in 2014 NTS neurons stained for FOS, an immediate early gene, to indicate a subset of neurons responsive to acute hypertensive disturbances and Tyrosine Hydroxylase (TH) to indicate catecholaminergic neurons receiving 'higher order' input showed these neurons could be stratified along a continuum of transcript expression, and even change states based on cellular inputs received (Park, Brureau, et al. 2014). Based on the study, we could suggest that not only do the transcripts measured change along a gradient, but that microRNA expression may be coinciding or even contributing to the changes seen in these neurons in the development of hypertension.

There have been several examples of the requirement of microRNA function in neurons to maintain baseline neuronal function. Dysregulation of microRNAs in neurons can lead to several pathologies as well. For example, the let-7 family of microRNAs has been shown to affect several neuronal processes including neuronal differentiation, neuromuscular junction maintenance and circadian rhythm regulation (W. Chen et al. 2014; Sempere et al. 2004; Sokol et al. 2008; C. Zhao et al. 2010). Let-7 family of microRNAs has been shown to Dysregulation of microRNA let-7 family members in neurons has primarily been shown to lead to neurodegenerative disease. Several let-7-mediated mechanisms for neurodegeneration exist currently including let-7 activation of Toll-like receptor 7 which induces neurodegeneration (Lehmann et al. 2012). Let-7g has been shown to protect the blood-brain barrier during neuroinflammatory conditions in mice treated with TNF to induce inflammation. Adherent leukocytes in the cortical microvessels decreased by 3-fold and migrated leukocytes decreased 4-fold upon addition of let-7g (Rom et al. 2015). Additionally, let-7a, let-7c, let-7e and let-7f were shown to be differentially expressed in the NTS of SHR with respect to stage of development of hypertension. SHR develop hypertension spontaneously over time and several members of the let-7 family increase expression over this time course (DeCicco et al. 2015). In RVLM, let-7e is differentially expressed with respect to stage of development of hypertension, but let-7f is differentially expressed with in SHR compared to WKY independent of stage of development of hypertension (DeCicco et al. 2015). Let-7i is predicted to target Agtrap, Il10, Il1rn and cFos, several genes with roles in neurogenic hypertension (DeCicco et al. 2015; Dweep et al. 2011b)

microRNA 124 is highly expressed in the central nervous system (CNS), and shown to enriched in neurons compared to astrocytes, oligodendrocytes and microglia in primary rat cultures (Jovičić et al. 2013; Mishima et al. 2007). In mouse hippocampal neurons, the miRNA transcriptome for miR-124 shows decreased GO processes upon miR-124 inhibition which included cranial nerve development and positive regulation of transcription implicating this microRNA in general functions required for neuron homeostasis (Malmevik et al. 2015). In an inflammatory environment modeled by adding activated macrophage-conditioned media onto neuronal cells, miR-124 protected neurons from losing neurite outgrowth (Hartmann et al. 2015). In neurogenic hypertension, which has a specific inflammatory condition specifically in the brainstem, TNF is shown to be elevated. Therefore, miR-124 in neurogenic hypertension could be protective to neuronal response to inflammation. In addition, miR-124 has is predicted to target AT1R and Angiotensin Receptor Associate Protein (AGTRAP), a negative regulator of Ang II signaling (Dweep et al. 2011a).

miR-7b may also be a potential target in neurons to prevent or treat the development of hypertension. miR-7b is highly expressed in the brain, and has previously been shown to be enriched in neurons compared to other CNS cell types (Jovičić et al. 2013). miR-7b has been shown to be a regulator of Fos, an immediate-early gene which dimerizes with Jun to form the activator protein 1 (AP-1) which regulates transcription of many processes related to hypertension (Lee, Palkovits, and Young 2006b). As mentioned earlier, Fos can be used to indicate neurons receiving direct input from baroreceptors. Upon hyperosmolar stimulation, mice drinking 2% saline solutions displayed relatively high levels of miR-7b expression in the paraventricular nucleus of the hypothalamus, and miR-7b was further shown to diminish FOS translation without affecting transcription. Using miR-7b to target FOS translation may potentially decrease the prohypertensive signaling processes occurring in neurons during the development of hypertension. miR-7b is also differentially expressed in SHR compared to WKY in NTS in a stage-dependent manner which further implicates miR-7b in neurogenic hypertension (DeCicco et al. 2015). Furthermore, our bioinformatics analysis predicted miR-7b to target Il1rn, Alox5, Agtrap, and Agtr1a (DeCicco et al. 2015).

miR-376a, which has been shown to be enriched in neurons compared to other CNS cell types (Jovičić et al. 2013), and has been shown to be differentially expressed in SHR compared to WKY in a stage-dependent manner (DeCicco et al. 2015). miR-376a has many hypertension-relevant predicted targets including regulator of G-Protein signaling 4 (Rgs4), Agtrap, and Fos (DeCicco et al., 2015). Notably, miR-376a has been shown previously to act as a decoy for the transcription factor, NFAT, which highlights the possibility of a significant regulatory role of miR-376a unrelated to its direct mRNA targets (C. Cui et al. 2014).

microRNA potential to contribute to the development of neurogenic hypertension in astrocytes. Astrocytes are a glial cell type that plays a role in mediating inflammation in the brain. They are crucial for maintaining blood brain barrier integrity and critical for maintaining the relationship between neurons and blood flow (Carmignoto and Gómez-Gonzalo 2010). Astrocytes have been implicated in the hypertension via production of leukotriene B4 and other proinflammatory molecules shown to contribute to the development of hypertension (Waki et al. 2013b), and have been shown to be crucial for cardiovascular reflex control (Lin et al. 2013). Due to astrocytes' role in mediating inflammation, we suggest that microRNA regulation of such processes can be crucial to the development of hypertension, specifically through astrocytic contribution.

miR-146a has been shown to be a key regulator of astrocyte-mediated inflammatory response (Iyer et al. 2012). miR-146a has increased expression in epilepsy-associated glioneuronal lesions and has been shown to be enriched in astrocytes compared to other CNS cell types (Jovičić et al. 2013). miR-146a can modulate ll-1β mediated production of Il-6 and Cox2, which have previously been shown to be dysregulated in hypertension. Il-1 signaling has also been shown to be an effect of miR-146a modulation in Alzheimer's disease (J. G. Cui et al. 2010). microRNA-146a can also be transcribed through activation of NfkB, which has been shown to have a higher activation level in SHR (Shang et al. 2009). miR-146a has predicted targets relevant to hypertension including: Il-1 receptor accessory protein (Il1rap), Il-10 receptor antagonist (Il10ra) and Agtrap (DeCicco et al., 2015). Therefore, microRNA-146a serves as a molecular target in astrocytes for affecting the hypertension for in vivo therapeutics.

Another interesting microRNA potentially playing a role in the astrocytic contribution to the development of hypertension is microRNA-155. miR-155 has been characterized to mediate a proinflammatory response in astrocytes (Tarassishin et al. 2011). miR-155 is also highly enriched in astrocytes (Jovičić et al. 2013). miR-155 expression is induced by cytokines and TLR ligands and miR-155 was then shown to be a negative regulator of Suppressor of Cytokine Signaling 1, a negative regulator of cytokine signaling (Tarassishin et al. 2011). This regulatory motif is common in the neuroinflammation literature, putting a unique perspective on microRNAs as direct negative regulators of targets, highlighting that we must account for net positive relationships between microRNAs and proinflammatory signaling. miR-155 has also been shown to have dynamic expression in the development of medial temporal lobe epilepsy similar to TNF-α, which supports preliminary evidence towards a co-regulatory relationship between the two (Ashhab et al. 2013). Predicted targets for miR-155 include Agtrap, Jun, Fos, Il1rap (DeCicco et al., 2015).

microRNA-135a has been previously been shown to be enriched in astrocytes, and has been associated with Alzheimer's associated astrocytic inflammation to the extent of contributing to neuronal viability in this disease (Chu et al. 2015; Jovičić et al. 2013). Importantly, microRNA-135a is dynamically expressed in the development of hypertension, specifically miR-135a has higher levels in SHR at the hypertension onset stage in NTS (DeCicco et al. 2015).

When the predicted targets of miR-135a were assayed in the NTS, several targets with physiological links to the development of hypertension had expression anti-correlated with miR-135a. These targets included Ptgr1, Il1rn and Agtrap, which respectively serve as negative regulators of Leukotriene B4 signaling, Il-1 signaling and Angiotensin II signaling (DeCicco et al. 2015).

While these microRNAs certainly show strong potential as regulators to the development of hypertension in astrocytes, more opportunities for astrocytic microRNAs certainly exist. The microRNAs described here are not a comprehensive list. Our review and interpretation of current literature is a perspective on how to implicate potential microRNA regulators of astrocytic processes that can contribute to hypertension. More generally, these microRNA provide evidence for the need to utilize individual therapeutic treatments. We can evaluate patients Indeed, the results show that individual microRNA implicate and regulate astrocytic processes that contribute to or alleviate hypertension. However, the synergistic effects of multiple anti-miR provide for the novel therapeutic treatments that impact hypertension.

microRNA potential to contribute to the development of neurogenic hypertension in microglia. Microglia, which are glial cells which essentially act as macrophages in the central nervous system, have recently been shown to play a role in essential hypertension (Shen et al. 2015). E. coli lipopolysaccharide induced hypertension induced several proinflammatory cytokines including TNF-a, IL1B and Il-6, and inhibition of microglial activation blunted that effect suggesting microglia as a major source of cytokine production in hypertension (Wu, Chan, and Chan 2012). In the paraventricular nucleus of the hypothalamus (PVN), Angiotensin II induced hypertension is attenuated through application of minocycline, anti-inflammatory antibiotic, and microglial activation is reduced (Shi et al. 2010) As a result, levels of proinflammatory cytokines in PVN were reduced (Shi et al. 2010). Still, there is much research to be done in the characterization of microglia in SHR hypertension.

microRNA-124 contributes to the functional maturity of microglia, and is necessary for their development in vivo (Ponomarev, Veremeyko, and Weiner 2013; Svahn et al. 2015). miR-124 is associated with microglial aging, and has decreased expression when microglia with M1-like activation phenotype mediating pro-inflammatory pathways. The process by which miR-124 is thought to mediate proinflammatory processes is through their disinhibition similar to miR-135a in astrocytes and miR-376a and miR-7b in neurons (Caldeira et al. 2014; Freilich, Woodbury, and Ikezu 2013; Svahn et al. 2015). Furthermore, there is evidence that suggests that miR-124 promotes microglia quiescence when overexpressed, and that this process is mediated through direct inhibition of the transcription factor CCAAT/enhancer-binding protein-a and its target PU.1 (Bird 2011; Ponomarev et al. 2011). Predicted targets for miR-124 include Ptgr1, Rgs4, a regulator of Ang II signaling, Il6r, Il1rap and Il10ra (DeCicco et al., 2015). Evidently, microRNA-124 expression levels may mediate the inflammatory environment in the brainstem during the development of hypertension, and the evidence suggests that this process may work through a disinhibition effect of the microRNA.

miR-155 has previously been characterized extensively in many immunology based pathways, and has recently been shown to be essential for inflammation-inducted neurogenic deficits in microglial activation which can result in disruption of normal hippocampal development (Woodbury et al. 2015).

miR-155 has been shown to target Suppressor of Cytokine Signaling-1 (SOCS1), and as a result may be essential for increasing proinflammatory cytokine expression. Notably, key proinflammatory cytokines shown to be involved in essential hypertension like Il-6, Il-1β, and TNF-α, all had reduced expression levels upon knock out of miR-155 in cultured microglia (Woodbury et al. 2015). Proinflammatory disinhibition mediated through miR-155's inhibition of SOCS1 is a common motif in the recent neuroinflammation literature. Maintaining miR-155 at low expression levels is necessary to maintain functional microglia, and increasing miR-155 levels can cause loss of microglial phenotype (Butovsky et al. 2015). Due to this microRNA's direct role in the regulation of proinflammatory cytokines, and the increase of those cytokines in essential hypertension, miR-155 shows potential to be a molecular driver in essential hypertension and has several relevant targets which could support this role including: Agtrap, Jun and Tnfrsf10b (DeCicco et al., 2015).

miR-200b, a well-characterized microRNA shown to be involved in many cancers and to serve as a biomarker of several diseases including endometriosis, breast cancer, inflammatory bowel disease shows potential to be a microglial microRNA with functional importance in hypertension (W.-X. Chen, Ren, and Shi 2014; Erbes et al. 2015; Jadhav et al. 2014; Rekker et al. 2015). Previously, miR-200b was implicated in CNS diseases as a biomarkers of Alzheimer's disease and as a prognostic indicator of malignant gliomas (Liu et al. 2014; Peng et al. 2013). Only recently has microRNA-200b been shown to be enriched in microglia and to have a microglia specific role in neuroinflammatory modulation (Jadhav et al. 2014; Jovičić et al. 2013). cJun, a member of the AP-1 complex, was shown to be a target of microRNA-200b in microglia, and as a result cJun-N terminal kinase (JNK) was down regulated to show diminished AP-1 signaling as a result of increased miR-200b activity (Jadhav et al. 2014). This is particularly relevant to hypertension, as it is known that AP-1 activity is increased in hypertension, and AP-1 transcription factor distinct dimers maintain a dynamic balance upon Angiotensin II stimulation in NTS (Miller et al. 2010a). Disrupting this balance with miR-200b may lead to the development of hypertension. Other predicted targets of miR-200b with links to hypertension include: Il1rap, Tnfrsf10b and Il6 (DeCicco et al., 2015).

Of note, microRNA-200b does have sexual dimorphic expression, initially starting with high expression levels in P0 rat cortex in females, and eventually becoming more highly expressed in males at P7 (Murphy et al. 2014). Because microRNA-200b has been linked to cerebral ischemia, Implications of this sexual dimorphism could explain sex differences in males and females with respect to stroke occurrences. Hypertension is a risk factor for stroke. So, likewise in hypertension, sex differences in the risk and outcome are well-documented, and miR-200b may pay a role in contributing to such differences (Doumas et al. 2013; Kearney et al. 2005).

Materials And Methods

Animal model: Male, Wistar Kyoto (WKY/NHsd) rats and spontaneous hypertensive rats (SHR/NHsd) obtained from Harlan Laboratories were housed 1 per cage in the Thomas Jefferson animal facility to avoid animal to animal stress from dominance that could affect blood pressure. Each condition had an n=3 or 4 animals. Facilities were maintained at constant temperature and humidity with 12/12 hour light cycles (lights on at Zeitgeber time [ZT] 0). All protocols were approved by the TJU Institutional Animal Care and Use Committee.

Tissue sample punches: There were three time points of interest to this experiment, referred to as prehypertension, hypertension onset, and chronic hypertension. These time points correspond to the age of the rat at the time of sacrifice and mean arterial blood pressure measurements at that time. The prehypertensive stage is 6 to 7 weeks old, hypertension onset is at 10 to 12 weeks, and chronic hypertension occurs around 16 weeks old. At the assigned time of sacrifice, rat was sacrificed via rapid decapitation and brainstems were excised, placed into ice-cold artificial cerebral spinal fluid (ACSF: 10 mM HEPES, pH 7.4; 140 mM NaCl; 5 mM KCl; 1 mM MgCl2; 1 mM CaCl2; 24 mM D-glucose) and secured with agarose for sectioning (4% UltraPure™ low melting point agarose [Invitrogen] in ACSF). 275 mm transverse sections were made with a McElwain Tissue Chopper (Gamshall, England) DVC microdissection with size-matched micropunches (1.25 mm; Stoelting, Wood Dale, Ill.), as previously reported (Khan et al. 2008). Bilateral region punches from one animal were treated as a single sample.

RNA extraction and processing: Total RNA was extracted with the miRNeasy extraction kit (Qiagen, Valencia, Calif.), which captures all RNA greater than 18 nucleotides in length, DNAse treated (DNA-Free RNA kit, Zymo Research, Orange, Calif.), and stored at −80° C. Concentration and integrity were assessed with an ND-1000 (NanoDrop, Philadelphia, Pa.). 100 ng of RNA per experimental condition was processed in the nanoString microRNA assay following manufacturer's protocol. Expression levels of 419 microRNAs were measured from two sections of the brainstem: the NTS and RVLM.

microRNA expression data analysis: nanoString data set has endogenous controls and RNA spike-ins, i.e., additional negative controls from other species purposefully added to the assay to assure that reads were not from non-specific binding, to assure quality. Total count normalization was performed per the manufacturer's protocol for normalizing nanoString data.

The normalized expression level for ith microRNA in jth sample was calculated as:

$$\exp_{ij} = \frac{Count_{ij}}{TotalCount_j} * 100000$$

Where $Count_{ij}$ is the raw count, $TotalCount_j$ is the sum of counts for all microRNAs, positive and negative controls in $j^{th}$ sample, and 100000 is a normalization factor. In essence, this calculation accounts for different amounts of total number of counted molecules across samples (Prokopec et al. 2013). Data was log normalized (base 2), and all microRNAs with maximum normalized expression <6.0 were removed from subsequent analysis. The threshold of 6.0 corresponded to the maximum value of the negative controls including spike-ins. This analysis yielded 197 microRNAs with expression above background detection limits. The data for each anatomical region (NTS and RVLM) was considered separately in statistical analysis. Data was statistically assessed via a two-way ANOVA using stage of hypertension development and rat strain as independent and interacting factors, $p=0.05$, we also confirmed results with Tukey Honest Significant Difference post-hoc testing and corrected using an FDR cut-off of 0.05. For visualization purposes, we followed established approaches for normalizing the expression of each microRNA by subtracting the median expression value of that microRNA across all samples from the same neuroanatomical region.

MicroRNA target prediction: Targets of key microRNAs identified from the nanoString profiling were determined using the miRWalk 1.0 database that provides predicted as well as validated microRNA binding sites for human, mouse and rat (Dweep et al. 2011a). This database utilizes 8 established programs for predicting microRNA target genes and combines these results across three genomes, to improve the sensitivity and specificity. Database settings were altered from default to include both the 5'UTR and CDS for microRNA target matching. Target predictions were filtered based on Gene Ontology and known functional role of in neuronal function. We also used RNA22 to find non-canonical predicted microRNA interactions, and combined these lists to compile all possible microRNA-target putative interactions (Miranda et al. 2006).

High-throughput PCR: Intron-spanning PCR primers and probes for gene target assays, were designed using Roche's Universal Probe Library Assay Design Center (www.universalprobelibrary.com). The standard BioMark™ protocol was used to pre-amplify cDNA samples for 12 cycles using TaqMan® PreAmp Master Mix per the manufacturer's protocol (Applied Biosystems, Foster City, Calif.). qPCR reactions were performed using 3-48.48 BioMark™ Dynamic Arrays (Fluidigm, South San Francisco, Calif.) enabling quantitative measurement of multiple genes and samples under identical reaction conditions. Runs were 30 cycles (15s at 95° C., 5s at 70° C., 60s at 60° C.).

Gene expression data analysis: Targets assayed were chosen based on their role in neuromodulation, inflammation and catecholaminergic regulation from literature and previous unpublished data from this lab. Ct values were calculated by the Real-Time PCR Analysis Software (Fluidigm) and software-designated failed reactions were discarded from analysis. Data was median-centered per anatomical region of the brainstem (NTS, RVLM). An independent statistical analysis was conducted using a 2-way ANOVA with stage of hypertension development and rat strain as independent and interacting factors, $p=0.05$. Pearson correlations between mRNA and microRNA expression were calculated. The microRNA: mRNA pairs with correlation values less than −0.4 or above 0.4 were considered in the downstream network analysis. Hierarchal clustering based on Pearson correlation was performed for each data set using MultiExperiment Viewer part of the TM4 software tool suite (Saeed et al. 2003), and organized graphically with Cytoscape software (Cline et al. 2007; Saito et al. 2012; Smoot et al. 2011).

Results

Figure 4:
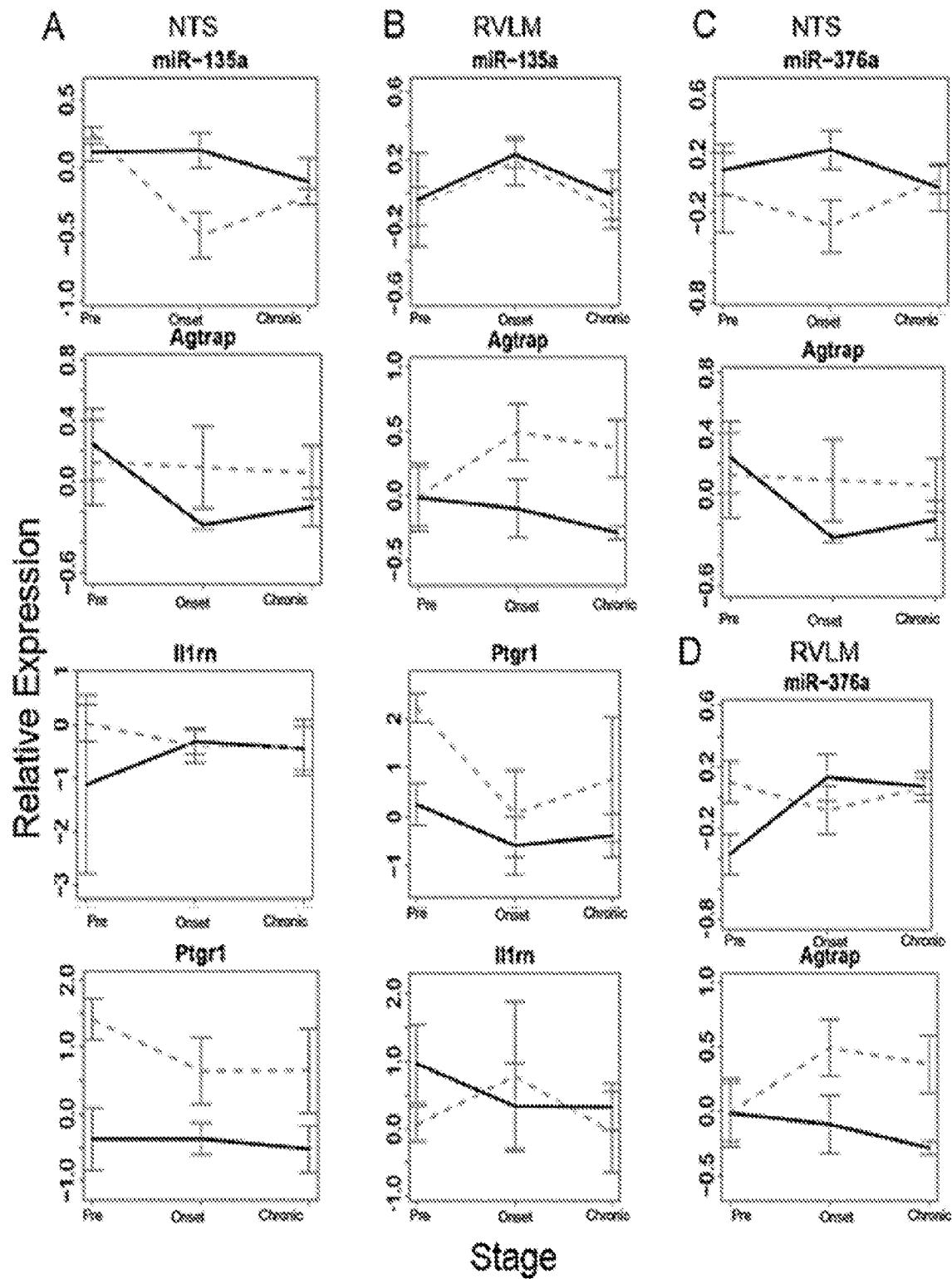

Key Differentially Expressed microRNAs and Putative Transcriptional Targets Comprise Regulatory Networks Contributing to Hypertension Of the stage and strain-dependent microRNAs, two were common between these regions. Interestingly, these two microRNAs were shown to be enriched in different cell types: miR-135a in astrocytes and miR-376a in neurons (Jovičić et al. 2013). We focused the subsequent analysis on this pair of microRNAs and their putative targets. We observed that there were correlational relationships between microRNA and predicted transcript targets when we examined the expression of microRNA: putative target pairs (FIG. 4). Therefore, we assessed all of the microRNA-putative target transcript correlations, and we filtered the microRNA: mRNA network (FIG. 14A-B) to focus on the microRNAs with strain-specific and stage-dependent differential response and their predicted targets (FIG. 5). We mapped the differential expression data as well as the linear correlation between microRNA expression and target transcript levels on to the postulated regulatory network. We filtered the results to include microRNA: mRNA interactions corresponding to absolute correlation values larger than 0.4. Our analysis revealed a similar extent of positive versus negative correlation between the microRNA and predicted target transcript patterns. Correlations across SHR animals differed significantly compared to those of WKY animals. Ultimately, we discovered a pair of microRNAs whose regulatory network showed differences in correlations in hypertension compared to control (FIG. 5). Of note are the inflammation transcripts in NTS for microRNA-135a. There appears to be a much stronger inversely correlative relationship between miR-135a and these transcripts in SHR compared to WKY (FIG. 5).

Based on his analysis in both NTS and RVLM, we constructed a model to show how microRNAs affect hypertension. We focused on a pair of microRNAs, miR-135a and miR-376a, which were (1) differentially expressed between SFR and WKY, in both NTS and RVLM, (2) predicted to target transcripts that play a key role in the development of hypertension and (3) inversely correlated in expression with those key putative targets (FIG. 6). Our model includes miR-135a mediated putative down-regulation of Ptgr1 transcript. The corresponding protein, PTGR1 degrades LTB4 and hence, serves as a negative regulator of leukotriene-mediated inflammation. Similarly, our model includes miR-135a mediated putative down-regulation of Il1rn transcript. The corresponding protein IL-1RA serves as a negative regulator of IL-1 mediated inflammation. In addition, our model incorporates putative down-regulation of Agtrap transcript by miR-135a and miR-376a, likely leading to disinhibition of AT1R signaling.

Discussion

To our knowledge this is the first study that has examined microRNAs and target gene expression in a high-throughput manner from the NTS and RVLM over the course of development of hypertension. We used the SHR animal model that closely mimics several features of the development and chronic state of human hypertension. Through an unbiased global microRNA expression analysis, we found extensive differential expression of microRNAs in these two key brainstem regions during the development of hypertension. Therefore, these results serve as the closest human model, and are highly correlative based on the highly conserved, if not identical miR and anti-miR structures and sequences. We correlated these changes to their putative gene expression targets with a focus on how the changes evolve over time (dynamics). We developed a regulatory network model that connects changes in microRNA expression to modulation of key transcript levels participating in inflammation and Ang II signaling to drive hypertension development. The network contains a novel double-negative regulatory motif in which up-regulated microRNAs likely down-regulate inhibitors of inflammation and Ang II signaling processes.

The recent literature offers abundant evidence for "neurogenic hypertension" in which the central neuronal mechanisms of blood pressure regulation play a key role, in particular autonomic structures in the brainstem, the nucleus of the solitary tract (NTS) and the rostral ventrolateral medulla (RVLM). Fortunately, current evidence indicates that hypertensive strains of rats and susceptible humans have much in common, both phenotypically and genotypically with respect to neurogenic contributions to hypertension (Atanur et al. 2010; Knight et al. 2003; Matsumoto et al. 1991; Sun et al. 2006), and the SHR is by far the most widely studied animal model of hypertension (Pravenec et al. 2014). The SHR has the advantage of hypertension developing from a young age over several weeks, which permits study of transcriptional changes in the pre-hypertensive age, thereby separating effects of chronic high blood pressure from transcriptional processes that may lead to hypertension during the prehypertension stage. Thus, temporal profiling addresses the cause and effect regarding the association between transcript changes and blood pressure. The animal model supports the time-series study of developmental vs. chronic gene expression changes, which is beneficial for clarifying an optimal therapeutic intervention time point.

Our results highlight the stage-dependent dysregulation of molecular networks in the development of hypertension. These findings are consistent with observations indicating a stage-dependent role for Ang II signaling processes in driving hypertension. Blocking Ang II mediated AT1R signaling at a young age (4-8 weeks of age) in SHR model, corresponding to intervention at the prehypertension stage, prevented development of hypertension even up to 48 weeks later (Baumann et al. 2007). These results, together with our findings, implicate the prehypertensive stage as a key period in the development of hypertension. Our results uncovered a microRNA-mediated regulation as potentially underlying this stage-dependent sensitivity. The microRNAs identified in our study could serve as novel targets for manipulation to influence the Ang II signaling and interfere with the development of hypertension.

Our results suggest that microRNA regulation and downstream effects on putative target transcript levels vary by brainstem region during development of hypertension. RVLM showed differential microRNA expression prior to the onset of hypertension, at an earlier stage than was observed in the NTS, which showed microRNA expression changes during the hypertension onset stage. The functional consequences of these distinct stage-dependent responses need to be interpreted through the location and role of these brainstem nuclei in the blood pressure control circuit. The NTS is known to be the primary site of cardiorespiratory regulatory integration (Affleck, Coote, and Pyner 2012; Campagnole-Santos, Diz, and Ferrario 1988; R. K. Chan and Sawchenko 1998; Colombari et al. 2001; Michelini 2007; Rogers, Paton, and Schwaber 1993; Rogers et al. 1996). The RVLM. receives inhibitory projections from the caudal ventrolateral medulla. Disruption of these inhibitory projections leads to the development of hypertension (S. K. Agarwal and Calaresu 1990; R. K. Chan and Sawchenko 1998; Y. S. Chan and Wong; R. A. Dampney et al. 2003; Geraldes et al. 2014; Granata et al. 1985; Huber and Schreihofer 2011). The RVLM is crucial in tonic and reflexive regulation of arterial pressure, and it has been shown to contribute to elevated sympathetic nerve activity and mean arterial pressure in obese Zucker hypertensive rats (Huber and Schreihofer 2011). Studies have shown that RVLM-enhanced angiotensinergic activation and reduced GABAergic inhibition contributes to hypertension in these rats, and the low levels of microRNAs observed in our results are consistent with putative microRNA-mediated regulation of these processes (R. K. Chan and Sawchenko 1998; Huber and Schreihofer 2011; Muratani, Averill, and Ferrario 1991). Our results suggest that by the time increases in mean arterial pressure are seen in the hypertension onset stage, it is likely that the aberration in the molecular networks have already occurred in the RVLM. is interesting to speculate whether the processes that are disrupted earlier in RVLM lead to changes in the microRNA expression and corresponding dysregulation of transcript levels in the NTS at a later stage. In that regard, a question arises as to whether the NTS microRNA network expression changes at hypertension onset are compensatory or are further advancing the pathology leading to aberrant wiring across the baroreflex control circuit.

We interpret the microRNA and putative target gene expression correlations observed in our results as signatures of the underlying mechanistic relationships that are candidates for further experimental testing. Our results show that the microRNA and putative target gene expression correlations differ significantly between the SHR and INKY animals, indicating differences in the underlying regulatory networks between the two genotypes. We prioritized a subset of these relationships based on inverse correlation between microRNAs and putative targets for constructing a regulatory network. The positive correlations observed in our results could arise due to multiple possibilities. For instance, microRNAs have been shown to up-regulate certain targets by stabilizing the mRNAs (Pasquinelli 2012). Additionally, the microRNAs could be affecting transcript levels in a positive manner indirectly by down-regulating a negative regulator of the transcript.

In order to examine the effects of microRNA changes on the molecular pathways implicated in hypertension, such as angiotensin II signaling and inflammation, we employed bioinformatics analyses to predict regulatory targets corresponding to these pathways. From the cohort of differentially expressed microRNAs, we examined two cell type specific microRNAs in additional detail: miR-135a, which is enriched in astrocytes, and miR-376a, which is enriched in neurons (Jovičić et al. 2013). Given the expected cell-type enrichment, it is important to localize the correlations between microRNAs and putative targets to specific cell types, as these may be masked or altered when considering tissue-scale samples that we employed in the present study. Literature evidence points to likely cell-type specificity of these pathways, for example, AT1R signaling in neurons and leukotriene metabolism in astrocytes (Okaty, Sugino, and Nelson 2011; Waki et al. 2013a). Both microRNAs showed significant differences in expression in NTS and RVLM, and are predicted to target transcripts and networks associated with high blood pressure. We developed a regulatory network model containing these two microRNAs and putative target transcripts miR-135a is particularly enriched in astrocytes relative to neurons, oligodendrocytes, and microglia (Jovičić et al. 2013). Our target prediction and expression correlation analysis revealed that miR-135a is likely to act by down regulating Ptgr1 transcript, which has been shown to be down-regulated in adult SHR rats compared to WKY rats (Waki et al. 2013a), which is consistent with the higher expression of miR-135a observed in our data. Thus, we have hypothesize that miR-135a down regulates the Ptgr1 expression to increase the levels of a key pro-inflammatory leukotriene LTB4, likely leading to the development of hypertension. High levels of LTB4 in the NTS have been shown to be prohypertensive, and blocking LTB4 receptor resulted in lowered arterial pressure in SHR (Waki et al. 2013a). In RVLM, proinflammatory cytokines have been shown to be elevated (D. Agarwal et al. 2011), and microinjecting pentoxifylline, an anti-inflammatory drug whose mechanism is partly mediated through leukotriene inhibitor has been shown to lower blood pressure in LPS-induced hypertensive rats (Wu, Chan, and Chan 2012). Our analyses also pointed to additional routes of influence via miR-135a down-regulation of Il1rn, a key anti-inflammatory regulatory player. IL-1RN has been shown to exhibit an anti-inflammatory effect via IL-1 signal attenuation (Goehler et al. 1997). Furthermore, the levels of IL-1, a proinflammatory molecule, are higher in the brainstems of 22-week-old SHR compared to age-matched WKY (Sun et al. 2006). Additional human studies have also found that Il1rn has single nucleotide polymorphisms that contribute to acute coronary syndrome, which further implicates this gene in cardiovascular disease (Fragoso et al. 2010). In our results, Il1rn is expressed at higher levels in WKY than in SHR. We predict that the down-regulation of Il1rn transcript via miR-135a contributes to the development of hypertension by disinhibiting an inflammatory signal mediated through IL-1. Another hypothesized route of miR-135a influence predicted by our computational analysis is through modulation of Ang II signaling. NTS contains the highest amount of Ang II receptors in the medulla, and this is evolutionarily conserved (Allen et al. 1988; R. Dampney et al. 2002; Head, Saigusa, and Mayorov 2002; Y. W. Li, Poison, and Dampney 1992). RVLM also contains a high amount of Ang II receptors compared to the rest of the medulla (Granata et at 1985; Head, Saigusa, and Mayorov 2002). miR-135a putative mediation of Ang II signaling occurs via down-regulation of Agtrap, angiotensin II receptor associated mRNA. AGTRAP protein is a key down-regulator of the angiotensin II receptor type 1 (Daviet et al. 1999). Based on this target prediction and expression correlation, we postulate that miR-135a may be down-regulating a negative regulator AT1R, therefore increasing Ang II signal transduction, and leading to blood pressure elevation. However, alternate pathways may also be impacted, and thus we are not held to these predicted pathways as highlighted herein.

In contrast to miR-135a, miR-376a is highly expressed in neurons relative to astrocytes, microglia and oligodendrocytes (Jovičić et al. 2013). miR-376a was one of the highly expressed microRNAs in our results with whole tissue samples. Based on the target prediction analysis and transcript and microRNA expression correlation results, we hypothesize that the neuron-enriched miR-376a could act via targeting Agtrap to disinhibit Ang II signaling in NTS In the rat transcript of Agtrap, there appears to be only one miR-376a predicted binding site in the 3'UTR beginning at the 5' end nucleotide 1646 based on RNA22 predictions; however, in the human there is one in the 3' UTR beginning at 936 from 5' end of the transcript, and an additional predicted binding site in the 5' UTR beginning at nucleotide 53 from the 5' end on the transcript (FIG. 14A-B). miR-135a has more predicted binding sites on the Agtrap transcript than miR-376a. miR-135a has two predicted target sites on Agtrap, both in the 3' UTR beginning at nucleotide 1125 and 1509 from 5' end. In contrast, the human Agtrap transcript has five predicted target sites for miR-135a-1, all of which are located in the 3' UTR at locations: 714, 749, 839, 906, and 961 from 5' transcript end. Notably, there is no competition between these two microRNAs to bind Agtrap as none of the predicted binding sites overlap.

Our results also highlight several additional microRNAs differentially expressed between the SHR and WKY rats and correlated with their downstream transcript targets, providing a cadre of putative microRNA regulated pathways underlying the development of hypertension. Our correlation analysis pointed to several putative influences of microRNA changes aside from the canonical direct targeting via seed region base pairing in the 3' UTR. For instance, miR-135a expression was inversely correlated with that of Ace, which was not predicted to be a direct target of miR-135a in our analysis. This suggests a regulatory network interaction involving multiple intermediate steps, or alternatively, potential novel direct targeting of Ace by miR-135a. Additional experiments involving manipulation of microRNAs in disease models are required to further develop the putative target transcript correlations into a mechanistic causative role for microRNAs in the development of hypertension. Our results identify several microRNAs, including those with a cell type specific role, for therapeutic use.

Essential hypertension has a neurogenic component, which is now established to be characterized by a specific state of inflammation, and dysregulated Angiotensin II (Ang II) signaling (Veerasingham and Raizada 2003; Waki et al. 2013a; Zubcevic et al. 2011). Brainstem regions including the nucleus of the solitary tract (NTS), or the principle integrative center for blood pressure control, the rostral ventrolateral medulla (RVLM), caudal ventrolateral medulla and others have shown to be affected (Colombari et al. 2001; Geraldes et al. 2014; Hirooka, Potts, and Dampney 1997; Michelini 2007; J. F. R. Paton et al. 2008; Waki et al. 2008; Zanutto, Valentinuzzi, and Segura 2010). The NTS is essential in blood pressure set point control. Blood pressure has previously been shown to be renormalized upon several interventions into NTS, including antagonizing the Ang II signaling pathway, and blocking the leukotriene B4 receptor (Averill et al. 1994; Hendy et al. 2016; Lu et al. 1998; von Lueder and Krum 2013; Waki et al. 2013a).

Recently, a global microRNA study was performed to evaluate the microRNA expression landscape in both NTS and RVLM in SHR and age-matched WKY controls (DeCicco et al. 2015). The study provided insight into a pair of microRNAs that might act as gene-regulatory hubs controlling both the Angiotensin II and Leukotriene B4 signaling pathways. In NTS, both microRNAs were expressed at higher levels during the development of hypertension in SHR corresponding to 10-12 weeks of age, when physiological increases in blood pressure are first observed (DeCicco et al. 2015).

Each microRNA has been previously characterized in other disease models, but neither have been implicated in hypertension as potential therapeutics. microRNA-135a has been shown to be expressed in the brain, and to be enriched in astrocytes compared to other CNS cell types including neurons, microglia and endothelial cells (Jovičić et al. 2013). Classically, microRNA-135a has been implicated in several cancers including colorectal, prostate, melanoma and glioma (Deng et al. 2015; Hemmesi et al. 2015; Kroiss et al. 2015; Ren, Li, and Tu 2015; Zhang et al. 2016; Zhou et al. 2012). Additionally, it has also been implicated in inflammatory conditions including mast cell and allergen-induced inflammation, pelvic inflammation suggesting it has influence on inflammatory pathways in these systems (Deng et al. 2015; Yeruva et al. 2014). microRNA-135a was implicated in the leukotriene B4 pathway via its regulation of the 5-lipoxygenase activating protein (FLAP) in hypoxia (Gonsalves and Kalra 2010), and miR-135a was anti-correlated to its predicted targets in a regulatory network that impacts both the Ang II pathway and the Leukotriene B4 pathway (DeCicco et al. 2015).

miR-376a has also been shown to be expressed in the brain, and particularly enriched in neurons compared to the other cell types (Jovičić et al. 2013). microRNA-376a was implicated in hypertension through its predicted modulation of the Angiotensin II pathway (DeCicco et al. 2015). Aside from its implication in neurogenic hypertension, microRNA-376a has been shown to be involved in apoptosis and DNA damage pathways (Formosa et al. 2014; Zheng et al. 2012), and it was also been characterized as a biomarker for type 2 diabetes and obesity (Pescador et al. 2013).

Since both of these microRNAs displayed increased expression levels in NTS at the hypertension onset stage, corresponding to the 10-12 week age range, antagonizing these microRNAs at this critical time period would be expected to reduce the blood pressure in SHR via decreasing the activity of the Ang. II and Leukotriene B4 signaling pathways (DeCicco et al. 2015; B. J. Morris and Dampney 2015). The time period where these microRNAs display expression differences corresponds to a critical time period previously identified where intervention with losartan, a partial Angiotensin II receptor antagonist, acutely attenuated hypertension in rats for up to a year (Baumann et al. 2007). Moreover, microRNAs have been delivered intranasally in pre-clinical studies to act in the central nervous system, increasing their therapeutic value as CNS drugs (Deng et al. 2015). Therefore, the primary aim was to determine whether acute inhibition of miR-135 and mir-376a combined, or inhibition of miR-135a and miR-376a alone would reduce blood pressure and restore molecular signaling network balances in SHR.

Inhibition of microRNAs 135a and 376a in vivo via intracerebroventricular injection attenuates hypertension in rats at the hypertension onset stage (FIGS. 8A, 8B).

Blood pressure in the SHR is generally increasing between 10-12 weeks of age, yet a single ICV injection of a cocktail of anti-miR-135a and anti-miR-376a LNA at 10 weeks of age led to significantly decreased blood pressure over this same time frame (FIG. 8A,n=5 for each group). One week after LNA cocktail injection, the mean arterial pressure (MAP) decreased from an average of 165±2.5 mmHg to an average of 103±15.7 mmHg (mean±SEM), a 37.5% decrease from baseline (p<0.001). Two weeks after injection of the LNA cocktail, the MAP remained significantly decreased, with an average of 117±5.6 mmHg, a 29.1% decrease from baseline (p<0.01). These changes in MAP were found to be statistically significant using a nested ANOVA on the repeated consecutive blood pressure measurements for each animal with Tukey honest significant difference. Injection of a scrambled LNA oilgo not targeted towards any known miRNA or mRNA transcripts (miR-CURY LNA inhibitor control) showed no significant changes from baseline nor from no surgery control SHR animals from the same cohort.

In contrast the blood pressure altering effects of the anit-miR135a and anti-miR376a cocktail on SHR, there were no significant effects on the blood pressure of WKY animals. Age-matched WKY rats that received the same cocktail of anti-miRs showed stable MAP averaging 99.0±8.9 mmHg at baseline and 99.5±7.8 mmHg one week post injection (FIG. 8B, n=3 for each group). The scrambled LNA also did not show an appreciable effect on MAP, averaging 98.4±8.2 mmHg at baseline and 101.5±5.7 mmHg (mean±SEM).

Individual microRNA inhibition shows contribution of microRNA-135a and microRNA-376a independently to blood pressure attenuation (FIG. 10)

After determining that an injection of the combined LNA cocktail composed of both anti-miR-135a and anti-miR-376a had a significant effect on blood pressure, we wanted to determine what the contribution was of each LNA and to get a sense if the effect was additive or synergistic. It was expected that either single anti-miRNA would have a smaller effect than the two combined and that this effect size would be more indicative of a synergistic rather than an additive mechanism. This is due primarily to the hypothesis that the anti-sense LNA oligos are disrupting miRNAs that are positioned to affect several genes in a network. When considering an effect that is most likely an emergent property of the network interactions, it is more likely the number of nodes perturbed will have a nonlinear relationship with the magnitude of the overall effect of that perturbation.

SHR rats were injected with either anti-miR-135a or anti-miR-376a at 10 weeks of age. The MAP was reduced by 15±4.4 mmHg for the anti-miR-135a group and 16±7.9 mmHg for the anti-miR-376a group, $p<0.05$ for each using a nested ANOVA with Tukey HSD (FIG. 10). These decreases are more modest than the 62 mmHg reduction seen with the cocktail composed of the two LNAs over the same developmental time period.

Effects of anti-miR-135a and anti-miR-376a cocktail on gene expression in the NTS show a shift towards a WKY-like expression profile, without actually recapitulating it (FIG. 11 C). Using a cohort of 19 genes related to inflammatory processes, angiotensin signaling, and key transcription factors, it was possible to show slight perturbations in the gene regulatory networks of the NTS were indeed caused by injection of the LNA cocktail, but only in SHR and not in WKY. The minimum spanning tree (FIG. 11C) based on the expression values of this cohort of 19 genes shows individual laser captured NTS samples taken across all animals in the LNA injection study. Both the separates of the WKY and SHR cohorts from each other is notable and expected given the myriad of known differences in gene expression in the NTS of each. The effect of the cocktail on SHR shows a shift toward the WKY gene expression pattern, without fully recapitulating it. The effect of the cocktail on WKY is not distinguishable from the negative control scramble LNA, which mirrors the physiology observed.

The gene expression values themselves also reflect a general trend of the cocktail moving SHR expression patterns to be more in line with WKY, as shown in FIG. 11C, specifically in genes with an asterisk. Not all of these genes are putative targets of either miR-135a or miR-376a, but are instead involved in networks with constituents that are involved and are good reporters of functional data. While none of the changes shown meet the traditional p value cut-off of 0.05, primarily due to the small effect size, the overall trend and MST show that there is a clear shift in expression pattern that is derived from cumulative small adjustments in gene expression level.

Discussion

When considering the network of organs and body systems that drive and perpetuate hypertension, there is no doubt that the NTS is a node with vital connectivity and a large amount of control potential. Through its role in interpreting interceptive inputs from the entire body and translating that into autonomic function via the parasympathetic and sympathetic outflows, it becomes an attractive target for manipulation. Past studies have shown that manipulations affecting only the NTS alone are sufficient to ameliorate hypertension in the SHR model (REFS). Many of the pharmacological interventions that show clinical efficacy in lowering blood pressure in hypertensive patients work at many different sites of action in parallel, even if the presumed mechanism of action is narrowly defined. Consider, as an example the angiotensin receptor blocker losartan, whose mechanism of action generally is defined as working on angiotensin-1 receptors in the heart, vasculature, and kidney, but which also has effects in the brain that were not originally well-defined. Pharmacological interventions also have the tendency to drive a very large direct effect on only one receptor or protein, which then has downstream consequences that lead to renormalizing blood pressure. When all of the network interactions are considered both between organs as well as within organ tissue at a molecular level, it seems this network behavior can be shifted by a large, but narrow perturbation such as renal denervation or taking a drug that blocks angiotensin receptors.

The use of microRNAs, however, does not lead to large, narrow changes in the network. Any given microRNA has hundreds to thousands of putative binding sites on known mRNA transcripts (REFS) and plays only a small role in the overall expression levels of that transcript (REFS). Rather than thinking of microRNAs as gene expression modulators, it would perhaps be more functionally useful to think of them as gene network tuners. Through small, broad changes in networks, it is possible to retune the network behavior that may lead to distinct physiology. It is clear from FIGS. 8A and 10 that such physiological outcomes are possible. What remains is picking apart the molecular mechanisms that drive this behavior. This will not likely be accomplished through the traditional series of siRNA or genetic knockout models. A network-based approach will be required including the measuring of hundreds to thousands of transcripts and mathematical techniques to deconvolute the non-linear effects. These initial results in examination of gene expression suggest that there are not likely very large changes in any gene transcript that result from knockdown of microRNAs, but that there is vast number of distinct transcripts that are affected. This is in line with the theory set forth recently by Lander et al. stating that physiological function is the product of network interactions and that small changes in such networks can lead to drastically different physiological outcomes (Wilkins et al. 2016).

Many cases of essential hypertension are refractory to current treatment paradigms. There are several treatments that each work for a cohort of patients, but not all and that much of the time the relief from hypertension is not permanent. If essential hypertension is a disease that follows from a set of network properties, then it is possible that adaptions within this network could lead to recalcitrant high blood pressure. By treating one or another aspect of the network while leaving the rest unaltered may not be a large enough perturbation in order to generate a new network state. However, it is possible that several small perturbations in mRNA levels across several genes are enough to push the network into a new state. If this is enough to cure hypertension has yet to be demonstrated, but the results here suggest that such an approach may have value and should be carefully considered as a means of treating complex diseases that emerge out of systems of network interactions.

Accordingly, based on the data, individual therapeutic treatments with anti-miR 135a or anti-miR-376a provide for a reduction in MAP. However, while these are individually effective, the synergistic effect of the combination of both 135a and 376a leads to a much greater reduction in MAP.

In a preferred embodiment, a method of treatment of hypertension comprises administration of an effective amount of an anti-miR 135a, anti-miR-376a or a combination thereof.

A possible course of treatment provides for a single therapeutic, either 135a or 376a for a pre-determined amount of time. Evaluation of MAP continues throughout the therapeutic treatment. Should MAP fail to sufficiently fall to safe levels, then a combined therapy can be utilized. In this manner, the treatment may be sufficient with a single therapeutic, and saving the combined therapeutic for a later time, should the first therapy be insufficient. This allows for a tiered approach to treatment.

A method may comprise providing a therapeutic treatment for a predetermined amount of time, comprising one of an anti-miR 135a or anti-miR-376a, at a dose sufficient to drop MAP; determining whether said drop in MAP is sufficient to reduce hypertension to a safe level, between 110 and 65 mm Hg; providing a second therapeutic comprising both anti-miR 135a and anti-miR-376a if the MAP does not fall into the category of 110 to 65 mm Hg. The administration of the first or second therapeutic can continue for a period of 7-30 days, and review whether the MAP stays in a safe zone, or the therapeutics may continue for a longer, possible indefinite period for control of hypertension.

Materials and Methods

Animal Model: Male, Wistar Kyoto (WKY/NHsd) rats and spontaneous hypertensive rats SHR/NHsd) obtained from Harlan Laboratories were housed 1 per cage in the Thomas Jefferson animal facility to avoid animal to animal stress from dominance that could affect blood pressure. Facilities were maintained at constant temperature and humidity with 12/12 hour light cycles (lights on at Zeitgeber time [ZT] 0). All protocols were approved by the TJU Institutional Animal Care and Use Committee.

Stereotaxic Cannulization and Injection: The 25 uL injection consisted of a 1:1 ratio of anti-miR-376a Locked Nucleic Acid (LNA, Exiqon) 10 uM solution in artificial cerebrospinal fluid in combination with anti-miR-135a LNA in 10 uM solution, this condition was considered AM-Combo. Scrambled, an antisense oligonucleotide, LNA and no surgery conditions were also assayed. Sham surgeries, where cannulas were inserted and an empty needle was placed for the duration of the corresponding injection time were also performed. The rats were anesthetized by isofluorane inhalation and placed in a stereotactic instrument (Stoelting Co., Wood Dale, Ill., USA), positioned, and the incision site appropriately prepared. A small incision was made, and the skull was then exposed and cleaned and a small burr hole was drilled using a dental drill or Dremal rotary tool, and cannula was mounted with dental cement. The LNAs were injected using a Hamilton syringe with a 35-gauge needle (Reno, Nev., USA) over a 30 minute time period into the fourth ventricle using the coordinates: 11.3 mm caudal to bregma, 0.5 mm lateral to sagittal suture, and 14 mm in depth. The incision was closed and the rats were placed on an isothermal pad at 37° C. and continuously observed following surgery until recovery. Topical analgesic was applied immediately following the surgical procedure and as needed thereafter.

In Vivo Manipulations: Animals evaluated included two age groups. (1) Onset of Hypertension: Set one was comprised of 12 week old SHR and WKY animals for the hypertension onset experiments. Six SHR were injected with AM-Combo, 3 were injected with AM-376a, and three were injected with AM-135, and four SHR were injected with scrambled oligonucleotide control. Two SHR underwent sham surgery where a cannula was placed, but no injection was given. Four SHR were maintained with the cohort as untreated. Four WKY were injected with AM-Combo and four were injected with scrambled negative control. Three WKY animals underwent sham surgery and four were kept untreated. Blood pressure was measured every other day for one week post injection. Animals were sacrificed two weeks post injection. Part of this cohort of animals was tested in a double-blind study (n=3 per condition in SHR and WKY). The individual injections were evaluated as an independent experiment. (2) Chronic Hypertension: Set two was comprised of 30 week old SHR and WKY animals for the chronic hypertension experiments. Six SHR were injected with AM-Combo and four were injected with scrambled control. Four SHR animals underwent sham surgery. Three SHR were maintained with the cohort as untreated. Six WKY animals were injected with AM-Combo, and four were injected with scrambled control. Four underwent sham surgery and three were kept untreated. Blood pressure was measured once a week for four weeks. Animals were sacrificed four weeks post injection.

Tail Cuff Blood Pressure: The rats were trained for two days to adapt to the tail-cuff blood pressure measurement system. Following the training period, conscious rats were individually placed into an acrylic restraining cage on a warm plate (38-40° C.). The blood pressure was determined by using the indirect tail-cuff method [insert reference]. Briefly, when the cuff pressure was elevated to cut off the blood flow by inflating a bulb, no pulse was detected by a pneumatic sensor (CODA. Houston, Tex.), which was placed along the tail artery. When the cuff pressure was reduced at the rate of 20 mmHg/s to allow the blood flow, the resulting pulse was detected by the pneumatic sensor. Systolic and diastolic pressures of rats were determined at least 3 times within an interval of 30 min.

Sample Collection: At the end of each time course of treatment, rats were sacrificed via rapid decapitation, and brainstems were excised and placed into Optimal Cutting Medium (OCT) (TissueTek, QIAGEN, Valencia, Calif.) and flash-frozen at −80 degrees Celsius for cryosectioning. Brainstem samples were taken throughout the intermediate levels of the NTS co-extensive with the area postrema using a cryostat.

Laser Capture Microdissection (LCM): Laser capture microdissection was used to obtain precise regional samples from NTS. To preserve RNA integrity, dehydration was performed within 20 minutes. Slides were fixed in cold Acetone with 1% Hydrogen Peroxide (Sigma-Aldrich) for 1 minute, then permeabilized and rinsed in Phosphate Buffered Saline for 30 seconds. Slides were washed in PBS and dehydrated in graduated ethanol concentrations followed by two immersions in Xylene for 1 minute and 5 minutes, respectively. The LCM process was performed using Arcturus XT LCM. The NTS was localized using anatomical landmarks, and was lifted as a region using the laser capture dissection method. 2-4 bilateral NTS sections were pooled per each cap, and sections were lysed direction on the cap, and cooled on ice before −80 degree Celsius storage.

Cell culture of CTX-TNA2 astrocytes and transfection: Cells were obtained directly from ATCC, and passages 6-10 were used for experiments. Per ATCC protocol, cells were maintained in DMEM supplemented with 10% (V/V) FBS, 1% (V/V) penicillin and streptomycin. The cultures were transfected 24 hours after plating with an LNA for microRNA-135a purchased from Exiqon. Cells were evaluated morphologically to assure phenotype maintenance.

Cell Culture RNA Preparation: At relevant time point post transfection, cells were harvested through direct application of TriZOL using the Direct-zol RNA MiniPrep kit (Zymo Research, Orange, Calif.). This kit captures all RNA greater than 18 nucleotides in length, and RNA was stored at −80° C. Concentration and integrity were assessed with an ND-1000 (NanoDrop, Philadelphia, Pa.). RNA was used for microRNA and mRNA simultaneous qPCR application.

microRNA and mRNA simultaneous high-throughput quantitative PCR sample preparation: microRNA expression levels and transcript expression levels were measured using a sequential reverse transcription reaction from one LCM-obtained or RNA sample. Samples of bilateral NTS obtained from LCM and lysed on cap were directed into universal reverse transcription reaction to reverse transcribe all mRNA (Vilo, Life Technologies). Following a universal reverse transcription, the sample underwent reverse transcription for specific microRNAs (miR-135a and miR-376a) using the Taqman detection system to increase specificity of future quantification. Due to limited RNA amount, one universal preamplification step was performed using primers for genes of interest and microRNAs of interest using TaqMan® PreAmp Master Mix per the manufacturer's protocol (Applied Biosystems, Foster City, Calif.). Finally, genomic DNA was digested and genes and microRNAs were measured using high-throughput qPCR or standard qPCR.

High-throughput qPCR: For the transcript measurement and quantification for the previously prepared sample, qPCR reactions were performed using a combination of 96.96 and 192.24 BioMark™ Dynamic Arrays (Fluidigm®, South San Francisco, Calif.) enabling quantitative measurement of multiple mRNAs and samples under identical reaction conditions (Spurgeon et al. 2008). Each run consisted of 30 amplification cycles (15s at 95° C., 5s at 70° C., 60s at 60° C.). Ct values were calculated by the Real-Time PCR Analysis Software (Fluidigm). Intron-spanning PCR primers for every assay were designed (not shown) and tested for proper amplification before use on a BioMArk array. microRNAs were detected using a standard ABI 7000 qPCR platform using Taqman standard chemistry.

Data Normalization and Analysis: We followed the methods we have previously utilized for high-throughput transcript level analysis (DeCicco et al. 2015). In brief, assays and samples failed by software due to technical noise were discounted for downstream analysis, and data was normalized by median gene expression levels across 24 genes in the case of 192.24 dynamic array and across 96 genes in the case of the 96.96 dynamic array. An independent statistical analysis was conducted using a one-way ANOVA with treatment as the variable, p=0.05. Tukey post-hoc testing was employed to account for multiple testing comparisons.

Results

SHR and WKY animals were injected with LNA-Combo directly into the IVth intracerebral ventricle (ICV). Due to flow conditions of cerebral spinal fluid from rostral to caudal, we expected the LNA to be able to penetrate appropriate medial NTS levels in the brainstem. Previously, ICV injections have been used to alter gene expression levels in brain tissue for several diseases including epilepsy and stroke and ischemic brain injury (Jimenez-Mateos et al. 2012; W. Y. Li et al. 2014; Ma et al. 2016). LNA entered NTS bilaterally (FIG. 8 A, B). Using anatomical landmarks, including the midline of area postrema, we employed laser capture microdissection to extract bilateral NTS, which retained LNA signal throughout the sample preparation process (FIG. 8A-B?

Inhibition of microRNAs 135a and 376a In Vivo Via Intracerebroventricular Injection Attenuates Hypertension in Chronically Hypertensive Rats In order to evaluate the therapeutic window for intervention of the AM-376a+135a anti-miR treatment, we tested the LNA combination on SHR and WKY rats of 29 weeks old. SHR at this age exhibit chronic hypertension, increased weight compared to age-matched WKY controls, as well as increased sympathetic tone. Importantly, these rats are not close to the critical period of therapeutic efficacy previously identified (Baumann et al. 2007).

Figure 9A:
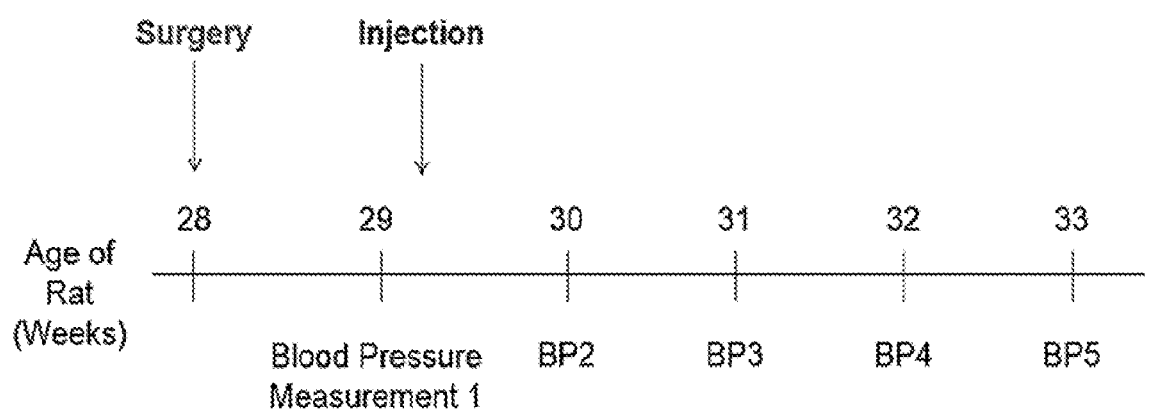
Figure 9B:
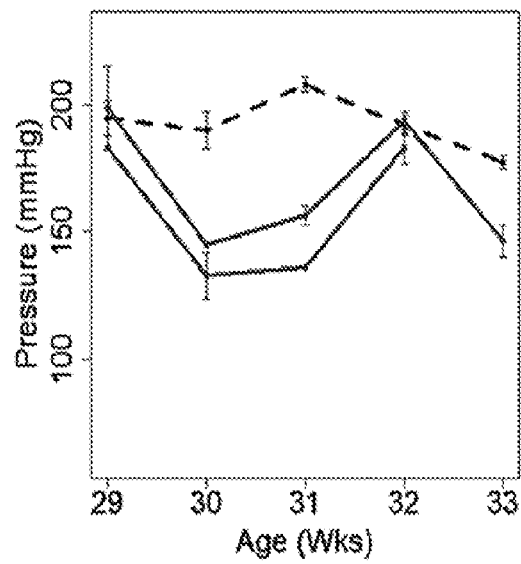
Figure 9C:
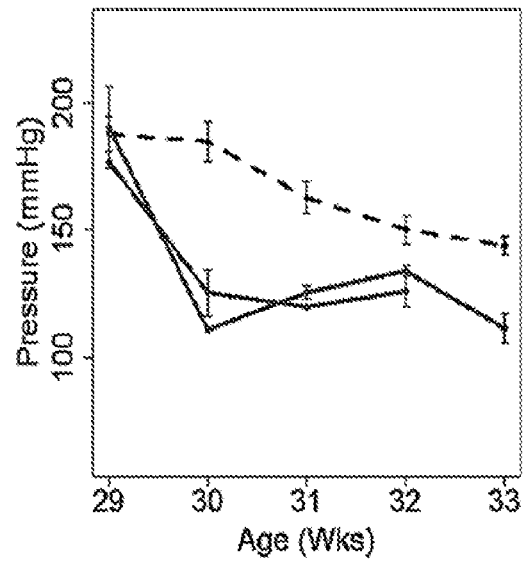
Figure 9D:
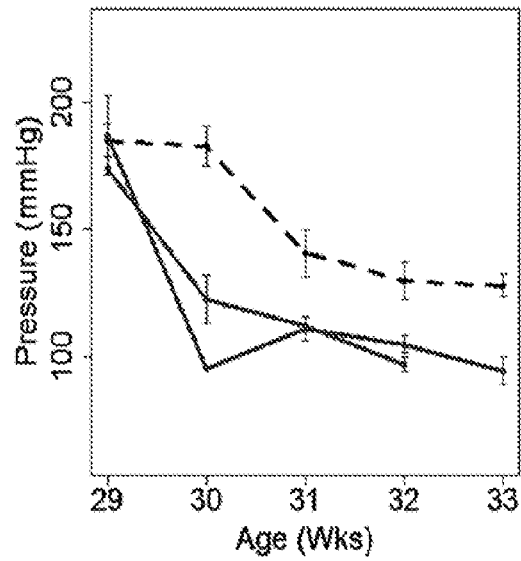
Figure 9E:
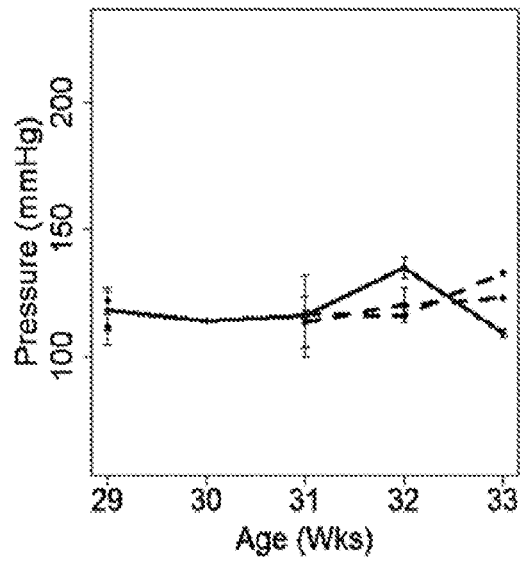
Figure 9F:
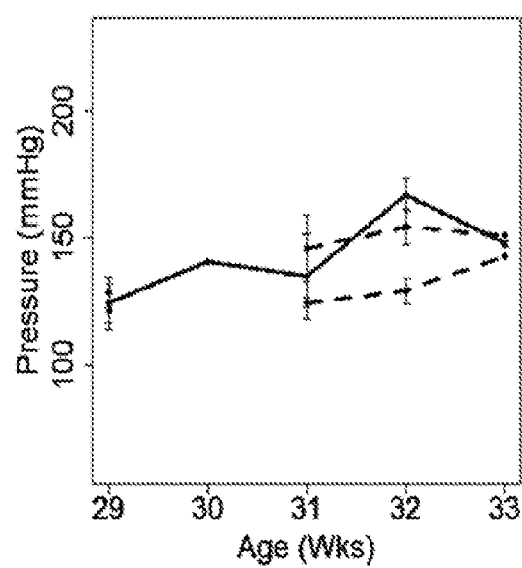
Figure 9G:
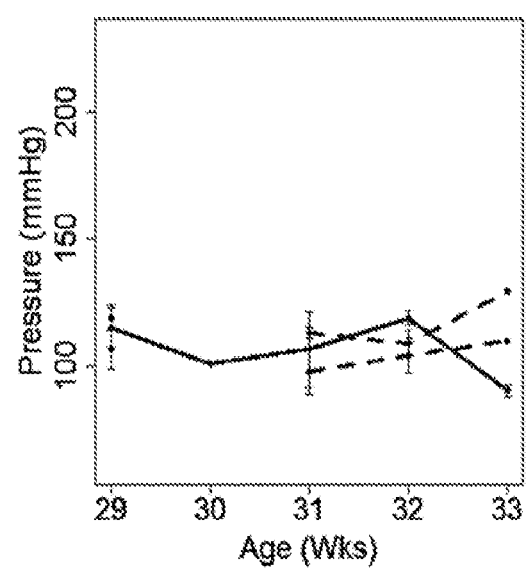

We tested the effects of inhibiting miR-135a and miR-376a in 30 week-old chronically hypertensive rats and their age-matched WKY controls (FIG. 9A). SHR animals that received a combination of anti-miRs exhibited decreased mean arterial pressure from 180 mmHg prior to injection to 125 mmHg one week post injection (n=2 animals (FIG. 9B), and corresponding changes were observed in the systolic and diastolic pressure as well (FIG. 9C-D). In contrast, the baseline MAP remained stable in the scramble oligo injected decreased slightly over time from a MAP of 188 pre-injection to a MAP of 150 3 weeks post-injection (n=1 scrambled). WKY animals that received either the combination of anti-miRs or scrambled showed stable MAP of about 115 throughout the duration of the experiment (n=1 treated, n=2 scrambled) (FIG. 9E-G).

Individual microRNA Inhibition Shows Contribution of microRNA-135a and microRNA-376a Independently to Blood Pressure Attenuation FIG. 10 details that after determining that an injection of the combined LNA cocktail composed of both anti-miR-135a and anti-miR-376a had a significant effect on blood pressure, we wanted to determine what the contribution was of each LNA and to get a sense if the effect was additive or synergistic. It was expected that either single anti-miRNA would have a smaller effect than the two combined and that this effect size would be more indicative of a synergistic rather than an additive mechanism. This is due primarily to the hypothesis that the anti-sense LNA oligos are disrupting miRNAs that are positioned to affect several genes in a network. When considering an effect that is most likely an emergent property of the network interactions, it is more likely the number of nodes perturbed will have a nonlinear relationship with the magnitude of the overall effect of that perturbation. SHR rats were injected with either anti-miR-135a or anti-miR-376a at 10 weeks of age. The MAP was reduced by 15±4.4 mmHg for the anti-miR-135a group and 16±7.9 mmHg for the anti-miR-376a group, p<0.05 for each using a nested ANOVA with Tukey HSD (FIG. 10). These decreases are more modest than the 62 mmHg reduction seen with the cocktail composed of the two LNAs over the same developmental time period (FIG. 8A). The cocktail comprised of the two LNAs had a synergistic effect that is greater than the sum of the reductions obtained by the individual LNA anti-miR.

For example, in FIG. 11C, we depict Log 2 median centered gene expression for SHR Scramble, SHR Cocktail, WKY Scramble, and WKY cocktail. This depicts gene expressions for bilateral NTS samples collected from all animals across each treatment group.

Figure 13A:
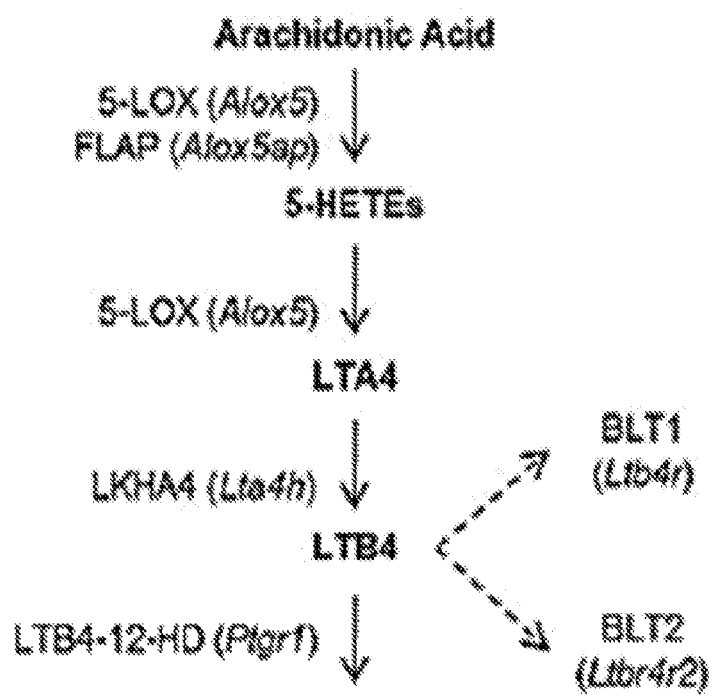
Figure 13B:
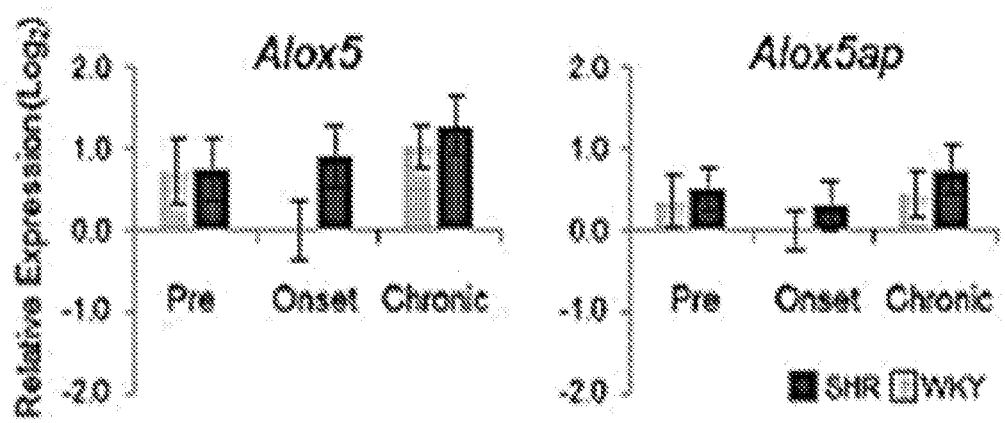
Figure 13C:
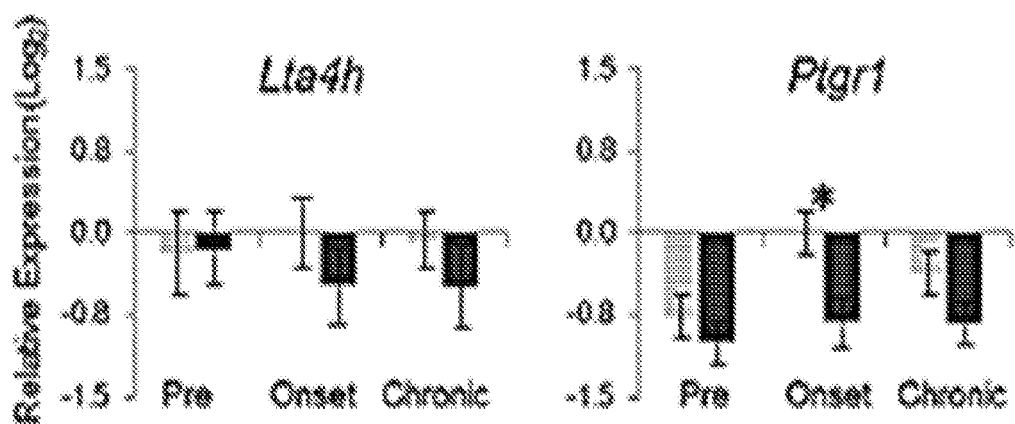
Figure 13D:
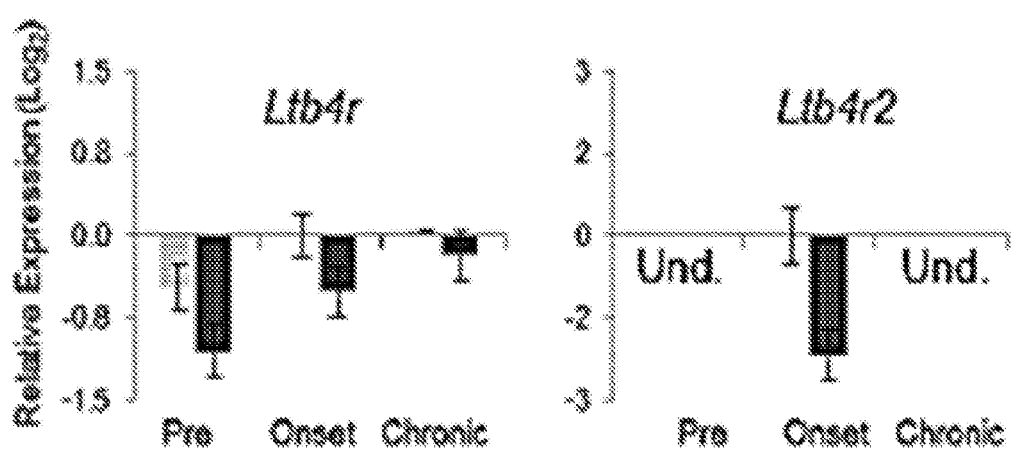

FIGS. 13A-D depict the dynamic changes in expression of LTB4 related genes over time in NTS. FIG. 13A) Summary of genes measured as they relate to Arachidonic Acid metabolism. Evaluation of six genes affecting LTB4 production (FIG. 13B, C-left panel), degradation (C-right panel) and signaling receptors (D) with reference to housekeeping gene Eif4e and WKY onset time point. * p<0.05, Strain Difference Significant, 2-factor ANOVA, Tukey HSD post-hoc p<0.05. Of note for strain significant difference is: AloxAP, p-value=0.076 and Lta4h, p-value=0.077. Und, Undetermined Expression, n=3-4 per gene. These data provides data for known Quantitative Trait Loci (QTL) of microRNAs showing differential expression dynamics during the development of hypertension. These results show that the microRNAs identified by our analysis are present in genetic loci that are relevant to blood pressure control, hypertension, cardiac health, and kidney function, providing additional literature support for prioritizing the microRNAs in our computational analysis for identifying hub microRNAs and their regulatory networks.

For example, the following table identifies certain Trait Loci of relevant microRNAs in the development of hypertension Microrna Inhibition Changes Microrna Regulatory Network in Shr in an Anti-hypertensive Manner

| microRNA | Rnor version | Chromosome | Start position | End position | Relevant QTL Associations |
|---|---|---|---|---|---|
| let-7i | 3.4 | 7 | 62755360 | 62755444 | BP QTL 182, BP QTL 181, Cardiac Mass QTL 27 |
| miR-130a | 3.4 | 3 | 67949594 | 67949681 | BP QTL 152 |
| miR-135a | 3.4 | 7 | 29077659 | 29077758 | Cardiac Mass QTL 6 |
| miR-137 | 3.4 | 2 | 214802296 | 214802397 | BP QTL 203, BP QTL 204, BP QTL 202 |
| miR-376a | 3.4 | 6 | 134404690 | 134404771 | BP QTL 211, BP QTL 213 |
| miR-423 | 3.4 | 10 | 67078723 | 67078816 | BP QTL 57, BP QTL 82, BP QTL 168, Cardiac Mass QTL 31 |
| miR-667 | 3.4 | 6 | 134400500 | 134400591 | BP QTL 211, BP QTL 213 |
| miR-702-3p | 3.4 | 12 | 20861548 | 20861658 | BP QTL 218, Renal Function QTL 21 |
| miR-92b | 3.4 | 2 | 181395426 | 181395508 | BP QTL Cluster 2, Prepulse QTL1, BP QTL 202, BP QTL101, Renal Function QTL9 |

Figure 12:
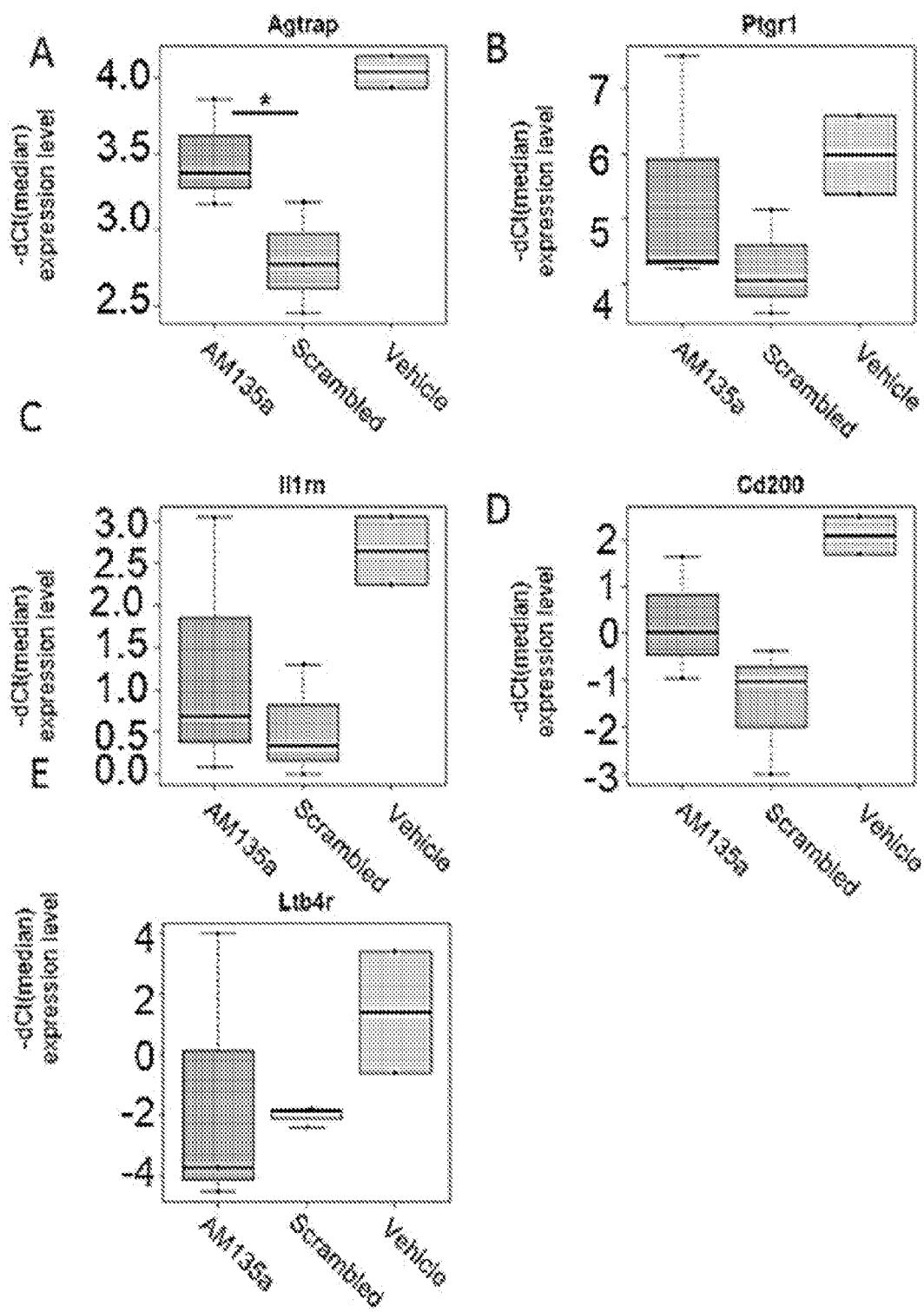

We measured 144 blood pressure related genes, most of which were predicted to be targets of this pair of microRNAs from animals injected with anti-microRNA therapy, and relevant WKYcontrols. Genes measured included Angiotensin II pathway genes, leukotriene b4-based inflammation, as well as different ion channels, neurotransmitters, and transporters (DeCicco et al. 2015; Hendy et al. 2016; Vadigepalli et al. 2012b). On a large scale, many transcripts changed expression levels. It is of note that gene expression levels were assayed at the end of the physiological time course, which was equivalent to 14 days after treatment. Transcripts we predicted to be targeted by these microRNAs displayed increased expression levels. Agtrap and RGS4, both negative regulators of Angiotensin II signaling, displayed increased expression levels in SHR injected animals compared to scrambled treated SHR animals (FIG. 11A, Top), but did not show similar changes in WKY treated animals (FIG. 11B, Top). Ptgr1, a negative regulator of Leukotriene B4 based inflammation, showed increased expression levels in SHR animals treated with combination anti-microRNA therapy compared to scrambled treated SHR animals (FIG. 11A, bottom), but did not show similar changes in WKY treated animals (FIG. 11B, bottom).

miR-135a Inhibition Increases Expression Levels of Predicted Targets in in Astrocytes Since many inflammatory pathways appeared to be affected, we wondered what the contribution of miR-135a, was to the transcript expression level changes we observed in vivo. We used CTX-TNA2 cells, a rat astrocytic cell line, to test whether inhibition of microRNA-135a alone affected hypertension-related transcript levels. We observed upon treatment with anti-miR-135a, predicted target Agtrap expression increased significantly (FIG. 12A). Anti-inflammatory transcripts and predicted targets of miR-135a Ptgr, Il1rn, CD200 also exhibited increases in expression levels (FIG. 12 B-D). Ltb4 receptor expression decreased upon treatment with anti-miR-135 (FIG. 12E).

Discussion

This is the first study that has examined the functional role of microRNAs and target gene expression in the regulation of blood pressure. We used the SHR animal model that mimics features of the development of human hypertension including increased sympathetic nerve activity, amplified Angiotensin II signaling and increased expression of Leukotriene B4 to test the efficacy of microRNA-135a and microRNA-376a as therapeutics (Duale et al. 2007b; Hendy et al. 2016; Iriuchijima n.d.; Masson et al. 2015; Sapru and Wang 1976; Udenfriend and Spector 1972; Waki et al. 2013a) Previously, microRNAs and target genes were evaluated in the SHR, and led to the microRNA-135a and microRNA-376a blood pressure regulatory network in the brainstem impacting Angiotensin II and Leukotriene B4 signaling (DeCicco et al. 2015). Since these microRNAs were held at higher expression levels in SHR during the 10-12 week time period, we considered this time period critical. We used a stereotaxic cannulization approach to test, in vivo, whether inhibition of these microRNAs in the brain stem during this critical hypertension onset period could renormalize blood pressure. We also tested whether this time period of intervention was critical by evaluating whether a single intervention during the onset period could prevent sustained hypertension.

Additionally, we evaluated the NTS gene regulatory network for both acute (48 hours post intervention) and chronic (two weeks post intervention) changes, and we found the network was rewired upon microRNA expression level manipulation. Furthermore, we evaluated the specific contribution of each, individual microRNA in blood pressure regulation, and we found astrocyte-enriched microRNA-135a to have an impact on the inflammatory component of the signaling responsible for the development of hypertension.

Based on our data, microRNA-376a and microRNA-135a are acting synergistically to rewire their regulatory network. Agtrap, a negative regulator of Angiotensin II signaling, was increased upon in vivo intervention in the SHR. This is the first evidence of either microRNA influencing the Angiotensin II pathway directly. Thus far, only one study has implicated miR-135a in Renin-Angiotensin-Aldosterone signaling, and it did so through implicating miR-135a as a potential regulator mineralcorticoid receptor gene (NR3C2), and linking that receptor to the Angiotensin II pathway (Sôber, Laan, and Annilo 2010). Aside from having predicted targets of Agtrap (DeCicco et al. 2015), neither microRNA has been associated functionally with altering Angiotensin signaling mediator expression levels. Increasing Agtrap has been shown to be protective in hypertension.

Agtrap overexpression has inhibited salt-sensitive hypertension in mice, suppresses angiotensin-dependent hypertension in aged mice, prevented salt-sensitive hypertension in rats upon a prepubertal sustained activation, and attenuated inflammatory vascular remodeling (Dejima et al. 2011; Oshita et al. 2006; Wakui et al. 2013). Conversely, lack of Agtrap has been shown to increase arterial blood pressure, and promote Angiotensin II-induced hypertrophy (N. Li et al. 2015; Oppermann et al. 2010). Therefore, increasing Agtrap should be protective in the development of hypertension. Inhibition of microRNA-135a and microRNA-376a does cause an increase in Agtrap expression, so our study does suggest this interaction to be directly related to reducing high blood pressure. Related to Angiotensin II signaling, and G-coupled protein receptor signaling in general is the increase in Regulatory of G-Protein 4, Rgs4, expression levels seen in SHR upon microRNA inhibition. Increasing RGS4 may also be modulating Angiotensin II signaling to attenuate blood pressure, although there is no direct evidence of this phenomenon thus far. RGS4 has been previously shown to prevent cardiac hypertrophy upon long-standing phenylephrine exposure, a substance often used to induce hypertension in animal models (Gu et al. 2009).

Inflammation-related pathways are also highly implicated in the development of hypertension, and likewise appear to be modulated upon inhibition of microRNA-135a and microRNA-376a. Leukotriene B4 is increased in NTS of SHR, and local as well as systemic inhibition of Leukotriene B4 receptor exhibiting a blood pressure reduction (Hendy et al. 2016; Waki et al. 2013a). Furthermore, Ptgr1, an enzyme responsible for the degradation of Leukotriene B4 is elevated during the critical hypertension onset period in NTS of SHR, and is the only enzyme significantly differentially expressed in this pathway during the onset time period (DeCicco et al. 2015; Hendy et al. 2016). Ptgr1 is a predicted target of microRNA-135a, and has not been shown to be a direct target, despite its expression level increase upon miR-135a inhibition (DeCicco et al. 2015). Ptgr1 degrades LTB4, and decreasing LTB4 signaling in NTS of SHR attenuates hypertension. Therefore, inhibition of microRNA-135a causing an increase in Ptgr1 expression and concomitantly decreasing blood pressure provides evidence for both the role of Ptgr1 and microRNA-135a in central blood pressure regulation.

Each microRNA appears to be playing a unique role in regulating blood pressure. It is interesting to speculate on the synergy of using both microRNAs together than to use individual microRNAs. It appears by using the pair of microRNAs we can observe a sustained anti-hypertensive effect for longer than using either one alone. This may be in part to the pair being capable of targeting more pro-hypertensive signaling pathways than each individual microRNA alone. Additionally, these microRNAs may be acting in different cell types in the CNS (Jovičić et al. 2013) increasing their efficacy.

Interestingly, microRNA-135a has previously been shown to be enriched in astrocytes, so we wondered what the microRNA-mediated contribution of astrocytes to the tissue-level changes we observed was apparent suggesting an astrocyte-mediated inflammatory effect (Jovičić et al. 2013). We found upon microRNA inhibition in vitro that Agtrap, Ptgr1, Il1rn, a negative regulator of Il-1 signaling, and CD200, an anti-inflammatory molecule all exhibited increased expression levels, suggesting regulation by microRNA-135a. Furthermore, the Leukotriene B4 receptor was decreased upon microRNA-135a inhibition. Increasing Ptgr1 expression level and decreasing Ltb4r expression level could act synergistically to contribute to the decrease in blood pressure we observed in vivo.

Our study also provides evidence for an acute therapeutic intervention providing sustained symptom relief. Previously Baumann et al., discovered that in SHR, one could block the Ang II receptor from 4-8 weeks of age, and prevent hypertension from developing for up to 46 weeks of age in these animals (Baumann et al. 2007). While our study was not conducted for that magnitude of time, we did find evidence that a one-day treatment with LNA prevented hypertension for up to two weeks when given at the age of 9 weeks. An extension of our study could include sustained drug delivery for a four-week period similar to the critical period Baumann discovered, to further evaluate if the therapy could prevent hypertension chronically. Interestingly, our lab has evidence to believe that acute inhibition of these microRNAs in aged rats (28 weeks), keeps blood pressure reduced for up to a month (FIG. 9?).

In conclusion, the present study provides novel evidence of a causative mechanism of microRNA-135a and microRNA-376a in essential hypertension in the Spontaneously Hypertensive Rat. Of critical importance, the finding that the inhibition of microRNA-135a and microRNA-376a with LNA through intracerebroventricular injection significantly reduced blood pressure, and maintained the reduction in blood pressure for up to two weeks post-injection. This effect is mediated partially through increasing the expression of Agtrap, and partially mediated through increasing the expression levels of Ptgr1, amongst other negative regulators of inflammation. This study provides proof of concept that manipulation of non-coding RNA in the brain is able to affect physiology. Although, we must carefully and thoroughly examine the safety and efficacy of this therapeutic, and many more investigations must be performed before we are able to extrapolate to humans, the present study suggests novel insights for the development of therapeutic strategies that may be able to extend to patient populations currently not well controlled on their hypertensive medications.

Where micro-RNA 135a and 376a are being implicated, single therapeutic treatment can be effective. Indeed, as described throughout these embodiments, a first method may include a single therapeutic treatment. This anti-miR towards 135a or 376a may be sufficient to re-wire or change the manner in which the body is being regulated. Accordingly, a single therapeutic may be sufficient for treatment and control of hypertension for about four weeks. This allows for a unique administration protocol where a single dose, on a regular schedule of every, about 28 days can control hypertension in the body. By determining hypertension levels between administrations, evaluation of whether a single anti-miR is sufficient, or a combined, synergistic therapy is needed, can be easily evaluated.

However, based on our data, a combined therapeutic has synergistic implications, with nearly four times the reduction in MAP in the studies and data described herein. Accordingly, use of the single anti-miR 135a or 376a may be sufficient, or in some cases, may be insufficient to reduce hypertension to sufficient and safe levels. Accordingly, the combined therapeutic may be necessary to re-wire or modify the regulation of the body sufficiently to reduce hypertension to safe levels.

Scalability of MicroRNA Regulatory Networks

How accurate we can extrapolate smaller subunits of data from a larger average measurements remains to be seen in standard biological studies, ie. extrapolating tissue—level transcript data from single cell data or vice versa. However, in this study, we measure microRNA expression levels for two key microRNAs relevant in neurogenic hypertension, and over 100 transcripts in single cells pooled into groups of ten. Both microRNA and putative target expression levels were assayed from one sample using a sequential reverse transcription sequence followed by a single pre-amplification step, then assay measurement. We asked if correlative relationships between microRNA expression levels and putative target expression levels in tissue of a small, localized anatomical nucleus in the brainstem could be localized to single cells taken from that region. Additionally, we asked how these correlative relationships act in vitro. In this study, each microRNA was previously shown to be enriched in a certain cell-type in the brain, and we used that information to partition the transcripts measured at the tissue level to characterize each cell type in order to best represent the biology occurring in the system. Our results reveal that correlative networks between microRNAs and predicted targets are robust and scalable, and may serve as valid support of mechanistic interaction between these two RNA species.

MicroRNA-mediated regulatory networks have recently emerged as having playing a major role in disease (Bhajun et al. 2015; DeCicco et al. 2015; Satoh 2012; H. Wang et al. 2016). microRNAs are classically known to down-regulate their mRNA targets through seed region recognition and base-pairing (Bartel 2009; Enright et al. 2003; Farh et al. 2005). But, we now understand that microRNAs can impact biological systems through several regulatory methods. microRNAs have been shown to stabilize transcripts, to act as decoys for transcription factors, to reduce intrinsic noise in biological systems (Clark et al. 2014; C. Cui et al. 2014; Schmiedel et al. 2015; Wylie et al. 2014; Xia et al. 2012). Targeting of lowly expressed genes and combinatorial microRNA control of multiple gene targets has been shown to improve signal to noise ratios in biological signaling cascades (Enright et al. 2003; Farh et al. 2005; Krek et al. 2005; Schmiedel et al. 2015).

Single cell biology has emerged as critical in understanding biological functions (Bartfai, Buckley, and Eberwine 2012; Dueck, Eberwine, and Kim 2016; Eberwine and Bartfai 2011; Park, Brureau, et al. 2014; Spaethling et al. 2014; Tang et al. 2010; Tay 2015). Single cells retain significant amounts of gene expression variability, and cells of the same type have been able to be classified into different sub-phenotypes (Makadia, Schwaber, and Vadigepalli 2015; Park, Brureau, et al. 2014; Park, Ogunnaike, et al. 2014). Since microRNAs have now been shown to have several types of regulatory impact on biological systems, it is of interest to examine the robustness of these predicted interactions across biological scales.

With the integration of high-throughput data collection approaches into mainstream biology, numerous gene network analyses have been performed. A multitude of algorithms have been developed to extract signaling networks from large data sets (Cho, Kim, and Przytycka 2012; Czerwinska et al. 2015; Gao et al. 2014; Opgen-Rhein and Strimmer 2007; Saez-Rodriguez et al. 2009; Vadigepalli et al. 2012b). However, there is a lack of data validating the robustness of networks of microRNA-mRNA putative pairs across biological scales. Furthermore, in our understanding, there has been no biological characterization of correlative networks of predicted microRNA-transcript targets across scales.

In this work, we evaluate a correlational microRNA-mRNA putative relationship interaction derived from a network composed from bioinformatics predictions and expression level relationships at the tissue scale. Our data is taken from the spontaneously hypertensive rat (SHR), a model of hypertension which recapitulates may of the features of human essential hypertension and its control strain, the Wistar Kyoto Rat (WKY) (Doggrell and Brown 1998; Veerasingham and Raizada 2003b). Previously, in a global microRNA study, we characterized a microRNA regulatory network that appeared to be underlying the development of hypertension in the rat model (DeCicco et al. 2015). We measured expression data of microRNAs and predicted mRNA targets from two key brainstem nuclei responsible for blood pressure regulation, and we constructed a microRNA-regulatory network based on correlation between the two data sets. We found interesting biology, but it was also documented that the microRNAs we discovered were enriched in different cell types in the brain.

The aim of this study was to determine whether the microRNA regulatory networks from predicted target transcript pairs, we observed at the tissue level would be maintained at the single cell level. If the networks are maintained, at both the single cell level in vivo and the tissue level in vivo, we additionally would evaluate whether in vitro models could still represent the correlative relationships we discovered in vivo. Characterizing the robustness of correlative network relationship across scales will bolster support for utilizing network-based approaches and bioinformatics predictions to uncover biological significance.

Materials and Methods

Animal Model: Male, Wistar Kyoto (WKY/NHsd) rats and spontaneous hypertensive rats SHR/NHsd) obtained from Harlan Laboratories were housed 1 per cage in the Thomas Jefferson animal facility to avoid animal to animal stress from dominance that could affect blood pressure. Facilities were maintained at constant temperature and humidity with 12/12 hour light cycles (lights on at Zeitgeber time [ZT] 0). All protocols were approved by the TJU Institutional Animal Care and Use Committee.

Laser Capture Microdissection (LCM): Laser capture microdissection was used to obtain precise regional samples from NTS. To reserve RNA integrity, dehydration was performed within 20 minutes. Slides were fixed in cold Acetone with 1% Hydrogen Peroxide (Sigma-Aldrich) for 1 minute, then permeabilized and blocked with 2% Bovine Serum Albumin solution in Phosphate Buffered Saline for 30 seconds. Slides were washed in PBS and dehydrated in graduated ethanol concentrations followed by two immersions in Xylene for 1 minute and 5 minutes, respectively. The LCM process was performed using Arcturus XT LCM. The NTS was localized using anatomical landmarks, and NeuN, a neuronal marker, and GFAP, an astrocyte marker to lift each individual cell type (Park, Brureau, et al. 2014). We have previously shown the enrichment of correct cell populations captured and more detailed methodology (Park, Brurea et al., 2014) Ten of each cell type were pooled per each cap, and cells were lysed direction on the cap, and cooled on ice before −80 degree Celsius storage.

Cell culture of CTX-TNA2 astrocytes and transfection: Cells were obtained directly from ATCC, and passages 6-10 were used for experiments. Per ATCC protocol, cells were maintained in DMEM supplemented with 10% (V/V) FBS, penicillin and streptomycin. The cultures were exposed to Leukotriene B4 (Sigma Aldrich) at three concentrations: 1 nM, 10 nM and 50 nM. Cells were exposed for 48 hours after plating. Cells were evaluated morphologically to assure phenotype maintenance Cell Culture RNA Preparation: At relevant time point treatment, cells were harvested through direct application of TriZOL using the Direct-zol RNA MiniPrep kit (Zymo Research, Orange, Calif.). This kit captures all RNA greater than 18 nucleotides in length, and stored at −80° C. Concentration and integrity were assessed with an ND-1000 (NanoDrop, Philadelphia, Pa.). RNA was used for microRNA and mRNA simultaneous qPCR application.

microRNA and mRNA simultaneous high-throughput quantitative PCR sample preparation: microRNA expression levels and transcript expression levels were measured using a sequential reverse transcription reaction from one LCM-obtained sample. Samples of bilateral NTS obtained from LCM, and lysed on cap were directed into universal reverse transcription reaction to reverse transcribe all mRNA (Vilo, Life Technologies). Following a universal reverse transcription, the sample underwent reverse transcription for specific microRNAs (miR-135a and miR-376a) using the Taqman detection system to increase specificity of future quantification. Due to limited RNA amount, one universal preamplification step was performed using primers for genes of interest and microRNAs of interest using TaqMan® PreAmp Master Mix per the manufacturer's protocol (Applied Biosystems, Foster City, Calif.). Finally, genomic DNA was digested and genes and microRNAs were measured using high-throughput qPCR or standard qPCR.

High-throughput qPCR: For the transcript measurement and quantification for the previously prepared sample, qPCR reactions were performed using 96.96 BioMark™ Dynamic Arrays (Fluidigm®, South San Francisco, Calif.) enabling quantitative measurement of multiple mRNAs and samples under identical reaction conditions (Spurgeon et al. 2008). Each run consisted of 40 amplification cycles (15s at 95° C., 5s at 70° C., 60s at 60° C.). CT values were calculated by the Real-Time PCR Analysis Software (Fluidigm). Intron-spanning PCR primers for every assay were designed and tested for proper amplification before use on a BioMArk array. microRNAs were detected using a standard ABI 7000 qPCR platform using Taqman standard chemistry.

Data Normalization and Analysis: We followed the methods we have previously utilized for high-throughput transcript level analysis (DeCicco et al. 2015). In brief, assays and samples failed by software due to technical noise were discounted for downstream analysis, and data was normalized by median gene expression levels across 96 genes in the case of the 96.96 dynamic array.

Correlation of Samples: Normalized data from single cells was correlated across samples based on Pearson correlation between microRNA expression levels and mRNA expression levels. In vitro, from normalized data, correlations were performed across samples, similarly. Furthermore, normalized tissue level data used was previously made available in DeCicco et al., 2015, and was correlated across SHR and WKY animals across time using Pearson Correlation to obtain correlation values used to compare to the data obtained in the current study.

Figure 7:
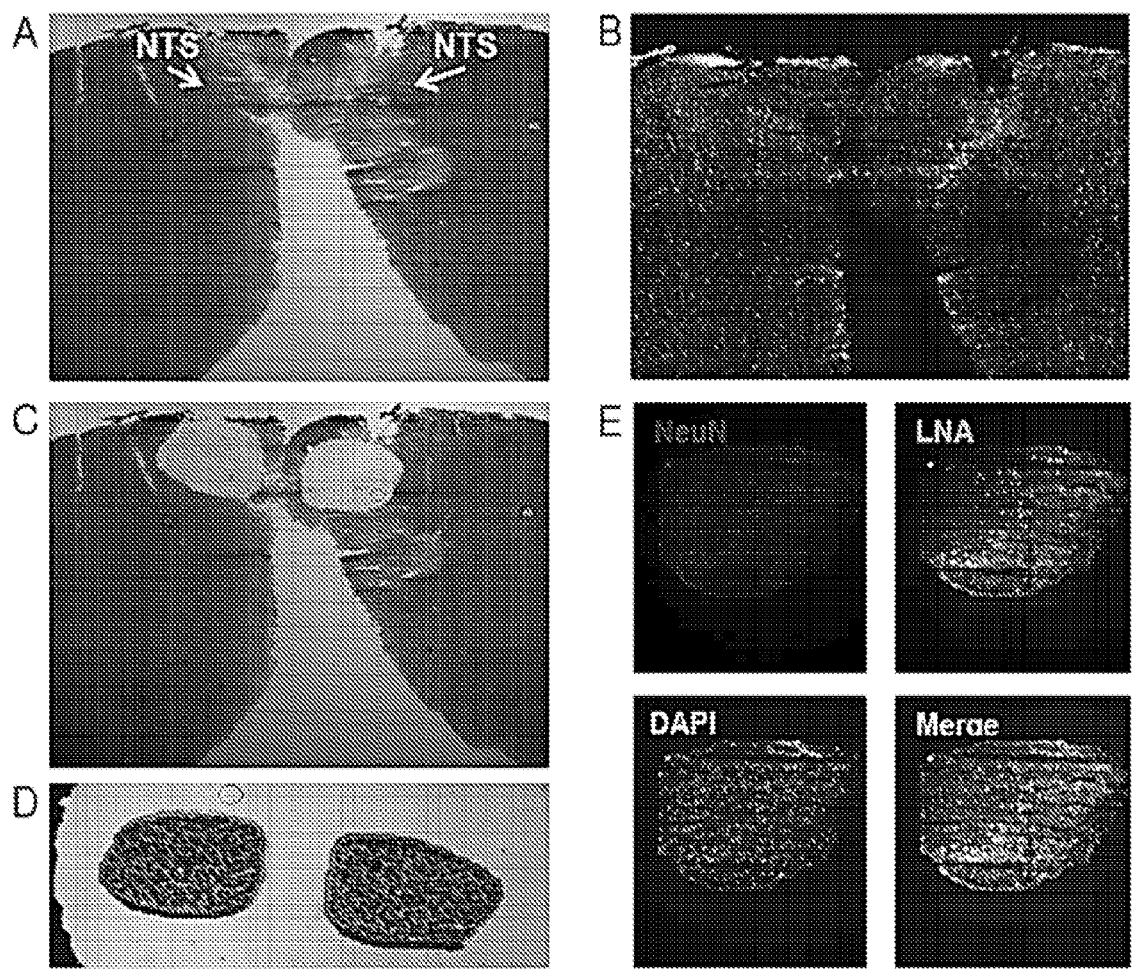

Results microRNA-135a Exhibits Anti-Correlation Relationship Across a Subset of Predicted Targets Since microRNA-135a was previously shown to be enriched in astrocytes, we collected pools of 10 astrocytes from the nucleus of the solitary tract at the hypertension onset period (Jovičić et al. 2013; Park, Brureau, et al. 2014). This time period corresponded to the onset period of time in hypertension characterized in DeCicco et al., 2015. We extensively collected cells labeled with Glial fibrillary acidic protein (GFAP), a reliable astrocyte marker. From these samples we assayed 96 predicted targets previously measured at the tissue level (DeCicco et al, 2015). Confirming previous results, microRNA expression level across samples is higher in SHR compared to WKY samples in pooled astrocytes (FIG. 7A, top). Broadly, the predicted targets measured could be grouped three ways: 1) targets with expression levels anti-correlated across samples in NTS (FIG. 7) 2) targets with expression levels that could not be correlated or anti-correlated across samples in NTS (FIG. 7), and 3) targets with expression levels correlated in NTS with that of the microRNA (FIG. 7). From 96 genes assayed, 73 were used in downstream analysis due to quality control and normalization procedures. Of those 73 genes, we found that 18 were anti-correlated with correlation values less than −0.3 (FIG. 7), we found 7 to be positively correlated (FIG. 7), and we found 48 to have no correlative relationship with the expression level of microRNA-135a (FIG. 7).

Comparison of Tissue, Single Astrocytes and Cultured Astrocytes Show Several Network Similarities In order to address the scalability question, we used data previously published to assess tissue correlation values between microRNA-135a and predicted targets. We also assayed an in vitro system of cultured astrocytes from rats (CTX-TNA2 cells, ATCC) in order to keep species homology. We treated the cells with Leukotriene B4 to mimic the hypertensive environment found in vivo in SHR (Hendy et al. 2016; Waki et al. 2013a). We compared the relationships between microRNA: mRNA pair in each of three sample types: single astrocytes, time-series tissue data and in vitro data, and if the correlation value between the microRNA: mRNA pair within a sample type was above 0.3, the microRNA: mRNA pair was considered positively correlated, if it was less than −0.3 the pair was considered negatively correlated. We analyzed a list of 44 genes that were measured using the same primers across all three sample types, and we found that there were many more consistent anti-correlative relationships than positively correlated relationships in SHR across sample types.

microRNA-376a Exhibits Anti-Correlation Relationship Between Expression Levels Across Pools of Ten Neurons We performed a similar analysis in neurons. Supporting previous results, we confirmed at the single neuron level that microRNA-376a is expressed at generally higher levels in neurons in SHR compared to neurons in WKY (FIGS. 8A, and 8B, top). Of 96 measured targets, 90 were used in downstream analysis due to normalization criteria. Of the 90 putative targets assayed, 20 displayed a negative correlation, with correlation value less than −0.3 with microRNA-376a (FIG. 8), 53 targets displayed no correlation (FIG. 8), and 17 targets displayed a positive correlation with microRNA-376a expression (FIG. 15-III).

Therefore, use of a therapeutic for anti-miR 135a or 376a is sufficient to impact the cells and body at a neuronal level. Therefore, we expect that treatment may be sufficient for shorter duration treatments, where the body may be modified or have the system re-configured so as to reduce hypertension.

Discussion:

To our knowledge this is the first study that has examined the putative microRNA-mRNA correlation-based mechanisms in a high-throughput manner across biological scales in a relevant disease model. We used the SHR animal model that recapitulates several features of human essential hypertension in conjunction with pools of laser-capture dissected single cells and model cell culture environment to test whether putative microRNA:mRNA correlations would show similar features across these three different biological scales.

We obtained pools of ten single neurons or ten single astrocytes from the nucleus of the solitary tract, and we measured microRNA expression levels and mRNA expression levels from one pool. We correlated the values and compared those values across scales with data that has previously been published at the tissue level (DeCicco et al.) and with culture data of astrocytes that we obtained.

While there were many genes that did not show similar correlations or anti-correlations with their respective microRNA across scales, several genes did. In both the astrocyte and neuron case, there was a broader concordance across the anti-correlated relationships between a microRNA and target gene than the microRNA and a positively correlated target gene suggesting increased substantiation of the canonical microRNA regulatory motif. microRNAs have typically thought to bind to their predicted mRNA target to down-regulate them. This relationship would exhibit itself as an anti-correlation in expression level between the microRNA and mRNA, which is shown here to be more robust across biological scales. While the original correlational relationships and network from the tissue scale could not precisely be scaled down to the single cell level, aspects of the networks and relationships were maintained. This agrees with the wide body of literature suggesting single cells capture features of biological variability unable to be seen at the tissue level (Dueck, Eberwine, and Kim 2016; J. K. Kim and Marioni 2013; Park, Brureau, et al. 2014).

Two genes were strongly anti-correlated across the three scales in astrocytes: Coq7 and Tnfrsf1a. Coq7 or Coenzyme Q7 an enzyme in ubiquinone biosynthesis has been associated with hypertension in SHR in early left ventricular hypertrophy in one study using a proteomic approach (Gallego-Delgado et al. 2006). Our finding and approach of using a microRNA-centered correlation analysis, confirms the significance of this gene; however, it adds to the previous literature two new findings in the context of essential hypertension: 1) Coq7 is associated with microRNA-135a, and 2) Coq7 is associated with astrocytes both in vivo and in vitro. Using our approach we have identified a new target with increased evidence of its implication in essential hypertension. This putative target could also be regulated by miR-135a, which has previously been shown to have increased expression levels in the development of hypertension (DeCicco et al., 2015). Furthermore, the significance of this transcript may not have been pursued in a typical hypothesis-driven approach, as it is not involved directly in the well-characterized pathways associated with essential hypertension, and has only been identified with an -omic style approach (Gallego-Delgado et al. 2006).

The other transcript, Tnfrsf1a, when queried in PubMed, shows 8 studies in the context of hypertension. Only one of those studies actually implicates Tnfrsf1a in the disease itself, but indirectly. The implication of Tnfrsf1a, potentially, in hypertension can be linked to a study of Angiotensin II induced cardiac fibrosis. The study used a mouse knock-out model of the Tumor Necrosis Factor Receptor 1 to attenuate collagen deposition, and prevent cardiac remodeling, cardiac hypertension and hypertension in a chronic Angiotensin II exposed mouse model (Duerrschmid et al. 2013). This literature confirmation of our finding suggests Tnfrsf1a warrants future study, and could be a new target in the context of essential hypertension. However, our study has complemented the previous study and added to it the implication of microRNA-135a and astrocytes in this biological system.

In the neuron case, we discovered several putative targets implicated in essential hypertension to be potentially regulated by microRNA-376a. There were five targets that showed similar anti-correlation across single neuron pools and tissue including: Jund, Nr3c1, Panx2, Rgs3, and Tnfrs1b. All of these genes have been associated with hypertension except for Panx2. Panx2, Pannexin 2, is a protein that is expressed highly in the CNS, and comprises the structural part of gap junctions (Penuela, Gehi, and Laird 2013; Swayne and Bennett 2016). This protein has previously been explored in the ear, retina and in glioma cells (Dvoriantchikova et al. 2006; Lai, Bechberger, and Naus 2009; H.-B. Zhao 2016). While Panx2 has not directly been implicated in hypertension like the other transcripts discovered through our cross-scale analysis, one of its isoforms, Panx1, has been previously associated with vasoconstriction through phenylephrine induced arterial constriction (Billaud et al. 2011). Our finding suggests a role for Panx2 in neurons mediated through microRNA-376a in essential hypertension that should be further investigated.

The broader implications of our study illustrate the principle that using correlational expression relationships between transcripts and non-coding RNA can show robust results in different models of a disease. Here we have examined single cells, tissue and cultured cells. However, with the increase in innovation for modeling biological systems through different means to approach disease biology, it is also important to highlight that simply because one does not agree with the other does not make one of the models wrong. In the case of single cells, we can use computational approaches to parse out the contribution of the cell type to the tissue as a whole. We can learn which pathways are enriched in which cell-types, and how those cell types interact together to make the system function as whole.

However, we should use caution in selecting in vitro platforms, as conclusions discovered in vitro, as illustrated here, may not be the same in vivo at either the single cell level or the tissue level. Our data suggests that the relevant comparison to make, when using cell lines, is to compare the data to single cells or cell pools of the same type from the disease model one is trying to examine instead of comparing cell-line data to tissue. Our data illustrates that correlational relationships between a microRNA enriched in astrocytes and its predicted targets is more similarly correlated between the culture data and the single-cell scale data than the culture data and the tissue data.

Additional experiments using other cell types, species, and disease models are required to expand our evidence of robust correlational microRNA networks being scalable. Our results identify and qualify correlational predicted relationships between microRNAs and mRNAs across biological scales within a disease model to be robust and noteworthy in terms of biological discovery. Furthermore, our results highlighted two transcripts as examples of non-obvious candidate genes for the treatment of essential hypertension. Understanding the robustness of network biology and correlational relationships in relevant disease models yields new approaches and increased throughput for characterizing and intervening in polygenic, multi-organ diseases like essential hypertension.

DISCUSSION

The major objective of this body of work was two-fold with respect to understanding essential hypertension: 1) to characterize the microRNA environment in the brainstem, a center blood pressure control region and 2) to evaluate potential microRNA therapeutic targets within that framework to allow for therapeutic treatments in human patients.

In order to address the former, a global microRNA study was performed in a well-characterized rat model of essential hypertension to evaluate the system for any hub microRNAs linking to known signaling pathways implicated in hypertension that we might pursue to control the development of hypertension. We also localized these microRNAs to relevant cell types. To address the latter, from the 23 differentially expressed microRNAs were found to be implicated in the brainstem during the development of hypertension, we focused our efforts on manipulating a pair of these microRNAs in vivo, as there was sufficient evidence in bioinformatics prediction and the literature, as well as our measured transcript data, to support this pair of microRNAs' role in the molecular etiology of hypertension. Based on our studies, we exhibited the first demonstration of central manipulation of microRNAs for the regulation of blood pressure.

Importance of Global Studies:

As depicted in FIGS. 4A-4D, our study uses a global assay to characterize hundreds of well-annotated microRNAs in two key brain regions in the development of hypertension. Using this approach enables us to gain invaluable insight into autonomic control of hypertension as a system. Before our study, there had been no characterization of microRNAs in the NTS and RVLM in the context of essential hypertension. Analyzing 419 microRNAs, and concluding seven as significant in the NTS and 16 as significant in RVLM throughout the development of hypertension allowed us to focus on microRNAs that have a higher chance of being relevant to the physiology.

From our global study, we were able to implement high-throughput bioinformatics algorithms such as RNA22 and miRWALK (database searching 12 different bioinformatics algorithms) to predict mRNA targets for the significant microRNAs (Dweep et al. 2011b; Miranda et al. 2006). After overlapping the predicted target list with a list of genes derived from literature which focused on AT1R signaling through PKC, CaMKII, MAPK and PI3K pathways, immediate early genes (e.g., Fos, Egr1, Egr2, Egr3, Jun, Junb), and ion channels and transporters (e.g., for NE, glutamate, Na+/Ca2+, Ca2+), guided by our previous studies (Khan et al. 2008; Park, Brureau, et al. 2014; Vadigepalli et al. 2012a), as well as genes relevant to inflammatory pathways shown to affect blood pressure regulation, including interleukins, chemokines, and leukotrienes (Hendy et al. 2016; Waki et al. 2013a; Winklewski et al. 2015; Zubcevic et al. 2011). Several of these pathways are enriched in astrocytes (e.g., inflammatory processes) vs. neurons (e.g., ion channels), whereas the transcriptional regulators and signaling pathways may be common to both cell types. We could narrow in on a pair of microRNAs that appeared to impact both the Angiotensin II signaling pathway the Leukotriene B4 biosynthesis pathway in order to find a therapeutic target. Without the utility of high-throughput data sets and large-scale bioinformatic predictions, our evidence may have biased us toward a microRNA with less impact than the microRNAs we decided to pursue in our investigation.

Global studies and systems-based approaches provide a context for the question being asked, and for disease and especially for biological signaling pathways. Chasing discoveries that may lead to novel knowledge acquisition needs to be kept in the perspective of the biological system. (Barabasi, Gulbahce, and Loscalzo 2011; Dhurjati and Mahadevan 2008). Global studies provide a relatively unbiased way to evaluate the sensitivity of the system to each component, or microRNA in our case, in order to find key hubs that can be manipulated to change or rest the system. Additionally, to aid in further discovery, a benefit of global data sets is that they typically should be made freely accessible to the larger scientific community. Sharing large datasets enables innovation to take place on a larger scale with fewer resources, as other groups can query the data for questions that interest them, which is a positive consequence of performing global studies (Lapatas et al. 2015; "Sharing Data" 2009; Vickers et al. 2006).

Gene Hubs, Networks and Functional Relevance:

Network Based Approaches: Many approaches have been developed in order to derive gene regulatory networks from gene expression data (Böck et al. 2012; Casci 2006; Margolin et al. 2006; M. K. Morris, Melas, and Saez-Rodriguez 2013). Hub genes are central genes, or microRNAs in this case, within a network which have a higher degree of connectivity than other genes within the same network and have a functional impact on physiological outcomes (Casci 2006; Gaiteri et al. 2014; Lehner et al. 2006). Gene networks and subsets within those networks (i.e. modules) have been shown to be more robust across higher order organisms such as rodents; hub genes within those modules have been shown to be crucial in elucidating the underlying biology driving a phenotype (Albert, Jeong, & Barabasi, 2000; Albert & Barabási, 2002; Böck et al., 2012; Gaiteri et al., 2014; Langfelder, Mischel, & Horvath, 2013). Recently microRNAs have been shown to be key network regulators in breast cancer by serving as hubs (Bhajun et al. 2015; Satoh 2012).

In our work, we used a network analysis of global and high-through-put data linked through bioinformatics and expression level correlation to build evidence for a pair of microRNAs that underlie the development of hypertension. Classically, hypertension has been treated with barrage of drugs intended to subdue the Angiotensin II signaling pathway, such as Losartan, and Angiotensin II Receptor Type I partial antagonist or drugs like Lotensin and Monopril which block the enzyme responsible for converting Angiotensin I to Angiotensin II called Angiotensin I Converting Enzyme (ACE) (Y. S. Chan and Wong; von Lueder and Krum 2013; von Lueder et al. 2013; Paul, Poyan Mehr, and Kreutz 2006). Recently, systemic intervention with Leukotriene B4 receptor antagonists have shown promise in the treatment of hypertension (Hendy et al. 2016; Waki et al. 2010a, 2013a). Using a network approach, we discovered microRNAs with the potential to modulate both pathways at the same time.

Significance of Biological Feedback in Gene Regulation: Furthermore, because the network we developed was based on correlational relationships between microRNA expression levels and mRNA expression levels, we were able to determine potential for feedback in this loop. While we have not explicitly examined and tested for feedback of signaling pathways in our data; however, we observed an interesting motif that could warrant future investigation. Our data suggests a double-negative disinhibition of the Ang II and LTB4 signaling pathways (FIGS. 6A and 6B).

In the context of feedback, there are a few common feedbacks in biology: positive feedback; where increasing one product directly increases another product; negative feedback, where increasing one product decreases a related product; and mixed feedback looks which use both positive and negative feedback and can be coherent incoherent. Feedback loops in general have several roles from creating molecular switch-like behavior, to increasing robustness in signaling, to managing noise (Cai, Zhou, and Liu 2013; Mukherji et al. 2011; Schmiedel et al. 2015). Double-negative feedback loops for microRNAs have been characterized in neuronal cell-fate processes as exhibiting switch-like behavior (Johnston et al. 2005). However double-negative disinhibition has been characterized several times before in other systems. In a MAPK cascade in E. coli, the network feedback has been shown to make the system more responsive to subtle changes in expression levels of one or both of the gene products, converting graded inputs into essentially a switch (Ferrell 2002; FERRELLJR 1996). Double-negative disinhibition feedbacks can lead to the signaling network exhibiting bistability, which has been shown to be a mechanism by which cells can adapt to constantly changing molecular landscape (Ferrell 2002; Kuwahara and Soyer 2012). Additionally, double negative feed forward inhibition has also increased robustness of the biological system (Ebert and Sharp 2012; Johnston et al. 2005). The double-negative feedback loops emergent in the hypertension microRNA regulatory network may be in place as a sensitive molecular switch that is perturbed during the development of the disease (Dvinge et al. 2013; Mukherji et al. 2011).

Shifting Dynamic Molecular Balances: Since the microRNAs characterized in the development of hypertension appear to be acting in a feed-forward double negative disinhibition pathway, it is crucial to evaluate how the signaling networks shift upon intervention with the LNAs. Upon LNA intervention, we observed large, significant decreases in blood pressure, but we also observed transcript expression level differences between treatment groups for up to two weeks post injections (FIG. 8A).

Changing the functional expression utility of the microRNAs with LNAs had long-lasting effects of the predicted targets. Typically, when assaying RNA changes post an intervention, time courses of shorter magnitudes are used to capture the peak of changes in transcription. While we did not necessarily expect to see long-standing molecular changes for up to two weeks post ICV injection, we were surprised when we did see transcripts that were significantly different across treatment groups and across strains (FIG. 12) We observed a significant increase in Agtrap expression levels compared to controls in SHR and we did not observe a similar change in WKY. Similarly, Ptgr1 showed increased expression levels in treated versus control groups in SHR, but not in WKY. Taken together with the likelihood of a double-negative feed-forward disinhibition, there appears to be a sensitive threshold of microRNA expression in these animals. We postulate that SHR have been rewired by increased microRNA expression levels which are contributing to hypertension at the onset stage. The double-negative feed-forward disinhibition causes the system to be extremely sensitive to any molecular changes in microRNA expression levels. Therefore, when we intervene, the restoration of molecular balances is immediate and long-standing. However, the threshold for intervention does not appear to exist in WKY because WKY rats do not exhibit increased sensitivity to microRNA intervention as they have much lower microRNA expression levels at the onset stage to begin with. Therefore, intervening in WKY does not exhibit physiological or molecular changes in nearly the same capacity as the SHR intervention.

Hypertension in a Systems Context

Organ Dysregulation in Hypertension. Hypertension is a polygenic, multi-organ disease. As such, there has been much controversy over which organ the disease is driven by. We do know that several organs, including the brain, heart, and kidney are essential in the maintenance and regulation of blood pressure (Burnier 2016; Guyenet 2006a; B. J. Morris and Dampney 2015; Pagani and Lucini 2001). Interestingly, our lab has performed a multi-organ study for a battery of 25 key genes, where we evaluated tissue from the heart, liver, lung, adrenal gland, kidney, spleen and brainstem across 5 time points throughout the course of development of hypertension, and we used computational modeling to determine the order of dynamics for the gene expression changes (Anderson, DeCicco et al. 2017). We concluded that the brain dysregulation occurs before many of the other organ changes (Anderson, DeCicco et al. 2017). The microRNA data becomes more impactful in this case, which is perhaps why the interventions of LNAs we performed may be having such a sustained effect. Our results suggest that the brain experiences gene network deregulation first, compared to the rest of the organs Anderson, DeCicco et al. 2017, DeCicco et al. 2015; Miller et al. 2010a; Vadigepalli et al. 2012b). If the microRNAs we discovered to be relevant are causing all of these changes, like our data suggest, then the long-standing physiological effect of the intervention may give credence to these microRNAs as candidates for future therapeutics.

Leukotriene B4 in Hypertension: Before our work, there had been one study which found that LTB4 was elevated in the NTS of SHR (Waki et al. 2013a). We linked an enzyme that is responsible for the LTB4 degradation, Ptgr1, to the microRNAs we discovered to be playing a role in hypertension through bioinformatics prediction, and anti-correlations in expression levels (DeCicco et al. 2015). Based on our data combined with the previous study, we assayed several genes responsible for the biosynthesis and degradation of Ltb4. However, we found that Ptgr1 was the only transcript that was expressed at significantly different levels in SHR compared to WKY at the hypertension onset stage (FIG. 9) (Hendy et al. 2016). Furthermore, systemic treatment with an antagonist of the Ltb4r decreased hypertension and other inflammatory cell infiltration in SHR (Hendy et al., 2016). Taken together with the microRNA intervention study, our data suggests that microRNA-135a could be directly linked to the blood pressure decrease we have observed in LTB4 blockade. Further studies will be required to fully test this mechanistic interaction. However, based on the LTB4 studies, which originated from NTS, and then showed promise as a systemic intervention, we might consider a systemic microRNA intervention on this pathway to potentially have a physiological effect.

Cell-type contribution in CNS to hypertension: The microRNAs we highlighted as significant though our work in characterization of the NTS and RVLM in SHR were previously shown to be enriched in certain cell types in the brain. i.e.) miR-135a; astrocytes and miR-376a; neurons. With evidence that correlations between these microRNAs and putative targets are retained at the single cell level, there appears to be more discoveries to make in parsing out the cell-type contribution to the development of hypertension in the development of hypertension.

Previously, it has been shown that neurons are adaptable, and that they can be found across a spectrum of phenotypes despite then being categorized previously by expression of one cell-type marker (Park, Brureau, et al. 2014; Park, Ogunnaike, et al. 2014). With the integration of RNA-sequencing into our biological toolboxes, we have discovered as a scientific community, that single cells exhibit increased levels of variability across populations, but that the variability can be structured in a way to reveal biological conclusions (Dueck, Eberwine, and Kim 2016; J. Kim and Eberwine 2010; Park, Brureau, et al. 2014). While there have been several small RNA sequencing studies in different tissue types, including vascular smooth muscle cells, and different organs in the rat, there have been limited global microRNA profiling studies performed at the single cell level (Jin et al. 2012; Linsen et al. 2010). While it may not be immediately necessary to dive straight into single-cell small RNA-sequencing, it is crucial to account for the cell to cell variability in expression, and to account for microRNAs and other non-coding RNAs when evaluating the disease context (Baras et al. 2015). As we have shown some network properties are very robust across scales, from tissue to single cells, some are not. It is helpful to dissect the contribution to the tissue-scale from the single cell scale. Accounting for microRNA expression and variability will enhance our understanding of biological systems and disease, as most diseases thus far have been evaluate from the tissue-level.

Human Correlations:

Our data have a plethora of support for translation from model species to humans. First, the microRNAs and transcripts we discovered through our analysis have several areas highly conserved across species (FIG. 7). Furthermore, a small quantitative trait loci study based off of NCBI gene mapping was performed for all of the microRNAs found to be significant in the development of hypertension by mapping genetic location of the microRNAs to the genome in the NCBI database which displays known associated QTLs. In conjunction with the copy number variation study performed in SHR, we found microRNA-135a has been associated previously with quantitative trait loci including Cardiac Mass QTL 6, linking it indirectly to QTL associated with hypertension (Charchar et al. 2010; Moreno et al. 2003). Additionally, miR-376a has been associated with several blood pressure QTLs including 211 and 213 (Stoll et al. 2001). While these QTL mapping are to rat QTLs, the conservation of sequence to human equivalents predicts their therapeutic use in vivo in human patients.

Additionally, genome wide association studies in humans have identified Agtrap mutations as associated with decreased hypertension risk, and other QTLs associated with hypertension (Flister et al. 2013). Since microRNA-135a has been predicted to target Agtrap, and since Agtrap expression levels were significantly increased upon microRNA inhibition, we hypothesize the effect to be translational. So, while there is some evidence supporting our data with human correlation, studying brain contributions to hypertension in humans serves still to be a difficult task that requires further investigation.

Therapeutic Potential of microRNAs:

As therapeutics, microRNAs can be used both as drugs and biomarkers. Circulating biomarkers are especially useful in diagnosing disease because obtaining patient blood is a relatively routine procedure. miR-17-5p has been shown to be a circulating biomarker of coronary atherosclerosis (J. Chen et al. 2015). Also, a panel of microRNAs, including miR-30a, miR-126 and let-7b, has been shown to be biomarkers in human ischemic stroke (Long et al. 2013). Related to hypertension, there are several circulating microRNA biomarkers; however, none exist currently for neurogenic hypertension. In pulmonary hypertension, miR-451 and miR-1246 appear to indicate pulmonary hypertension in patients (Wei et al. 2013).

Furthermore, as drug targets, microRNAs are positioned to serve several advantages compared to small molecule inhibitors or other treatment regiments. microRNAs can serve as gene hubs linking multiple signaling pathways in a large disease-related signaling network. In breast cancer this has proven to be useful as miR-940 was identified by using this approach, and has been shown to be a critical actin cytoskeletal regulator (Bhajun et al. 2015). In hypertension, miR-483-3p, which was shown through luciferase vectors to target four different genes related to Ang II signaling, and it has expression correlated with this pathway (Kemp et al. 2014). The clinical utility of microRNAs as therapeutics has been shown in a few instances including the delivery of miR-219 intranasally to help treat demyelination disorders and the drug Miravirsen, a locked nucleic acid antisense to miR-122, which is currently in clinical trials to treat hepatitis C infection (Janssen et al. 2013; Pusic and Kraig 2014). In summary, microRNAs show potential as molecular drivers with therapeutic potential in neurogenic hypertension, and further studies will be useful to provide more evidence of the power of small, non-coding RNA in complex diseases like hypertension.

The rodent model, and specifically the rat model, used here recapitulates many of the features of human essential hypertension, and we have all scientific reasons to support the role of microRNA-376a and microRNA-135a in the CNS in SHR, we have not evaluated any other rodent model for drug safety or efficacy, and therefore using a single animal model poses a limitation in the work as it stands (Doggrell and Brown 1998; Hartung 2008).

Delivery of Therapeutics

Stereotaxic Injections of Locked Nucleic Acids in animal models are useful and may be repeated for similar human procedures. In the animal models, a 25 uL injection consisted of a 1:1 ratio of anti-miR-376a Locked Nucleic Acid (LNA, Exiqon) 10 uM solution in artificial cerebrospinal fluid in combination with anti-miR-135a LNA in 10 uM solution, this condition was considered AM-Combo. A negative control antisense oligonucleotide LNA (a sequence that does not align to any known microRNA or mRNA transcript), called "Scrambled". No surgery and sham surgery conditions were also assayed. Sham surgeries included cannulas that were inserted and an empty needle was placed for the duration of the corresponding injection time were also performed. The rats were anesthetized by isoflurane inhalation and placed in a stereotactic instrument (Stoelting Co., Wood Dale, Ill., USA), positioned, and the incision site appropriately prepared. A small incision was made, and the skull was then exposed and cleaned and a small burr hole was drilled using a dental drill or Dremal rotary tool, and cannula was mounted with dental cement to skull screws. The incision was closed and the rats were placed on an isothermal pad at 37° C. and continuously observed following surgery until recovery. Topical analgesic was applied immediately following the surgical procedure and as needed thereafter. The LNAs were injected using a Hamilton syringe with a 35-gauge needle (Reno, Nev., USA) over a 30 minute time period into the fourth ventricle using the coordinates: 11.3 mm caudal to bregma, 0.5 mm lateral to midline, and 7 mm below the surface of the skull.

Six SHR were injected with AM-Combo, three were injected with AM-376a, three were injected with AM-135, and four SHR were injected with scrambled oligonucleotide control. Two SHR underwent sham surgery where a cannula was placed, but no injection was given. Four SHR were maintained with the cohort as untreated. Four WKY were injected with AM-Combo and four were injected with scrambled negative control. Three WKY animals underwent sham surgery and four were kept untreated. Blood pressure was measured over multiple days for up to two weeks. Animals were sacrificed two weeks post injection. The individual injections were evaluated as an independent experiment.

Delivery of anti-miR therapeutics may be in several forms in human patients. A first example is for direct ICV application to a patient. There are numerous instances where a patient is under anesthesia or surgical procedure where direct application through ICV is a routine option for therapeutic treatment. This suggests a shorter term treatment cycle, e.g. a single administration or a series of administrations over the course of 1-30 days.

In preferred treatments, inhalation of packaged anti-miR therapeutics is utilizes for in vivo administration. For example, the anti-miR can be given in an intranasal delivery vehicle. Previously such therapies have been used in other treatment models, e.g. in epilepsy.

Further known models of therapeutic delivery include use of formulated, synthetic, double-stranded miRNA mimics. These can be formulated in an appropriate carrier for injection, ingestion, or inhalation to the body. Certain other administration methods include viral delivery. For example viral constructs that overexpress a particular anti-miR (135a or 376a, for example) can be injected to the patient or given intranasally. The use of such viral vehicles is well known in the art and thus not described herein in detail.

Anti-miR therapeutics can be modified with 2'-O-methyl, 2'-O-methoxyethyl, or 2',4'-methylene (LNA) treatments to stabilize the nucleotides. These can then be injected, inhaled, or taken orally as known to one of ordinary skill in the art.

Other delivery methods may utilize certain encapsulated materials or liposome delivery vehicles. Combinations of the above therapeutic delivery methods may be utilized to formulate and generate sufficient bioavailability and safe dose profile for human in vivo administration.

CONCLUSION

Understanding biological problems, like disease, are complicated. But, thanks to the advent of technology, big data, and multidisciplinary approaches integrating experimental work both in vivo and in vitro, bioinformatics and computational approaches, we can further our understanding of disease with a significant increase in speed and impact. Expediting knowledge acquisition and innovating new approaches to disease prevention and cure can now incorporate dynamics of disease development, unconventional therapeutic interventions, and finer dosing regimens. However, it is these efforts, like the small study examined here, on microRNAs and hypertension, which can help fill in pieces of a larger puzzle in the story of our understanding of disease progression and treatment.

When considering the network of organs and body systems that drive and perpetuate hypertension, there is no doubt that the NTS is a node with vital connectivity and a large amount of control potential. Many of the pharmacological interventions that show clinical efficacy in lowering blood pressure in hypertensive patients work at many different sites of action in parallel, even if the presumed mechanism of action is narrowly defined. Consider, as an example the angiotensin receptor blocker losartan, whose mechanism of action generally is defined as working on angiotensin-1 receptors in the heart, vasculature, and kidney, but which also has effects in the brain that were not originally well-defined. Pharmacological interventions also have the tendency to drive a very large direct effect on only one receptor or protein, which then has downstream consequences that lead to renormalizing blood pressure. When all of the network interactions are considered both between organs as well as within organ tissue at a molecular level, it seems this network behavior can be shifted by a large, but narrow perturbation such as renal denervation or taking a drug that blocks angiotensin receptors.

The use of microRNAs, however, does not lead to large, narrow changes in the network. Any given microRNA has hundreds to thousands of putative binding sites on known mRNA transcripts and plays only a small role in the overall expression levels of that transcript. Rather than thinking of microRNAs as gene expression modulators, it would perhaps be more functionally useful to think of them as gene network tuners. Through small, broad changes in networks, it is possible to retune the network behavior that may lead to distinct physiology. It is clear from FIGS. 1 and 3 that such physiological outcomes are possible. What remains is picking apart the molecular mechanisms that drive this behavior. This will not likely be accomplished through the traditional series of siRNA or genetic knockout models. A network-based approach will be required including the measuring of hundreds to thousands of transcripts and mathematical techniques to deconvolute the non-linear effects. These initial results in examination of gene expression suggest that there are not likely very large changes in any gene transcript that result from knockdown of microRNAs, but that there is vast number of distinct transcripts that are affected.

Many cases of essential hypertension are refractory to current treatment paradigms. There are several treatments that each work for a cohort of patients, but not all and that much of the time the relief from hypertension is not permanent. If essential hypertension is a disease that follows from a set of network properties, then it is possible that adaptions within this network could lead to recalcitrant high blood pressure. By treating one or another aspect of the network while leaving the rest unaltered may not be a large enough perturbation in order to generate a new network state. However, it is possible that several small perturbations in mRNA levels across several genes are enough to push the network into a new state. If this is enough to cure hypertension has yet to be demonstrated, but the results here suggest that such an approach may have value and should be carefully considered as a means of treating complex diseases that emerge out of systems of network interactions.

Through application of certain anti-microRNA, synergistic effects can be seen. We show that small perturbations in the gene regulatory networks in the brainstem by selectively blocking two microRNAs (miR-135a and miR-376a) are sufficient to prevent development of hypertension in a well-established animal model of human essential hypertension. Furthermore, this effect appears driven by only modest changes in putative gene targets of these microRNAs, suggesting that the combination of genes that are targeted in the network is responsible for the effect rather than altering the expression of just one gene or another. Furthermore, our results demonstrate that a combinatorial intervention into inhibiting two microRNAs in vivo has a synergistic effect compared to inhibiting the activity of only one of the microRNAs at a time (compare the reduction in FIG. 8A to the decrease in blood pressure in FIG. 10).

In the narrowest sense, we can prevent the increase in blood pressure by inhibiting two microRNAs miR-135a and miR-376a in vivo. This effect of anti-microRNA intervention is achieved through a regulatory network that leads to disinhibiting the negative regulators of key signaling pathways that are amplified during the development of hypertension (FIG. 6B).

Accordingly, the data reveals that regulation of certain receptors and or pathways in the body can lead to regulation or modification of hypertension in human. A particular embodiment is directed to a pharmaceutical composition comprising an effective amount of an anti-miR-135a-5p.

A further embodiment is directed to a pharmaceutical composition comprising an effective amount of an anti-miR-376a-5p.

A further embodiment is directed to a pharmaceutical composition comprising an anti-miR-135a-5p and an anti-miR-376a-5p.

A further embodiment is directed to a method for treating hypertension comprising administering to a human patient an effective amount of any one of the pharmaceutical compositions comprising an anti-miR-376a-5p, an anti-miR-135a-5p, or combinations thereof.

In particular, compositions are suitable for regulating PTGR1 expression in astrocytes by direct action on PTGR1 mRNA, thereby decreasing hypertension. Therefore, the anti-miR to miR-135a specifically decreases the levels of miR-135a, leading to an increase in the PTGR1 mRNA levels. Thus, these anti-miR are effective in reducing hypertension or preventing or reducing the likelihood of occurrence of essential hypertension.

Further the compositions comprising an anti-miR for miR-376a, regulate AGTRAP expression in neurons by direct action on AGTRAP mRNA. The anti-miR to miR-376a thereby specifically decreases the levels of miR-376a, leading to an increase in the AGTRAP mRNA levels. Based on the studies, an anti-miR to miR-376a specifically prevents development of hypertension or reduces the likelihood of occurrence of essential hypertension.

What is claimed is:

1. A method for treating hypertension comprising administering to a human patient an effective amount of a pharmaceutical composition comprising an anti-miR-376a-5p effective in regulating AGTRAP expression in neurons by direct action on AGTRAP mRNA, wherein the anti-miR-376a thereby specifically decreases the levels of miR-376a, leading to an increase in the AGTRAP mRNA levels, and wherein the anti-miR to miR-376a specifically prevents development of hypertension or reduces the likelihood of occurrence of essential hypertension.

2. A method of treatment of hypertension comprising: administering to a patient a first therapeutic comprising at least one anti-miR therapeutic selected from the group consisting of anti-miR 135a-5p and anti-miR376a-5p for a sufficient amount of time to reduce the mean arterial pressure in a patient to below 110 mm Hg;
    testing said patient for mean arterial pressure at least 24 hours after administration of the at least one anti-miR selected from the group consisting of anti-miR 135a-5p and anti-miR 376a-5p; and
    administering to said patient a second therapeutic comprising both anti-miR 135a-5p and anti-miR 376a-5p.

3. A method of treatment of hypertension comprising administering to a patient a therapeutic comprising one of anti-miR-135a or anti-miR-376a; measuring hypertension at a first time before administration and again at a second time after administration; evaluating mean arterial pressure in said patient with a target of 110 mm Hg in said patient; and providing a second dose of the therapeutic every 28 days to maintain said therapeutic levels in the body, wherein the second dose comprises a combination of both anti-miR-135a and of anti-miR-376a if said second measurement is not lower than 110 mm Hg.

* * * * *